(12) United States Patent
Shmayahu et al.

(10) Patent No.: US 11,010,983 B2
(45) Date of Patent: May 18, 2021

(54) TISSUE MODEL DYNAMIC VISUAL RENDERING

(71) Applicant: Navix International Limited, Road Town (VG)

(72) Inventors: Yizhaq Shmayahu, Ramat-HaSharon (IL); Yitzhack Schwartz, Haifa (IL)

(73) Assignee: Navix International Limited, Road Town (VG)

( * ) Notice: Subject to any disclaimer, the term of this patent is extended or adjusted under 35 U.S.C. 154(b) by 0 days.

(21) Appl. No.: 16/461,384

(22) PCT Filed: Nov. 16, 2017

(86) PCT No.: PCT/IB2017/057169
§ 371 (c)(1),
(2) Date: May 16, 2019

(87) PCT Pub. No.: WO2018/092059
PCT Pub. Date: May 24, 2018

(65) Prior Publication Data
US 2019/0340837 A1 Nov. 7, 2019

Related U.S. Application Data

(60) Provisional application No. 62/422,705, filed on Nov. 16, 2016, provisional application No. 62/422,708, (Continued)

(51) Int. Cl.
*G06T 19/20* (2011.01)
*A61B 90/00* (2016.01)
(Continued)

(52) U.S. Cl.
CPC ............ *G06T 19/20* (2013.01); *A61B 5/1076* (2013.01); *A61B 90/37* (2016.02); *G06T 17/00* (2013.01);
(Continued)

(58) Field of Classification Search
CPC ..... G06T 19/20; G06T 17/00; G06T 2210/41; G06T 2219/004; G06T 2219/2021; A61B 90/37; A61B 5/1076
See application file for complete search history.

(56) References Cited

U.S. PATENT DOCUMENTS 4,917,097 A   4/1990  Proudian et al.
5,553,611 A   9/1996  Budd et al.
(Continued)

FOREIGN PATENT DOCUMENTS

CA     2237992    3/1998
EP     0974936    1/2000
(Continued)

OTHER PUBLICATIONS

Communication Relating to the Results of the Partial International Search dated Aug. 22, 2016 From the International Searching Authority Re. Application No. PCT/IB2016/052686.
(Continued)

*Primary Examiner* — Phuc N Doan

(57) ABSTRACT

Disclosed herein is a method of graphically presenting an indicating marker over a 3-D model of a tissue surface during a catheterization procedure, comprising determining a region over the 3-D model, deforming the indicating marker to congruently match a shape defined by the 3-D model across the region at a plurality of positions; and rendering the 3-D model into an image including the deformed indicating marker by generating an image of the 3-D model covered by said deformed indicating marker.

32 Claims, 20 Drawing Sheets

Related U.S. Application Data filed on Nov. 16, 2016, provisional application No. 62/422,713, filed on Nov. 16, 2016.

(51) Int. Cl.
  *A61B 5/107* (2006.01)
  *G06T 17/00* (2006.01)

(52) U.S. Cl.
  CPC .... *G06T 2210/41* (2013.01); *G06T 2219/004* (2013.01); *G06T 2219/2021* (2013.01)

(56) References Cited

U.S. PATENT DOCUMENTS

| | | | |
|---|---|---|---|
| 5,662,108 A | 9/1997 | Budd et al. | |
| 5,697,377 A | 12/1997 | Wittkampf | |
| 5,724,978 A | 3/1998 | Tenhoff | |
| 5,983,126 A | 11/1999 | Wittkampf | |
| 6,019,725 A | 2/2000 | Vesely et al. | |
| 6,038,468 A | 3/2000 | Rex | |
| 6,240,307 B1 | 5/2001 | Beatty et al. | |
| 6,266,552 B1 | 7/2001 | Slettenmark | |
| 6,301,496 B1 | 10/2001 | Reisfeld | |
| 6,317,621 B1 | 11/2001 | Graumann et al. | |
| 6,322,558 B1 | 11/2001 | Taylor et al. | |
| 6,423,057 B1 | 7/2002 | He et al. | |
| 6,515,657 B1 | 2/2003 | Zanelli | |
| 6,640,119 B1 | 10/2003 | Budd et al. | |
| 6,728,562 B1 | 4/2004 | Budd et al. | |
| 6,826,420 B1 | 11/2004 | Beatty et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,187,973 B2 | 3/2007 | Hauck | |
| 7,189,208 B1 | 3/2007 | Beatty et al. | |
| 7,306,593 B2 | 12/2007 | Keidar et al. | |
| 7,881,769 B2 | 2/2011 | Sobe | |
| 7,996,060 B2 | 8/2011 | Trofimov et al. | |
| 9,101,333 B2 | 8/2015 | Schwartz | |
| 9,259,290 B2 | 2/2016 | Jenkins et al. | |
| 10,292,588 B2 | 5/2019 | Ben-Haim | |
| 2002/0068931 A1 | 6/2002 | Wong et al. | |
| 2003/0074011 A1 | 4/2003 | Gilboa et al. | |
| 2003/0220636 A1 | 11/2003 | Bowman et al. | |
| 2004/0039278 A1 | 2/2004 | Wacker et al. | |
| 2004/0044279 A1 | 3/2004 | Lewin et al. | |
| 2004/0097805 A1 | 5/2004 | Verard et al. | |
| 2004/0147920 A1 | 7/2004 | Keidar | |
| 2004/0176804 A1 | 9/2004 | Palti | |
| 2005/0015006 A1 | 1/2005 | Mitschke et al. | |
| 2005/0033164 A1 | 2/2005 | Yatsuo et al. | |
| 2005/0054913 A1 | 3/2005 | Duerk et al. | |
| 2005/0054918 A1 | 3/2005 | Sra | |
| 2005/0058328 A1 | 3/2005 | Moreau-Gobard | |
| 2005/0245814 A1 | 11/2005 | Anderson et al. | |
| 2006/0089552 A1 | 4/2006 | Goldbach | |
| 2006/0241401 A1 | 10/2006 | Govari et al. | |
| 2007/0043296 A1 | 2/2007 | Schwartz | |
| 2007/0049915 A1 | 3/2007 | Haemmerich et al. | |
| 2007/0106289 A1 | 5/2007 | O'Sullivan | |
| 2007/0167706 A1 | 7/2007 | Boese et al. | |
| 2007/0167726 A1 | 7/2007 | Unal et al. | |
| 2008/0114235 A1 | 5/2008 | Unal et al. | |
| 2008/0118135 A1 | 5/2008 | Averbuch et al. | |
| 2008/0125775 A1 | 5/2008 | Morris | |
| 2008/0177175 A1 | 7/2008 | Mottola et al. | |
| 2008/0183070 A1 | 7/2008 | Unal et al. | |
| 2008/0190438 A1 | 8/2008 | Harlev et al. | |
| 2008/0208031 A1 | 8/2008 | Kurpad et al. | |
| 2008/0221425 A1 | 9/2008 | Olson et al. | |
| 2008/0230705 A1 | 9/2008 | Rousso et al. | |
| 2008/0275440 A1 | 11/2008 | Kratoska et al. | |
| 2008/0275465 A1 | 11/2008 | Paul et al. | |
| 2009/0010519 A1 | 1/2009 | Wakai et al. | |
| 2009/0015818 A1 | 1/2009 | Ikeda et al. | |
| 2009/0148012 A1 | 6/2009 | Altmann et al. | |
| 2009/0171274 A1 | 7/2009 | Harlev et al. | |
| 2009/0221908 A1 | 9/2009 | Glossop | |
| 2009/0225077 A1 | 9/2009 | Sudarsky et al. | |
| 2009/0262109 A1 | 10/2009 | Markowitz et al. | |
| 2009/0275828 A1 | 11/2009 | Shachar et al. | |
| 2009/0281566 A1 | 11/2009 | Edwards et al. | |
| 2010/0063400 A1 | 3/2010 | Hall et al. | |
| 2010/0217116 A1 | 8/2010 | Eck et al. | |
| 2010/0249579 A1 | 9/2010 | Starks | |
| 2010/0274239 A1 | 10/2010 | Paul et al. | |
| 2010/0283484 A1 | 11/2010 | Cohen et al. | |
| 2010/0312094 A1 | 12/2010 | Guttman et al. | |
| 2010/0312096 A1 | 12/2010 | Guttman et al. | |
| 2011/0106221 A1 | 5/2011 | Neal, II et al. | |
| 2011/0144524 A1* | 6/2011 | Fish | A61B 34/10 600/547 |
| 2011/0230758 A1 | 9/2011 | Eichler | |
| 2011/0282186 A1 | 11/2011 | Harlev et al. | |
| 2012/0059249 A1 | 3/2012 | Verard et al. | |
| 2012/0078129 A1 | 3/2012 | Bailin | |
| 2012/0109115 A1 | 5/2012 | Condie et al. | |
| 2012/0116210 A1* | 5/2012 | Zino | A61B 5/742 600/416 |
| 2012/0123250 A1 | 5/2012 | Pang et al. | |
| 2012/0150046 A1 | 6/2012 | Watson et al. | |
| 2012/0172724 A1 | 7/2012 | Hill et al. | |
| 2012/0173217 A1 | 7/2012 | Heimbecher | |
| 2012/0197243 A1 | 8/2012 | Sherman et al. | |
| 2012/0238866 A1 | 9/2012 | Wang et al. | |
| 2013/0137980 A1 | 5/2013 | Waters et al. | |
| 2013/0272593 A1 | 10/2013 | Lee et al. | |
| 2013/0310673 A1 | 11/2013 | Govari et al. | |
| 2014/0024911 A1 | 1/2014 | Harlev et al. | |
| 2014/0088943 A1 | 3/2014 | Trayanova et al. | |
| 2014/0187949 A1 | 7/2014 | Zhao et al. | |
| 2014/0243641 A1 | 8/2014 | Boveja et al. | |
| 2014/0243813 A1 | 8/2014 | Paul et al. | |
| 2014/0275991 A1 | 9/2014 | Potter et al. | |
| 2014/0330111 A1 | 11/2014 | Lichtenstein et al. | |
| 2015/0080762 A1 | 3/2015 | Kassab et al. | |
| 2015/0099942 A1 | 4/2015 | Edouard | |
| 2015/0223757 A1 | 8/2015 | Werneth et al. | |
| 2015/0254422 A1* | 9/2015 | Avisar | H04L 67/10 703/11 |
| 2016/0095651 A1 | 4/2016 | Deno et al. | |
| 2016/0095653 A1 | 4/2016 | Lambert et al. | |
| 2016/0242667 A1 | 8/2016 | Fay et al. | |
| 2016/0249989 A1* | 9/2016 | Devam | G09B 23/285 345/633 |
| 2016/0270683 A1 | 9/2016 | Grass et al. | |
| 2017/0014181 A1 | 1/2017 | Bar-Tal et al. | |
| 2017/0098055 A1* | 4/2017 | Voth | G16H 50/50 |
| 2017/0156792 A1 | 6/2017 | Ziv-Ari et al. | |
| 2017/0263021 A1 | 9/2017 | Ben Haim | |
| 2017/0281281 A1* | 10/2017 | He | A61B 34/20 |
| 2018/0153437 A1 | 6/2018 | Schwartz et al. | |
| 2019/0328275 A1 | 10/2019 | Shmayahu et al. | |
| 2019/0328458 A1 | 10/2019 | Shmayahu et al. | |

FOREIGN PATENT DOCUMENTS

| | | |
|---|---|---|
| EP | 1472975 | 11/2004 |
| EP | 1504713 | 2/2005 |
| EP | 1726268 | 11/2006 |
| EP | 1767166 | 3/2007 |
| EP | 1853162 | 11/2007 |
| EP | 1943974 | 7/2008 |
| EP | 2075763 | 7/2009 |
| EP | 2248480 | 11/2010 |
| EP | 2712543 | 4/2014 |
| EP | 2777584 | 9/2014 |
| HR | P20131208 | 3/2014 |
| JP | 2001-340336 | 12/2001 |
| WO | WO 97/29682 | 8/1997 |
| WO | WO 98/01069 | 1/1998 |
| WO | WO 2007/067628 | 6/2007 |

(56) References Cited

FOREIGN PATENT DOCUMENTS

| | | |
|---|---|---|
| WO | WO 2008/097767 | 8/2008 |
| WO | WO 2008/104914 | 9/2008 |
| WO | WO 2010/102794 | 9/2010 |
| WO | WO 2010/129095 | 11/2010 |
| WO | WO 2011/142931 | 11/2011 |
| WO | WO 2012/092016 | 7/2012 |
| WO | WO 2013/192598 | 12/2013 |
| WO | WO 2014/118535 | 8/2014 |
| WO | WO 2014/182822 | 11/2014 |
| WO | WO 2016/038499 | 3/2016 |
| WO | WO 2016/088084 | 6/2016 |
| WO | WO 2016/135584 | 9/2016 |
| WO | WO 2016/181315 | 11/2016 |
| WO | WO 2016/181316 | 11/2016 |
| WO | WO 2016/181317 | 11/2016 |
| WO | WO 2016/181318 | 11/2016 |
| WO | WO 2016/181320 | 11/2016 |
| WO | WO 2018/011757 | 1/2018 |
| WO | WO 2018/078540 | 5/2018 |
| WO | WO 2018/092059 | 5/2018 |
| WO | WO 2018/092062 | 5/2018 |
| WO | WO 2018/092063 | 5/2018 |
| WO | WO 2018/092070 | 5/2018 |
| WO | WO 2018/092071 | 5/2018 |
| WO | WO 2018/130974 | 7/2018 |
| WO | WO 2018/130976 | 7/2018 |
| WO | WO 2018/130981 | 7/2018 |
| WO | WO 2018/134747 | 7/2018 |
| WO | WO 2018/146613 | 8/2018 |
| WO | WO 2018/207128 | 11/2018 |
| WO | WO 2019/034944 | 2/2019 |
| WO | WO 2019/035023 | 2/2019 |
| WO | WO 2019/111180 | 6/2019 |

OTHER PUBLICATIONS

Communication Relating to the Results of the Partial International Search dated Aug. 22, 2016 From the International Searching Authority Re. Application No. PCT/IB2016/052688.
Communication Relating to the Results of the Partial International Search dated Aug. 25, 2016 From the International Searching Authority Re. Application No. PCT/IB2016/052692.
Communication Relating to the Results of the Partial International Search dated Aug. 26, 2016 From the International Searching Authority Re. Application No. PCT/IB2016/052687.
International Preliminary Report on Patentability dated May 9, 2019 From the International Bureau of WIPO Re. Application No. PCT/IB2017/056616. (8 Pages).
International Preliminary Report on Patentability dated Nov. 23, 2017 From the International Bureau of WIPO Re. Application No. PCT/IB2016/052686. (11 Pages).
International Preliminary Report on Patentability dated Nov. 23, 2017 From the International Bureau of WIPO Re. Application No. PCT/IB2016/052687. (10 Pages).
International Preliminary Report on Patentability dated Nov. 23, 2017 From the International Bureau of WIPO Re. Application No. PCT/IB2016/052688. (9 Pages).
International Preliminary Report on Patentability dated Nov. 23, 2017 From the International Bureau of WIPO Re. Application No. PCT/IB2016/052690. (9 Pages).
International Preliminary Report on Patentability dated Nov. 23, 2017 From the International Bureau of WIPO Re. Application No. PCT/IB2016/052692. (13 Pages).
International Preliminary Report on Patentability dated May 31, 2019 From the International Bureau of WIPO Re. Application No. PCT/IB2017/057186. (13 Pages).
International Search Report and the Written Opinion dated Feb. 1, 2018 From the International Searching Authority Re. Application No. PCT/IB2017/056616. (14 Pages).
International Search Report and the Written Opinion dated Jan. 2, 2019 From the International Searching Authority Re. Application No. PCT/IB2018/056158. (16 Pages).
International Search Report and the Written Opinion dated Jan. 3, 2017 From the International Searching Authority Re. Application No. PCT/IB2016/052688. (14 Pages).
International Search Report and the Written Opinion dated May 3, 2018 From the International Searching Authority Re. Application No. PCT/IB2017/057185. (18 Pages).
International Search Report and the Written Opinion dated Jun. 6, 2018 From the International Searching Authority Re. Application No. PCT/IB2018/050201. (24 Pages).
International Search Report and the Written Opinion dated May 9, 2018 From the International Searching Authority Re. Application No. PCT/IB2018/050192. (16 Pages).
International Search Report and the Written Opinion dated Oct. 12, 2016 From the International Searching Authority Re. Application No. PCT/IB2016/052686.
International Search Report and the Written Opinion dated Aug. 13, 2018 From the International Searching Authority Re. Application No. PCT/IB2018/053258. (15 Pages).
International Search Report and the Written Opinion dated Apr. 14, 2019 From the International Searching Authority Re. Application No. PCT/IB2018/059672. (49 Pages).
International Search Report and the Written Opinion dated Oct. 16, 2017 From the International Searching Authority Re. Application No. PCT/IB2017/054263. (16 Pages).
International Search Report and the Written Opinion dated Oct. 17, 2016 From the International Searching Authority Re. Application No. PCT/IB2016/052692.
International Search Report and the Written Opinion dated Oct. 21, 2016 From the International Searching Authority Re. Application No. PCT/IB2016/052687. (16 Pages).
International Search Report and the Written Opinion dated Feb. 22, 2018 From the International Searching Authority Re. Application No. PCT/IB2017/057169. (14 Pages).
International Search Report and the Written Opinion dated Feb. 22, 2018 From the International Searching Authority Re. Application No. PCT/IB2017/057175. (15 Pages).
International Search Report and the Written Opinion dated Feb. 22, 2018 From the International Searching Authority Re. Application No. PCT/IB2017/057176. (15 Pages).
International Search Report and the Written Opinion dated Aug. 25, 2016 From the International Searching Authority Re. Application No. PCT/IB2016/052690.
International Search Report and the Written Opinion dated Apr. 30, 2018 From the International Searching Authority Re. Application No. PCT/IB2017/057186. (22 Pages).
International Search Report and the Written Opinion dated Apr. 30, 2018 From the International Searching Authority Re. Application No. PCT/IB2018/050195. (16 Pages).
International Search Report and the Written Opinion dated Nov. 30, 2018 From the International Searching Authority Re. Application No. PCT/IB2018/055344. (15 Pages).
Invitation to Pay Additional Fees and Communication Related to the Results of the Partial International Search and the Provisional Opinion dated Feb. 22, 2018 From the International Searching Authority Re. Application No. PCT/IB2017/057186. (12 Pages).
Invitation to Pay Additional Fees, Communication Relating to the Results of the Partial International Search and the Provisional Opinion dated Mar. 5, 2018 From the International Searching Authority Re. Application No. PCT/IB2017/057185. (13 Pages).
Invitation to Pay Additional Fees, Communication Relating to the Results of the Partial International Search and the Provisional Opinion dated Apr. 25, 2018 From the International Searching Authority Re. Application No. PCT/IB2018/050201. (14 Pages).
Notice of Allowance dated Dec. 26, 2018 From the US Patent and Trademark Office Re. U.S. Appl. No. 15/572,815. (8 Pages).
Official Action dated Aug. 30, 2018 From the US Patent and Trademark Office Re. U.S. Appl. No. 15/572,815. (22 pages).
Ahn et al. "Height-Based Deformation and Ray Supersampling for Colon Unfolding", ICAT'06 Proceedings of the 16th International Conference on Advances in Artificial Reality and Tele-Existence, Lecture Notes in Computer Science, XP047402101, Hangzhou, China, Nov. 29-Dec. 1, 2006, p. 1098-1107, Nov. 29, 2006. Sections 3.1, 3.3, 5, Figs.2, 4, 5.

(56) References Cited

OTHER PUBLICATIONS

Anter et al. "Evaluation of a Novel High-Resolution Mapping Technology for Ablation of Recurrent Scar-Related Atrial Tachycardias," Heart Rhythm, 13(10): 2048-2055, Oct. 2016.
Arujuna et al. "Acute Pulmonary Vein Isolation Is Achieved by a Combination of Reversible and Irreversible Atrial Injury After Catheter Ablation: Evidence From Magnetic Resonance Imaging", Circulation: Arrhythmia and Electrophysiology, 5(4): 691-700, Published Online May 31, 2012.
Bartroli et al. "Nonlinear Virtual Colon Unfolding", Proceedings of the IEEE Conference on Visualization '01, VIS '01, XP031385694, San Diego, CA, USA, Oct. 21-26, 2001, p. 411-420, Oct. 21, 2001. Sections 4, 4.1, 4.2, 5.1, 7, Figs.1, 7a, 7b, 10.
Black-Maier et al. "Risk of Atrioesophageal Fistula Formation With Contact-Force Sensing Catheters", HeartRhythm, 14(9): 1328-1333, Published Online Apr. 15, 2017.
Bourier et al. "Electromagnetic Contact-Force Sensing Electrophysiological Catheters: How Accurate Is the Technology?", Journal of Cardiovascular Electrophysiology, 27(3): 347-350, Published Online Jan. 16, 2016.
Bourier et al. "Fiberoptic Contact-Force Sensing Electrophysiological Catheters: How Precise Is Technology?", Journal of Cardiovascular Electrophysiology, 28(1): 109-114, Published Online Oct. 24, 2016.
Canpolat et al. "Relationship Between Vitamin D Level and Left Atrial Fibrosis in Patients With Lone Paroxysmal Atrial Fibrillation Undergoing Cryoballoon-Based Catheter Ablation", Journal of Cardiology, 6991): 16-23, Published Online Aug. 21, 2016.
Caspi et al. "Modeling of Arrhythmogenic Right Ventricular Cardiomyopathy With Human Induced Pluripotent Stem Cells", Circulation: Cardiovscular Genetics, 6(6): 557-568, Published Online Nov. 7, 2013.
Cerit et al. "Association of Pre-Ablation Level of Vitamin D With Atrial Fibrillation Recurrence After Catheter Ablation", Europace, 19(9): 1586, Sep. 1, 2017.
Chierchia et al. "An Initial Clinical Experience With a Novel Microwave Radiometry Sensing Technology Used in Irrigated RF Ablation for Flutter", Academic Hospital Brussels, Belgium, 1 P. Jan. 1, 2011.
Crospon "Esophageal Treatment by Esoflip®", Crospon, Product Sheet, 4 P., 2017.
Crospon "Flip® Technology", Crospon, Product Sheet, 6 P., 2017.
Deno et al. "Measurement of Electrical Coupling Between Cardiac Ablation Catheters and Tissue", IEEE Transactions on Biomedical Engineering, 61(3): 765-774, Published Online Nov. 6, 2013.
Eyerly et al. "The Evolution of Tissue Stiffness at Radiofrequency Ablation Sites During Lesions Formation and in the Peri-Ablation Period", Journal of Cardiovascular Electrophysiology, 26(9): 1009-1018, Sep. 2015.
Gabriel "Compilation of the Dielectric Properties of Body Tissues at RF and Microwave Frequencies", Occupational and Environmental Health Directorate, Radiofrequency Radiation Division, Brooks Air Force Base, Texas, USA, Technical Report for the Period Sep. 15, 1993-Dec. 14, 1994, p. 1-16, Jan. 1996.
Gaspar et al. "Use of Electrical Coupling Information (ECI) in AF Catheter Ablation: A Prospective Randomized Pilot Study", HeartRhythm, 10(2): 176-181, Feb. 2013.
General Electric "CardEP: Streamlined Post-Processing for Enhanced Electrophysiology Procedures", General Electric Company, GE Healthcare, Product Description, 2 P., 2016.
Grace "Modifying PVI Lines to Incorporate Non-PV Targets Identified by Pre-Ablation Mapping with the AcQMap System: Update on the UNCOVER-AF Trial," EP Lab Digest, 17(5), May 2017, 5 pages.
Hilbert et al. "An Integrative Approach to Slow Pathway Modulation in AVNRT Using a Novel Ultra High-Density Electroanatomical Mapping System", Clinical Research in Cardiology, XP035518036, 104(8): 697-699, Published Online Mar. 31, 2015.
Ikeda et al. "Microwave Volumetric Temperature Sensor Improves Control of Radiofrequency Lesion Formation and Steam Pop", 33rd Annual Scientific Sessions, Heart Rhythm, Boston, MA, USA, May 9-12, 2012, Session: Role of Autonomics in Catheter Ablation, # AB13-05, May 10, 2012.
Ikeda et al. "Novel Irrigated Radiofrequency Ablation Catheter With Microwave Volumetric Temperature Sensor Predicts Lesion Size and Incidence of Steam Pop in Canine Beating Heart", 33rd Annual Scientific Sessions, Heart Rhythm, Boston, MA, USA, May 9-12, 2012, Poster Session III, # PO3-53, May 10, 2012.
Jiang et al. "Association of Pre-Ablation Level of Potential Blood Markers With Atrial Fibrillation Recurrence After Catheter Ablation: A Meta-Analysis", Europace, 19(3): 392-400, Mar. 1, 2017.
Karim et al. "Surface Flattening of the Human Left Atrium and Proof-of-Concept Clinical Applications", Computerized Medical Imaging and Graphics, 38(4): 251-266, Jun. 2014.
Lardo et al. "Visualization and Temporal/Spatial Characterization of Cardiac Radiofrequency Ablation Lesions Using Magnetic Resonance Imaging", Circulation, 102(6): 698-705, Aug. 8, 2000.
Lemola et al. "Computed Tomographic Analysis of the Anatomy of the Left Atrium and the Esophagus. Implications for Left Atrial Catheder Ablation", Circulation, 110(24): 3655-3660, Published Online Nov. 29, 2004.
Lunak "12 510(k) FDA Summary for Public Disclosure", St. Jude Medical, Section 12, 6 P., Aug. 29, 2013.
McDowell et al. "Virtual Electrophysiological Study of Atrial Fibrillation in Fibrotic Remodeling", PLOS ONE, 10(2): e117110-1-e117110-16, Published Online Feb. 18, 2015.
Myronenko et al. "Non-Rigid Point Set Registration: Coherent Point Drift", Advances in Neural Information Processing Systems, NIPS, 19: 1009-1016, 2009.
Pappone "Carto 3", AF-Ablation, Arrhythmology and Cardiac Electrophysiology Department, 1 P., 2009.
Perazzi et al. "Panoramic Video From Unstructured Camera Arrays", Computer Graphics Forum, 34(2): 57-68, May 2015.
Piorkowski et al. "First in Human Validation of Impedance-Based Catheter Tip-to-Tissue Contact Assessment in the Left Atrium", Study of Clinical Results, Poster, Journal of Cardiovascular Electrophysiology, 20(12): 1366-1373, Published Online Jul. 7, 2009.
Ranjan et al. "Gaps in the Ablation Line as a Potential Cause of Recovery From Electrical Isolation and Their Visualization Using MRI", Circulation: Arrhythmia and Electrophysiology, XP055452459, 4(3): 279-286, Published Online Apr. 14, 2011.
Sanchez-Quintana et al. "Anatomic Relations Between the Esophagus and Left Atrium and Relevance for Ablation of Atrial Fibrillation", Circulation, 112(10): 1401-1406, Published Online Aug. 29, 2005.
Shoemaker et al. "Common Genetic Variants and Response to Atrial Fibrillation Ablation", Circulation: Arrhythmia and Electrophysiology, 8(2): 296-302, Published Online Feb. 14, 2015.
St. Jude Medical "Cardiac Mapping System / ECG. NSite™ NavX™", St. Jude Medical, Products Sheet, 22 P., 2017.
Ueberham et al. "Genetic ACE I/D Polymorphism and Recurrence of Atrial Fibrillation After Catheter Ablation", Circulation: Arrhythmia and Electrophysiology, 6(4): 732-737, Published Online Jul. 22, 2013.
Vandekerckhove et al. "Flutter Ablation With an Irrigated Catheter Using Microwave Radiometry Sensing Technology: First Report in Men", Sint Jan Hospital, Department of Cardiology, Bruges, Belgium, 1 P., Jan. 1, 2011.
Wang et al. "Association of the Angiotensinogen M235T Polymorphism With Recurrence After Catheter Ablation of Acquired Atrial Fibrillation", Journal of the Renin-Angiotensin-Aldosterone System, 16(4): 888-897, Published Online Aug. 3, 2015.
Wang et al. "Colon Unraveling Based on Electrical Field: Recent Progress and Further Work", Proceedings of the SPIE 3660 Medical Imaging '99: Physiology and Function From Multidimensional Images, San Diego, CA, USA, Feb. 1999, XP055479173, 3660: 125-133, May 20, 1999. Abstract, Sections 1, 2.2, 2.3, Figs.2, 3.
Wang et al. "Microwave Radiometric Thermoetry and Its Potential Applicability to Ablative Therapy", Journal of Interventional Cardiac Electrophysiology, 4(1): 295-300, Feb. 2000.

(56) References Cited

OTHER PUBLICATIONS

Wittkampf et al. "LocaLisa: New Technique for Real-Time 3-Dimensional Localization of Regular Intracardiac Electrodes", Circulation, 99(10): 1312-1317, Mar. 16, 1999.
Zhong et al. "On the Accuracy of CartoMerge for Guiding Posterior Left Atrial Ablation in Man", Heart Rhythm, 4(5): 595-602, Published Online Feb. 9, 2007.
Notice of Allowance dated Mar. 9, 2020 from the US Patent and Trademark Office Re. U.S. Appl. No. 16/349,648. (28 pages).
International Preliminary Report on Patentability dated May 31, 2019 From the International Bureau of WIPO Re. Application No. PCT/IB2017/057169. (9 Pages).
International Preliminary Report on Patentability dated May 31, 2019 From the International Bureau of WIPO Re. Application No. PCT/IB2017/057175. (9 Pages).
International Preliminary Report on Patentability dated May 31, 2019 From the International Bureau of WIPO Re. Application No. PCT/IB2017/057176. (10 Pages).
International Search Report and the Written Opinion dated Jun. 7, 2018 From the International Searching Authority Re. Application No. PCT/IB2018/050289. (16 Pages).
International Search Report and the Written Opinion dated Sep. 25, 2018 From the International Searching Authority Re. Application No. PCT/IB2018/050784. (18 Pages).
Invitation to Pay Additional Fees, Communication Relating to the Results of the Partial International Search and the Provisional Opinion dated Jun. 26, 2018 From the International Searching Authority Re. Application No. PCT/IB2018/050784. (13 Pages).
Boston Scientific "Rhythmia™ Mapping System: Rhythmia Disposables Product Information: Intellamap Orion™ High Resolution Mapping Catheter", Boston Scientific, 2 P., Sep. 2015.
Third-Party Submission under 37 CFR 1.290 filed on Mar. 2, 2021 from the US Patent and Trademark Office Re. U.S. Appl. No. 16/349,646. (2 Pages).
USPTO Communication dated Mar. 5, 2021 Re Third-Party Submission from the US Patent and Trademark Office Re. U.S. Appl. No. 16/349,646.(2 Pages).

* cited by examiner

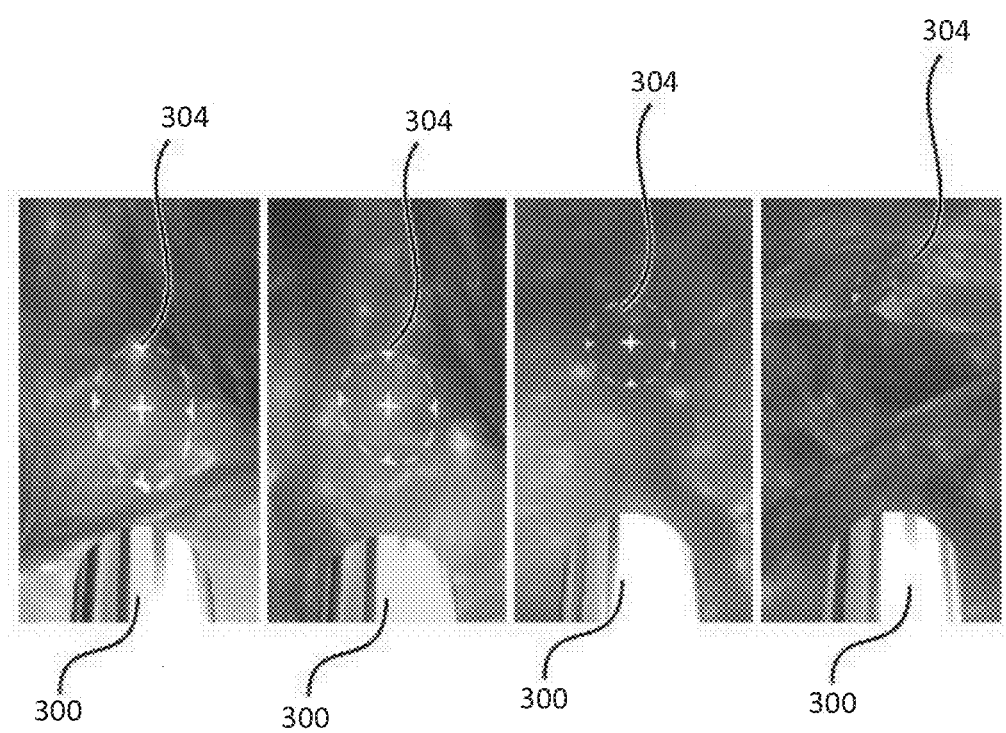

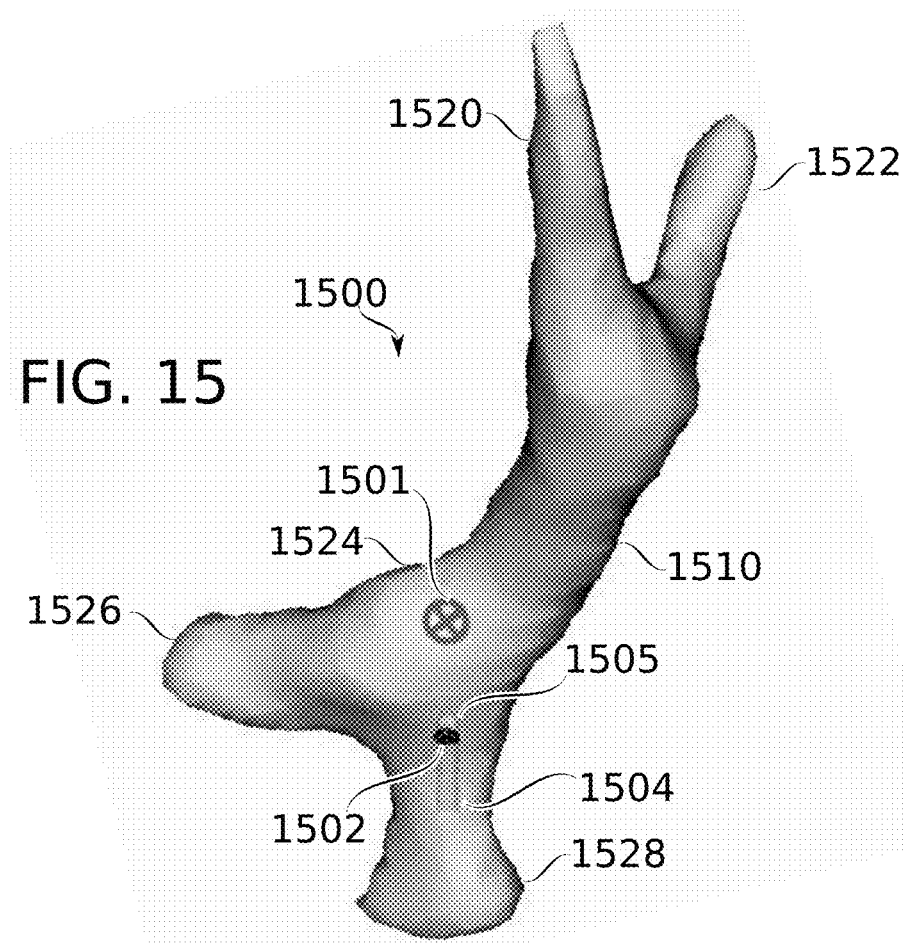

TISSUE MODEL DYNAMIC VISUAL RENDERING

RELATED APPLICATIONS

This application is a National Phase of PCT Patent Application No. PCT/IB2017/057169 having International filing date of Nov. 16, 2017, which claims the benefit of priority under 35 USC § 119(e) of U.S. Provisional Patent Application No. 62/422,708 filed on 16 Nov. 2016, U.S. Provisional Patent Application No. 62/422,705 filed on 16 Nov. 2016 and U.S. Provisional Patent Application No. 62/422,713 filed on 16 Nov. 2016. The contents of the above applications are all incorporated by reference as if fully set forth herein in their entirety.

FIELD AND BACKGROUND OF THE INVENTION

The present invention, in some embodiments thereof, relates to systems and/or methods for assisting a surgeon in catheterization procedures, more particularly, but not exclusively, to such system and/or methods that make use of dynamic visual representations.

U.S. Patent Application Publication No. 2003/074011 discloses "A method of displaying at least one point-of-interest of a body during an intra-body medical procedure. The method is effected by (a) establishing a location of the body; (b) establishing a location of an imaging instrument being for imaging at least a portion of the body; (c) defining at least one projection plane being in relation to a projection plane of the imaging instrument; (d) acquiring at least one point-of-interest of the body; and (e) projecting said at least one point-of-interest on said at least one projection plane; such that, in course of the procedure, the locations of the body and the imaging instrument are known, thereby the at least one point-of-interest is projectable on the at least one projection plane even in cases whereby a relative location of the body and the imaging instrument are changed."

SUMMARY OF THE INVENTION

There is provided, in accordance with some embodiments of the present disclosure, a method of graphically presenting an indicating marker over a 3-D model of a tissue surface during a catheterization procedure using a catheter probe, the method comprising: determining a region over the 3-D model; deforming the indicating marker to obtain a deformed indicating marker that congruently matches a shape defined by the 3-D model across the region at a plurality of positions; and rendering the 3-D model into an image including the deformed indicating marker by generating an image of the 3-D model covered by the deformed indicating marker across the region defined by the plurality of positions.

In some embodiments, the indicating marker indicates a field of view viewed from a location along the catheter probe, the location being determined by a measured position and facing direction of a distal end of the catheter probe.

In some embodiments, an appearance of the indicating marker indicates a relative location of the catheter probe with respect to the tissue surface, the relative location being determined based on a measured position and facing direction of a distal end of the catheter probe relative to the tissue surface.

In some embodiments, a size of the region indicates a distance between the catheter probe and the tissue surface.

In some embodiments, a visibility of the indicating marker indicates a distance between the catheter probe and the tissue surface.

In some embodiments, an aspect ratio of the region indicates an orientation between the catheter probe and the tissue surface.

In some embodiments, the determining, the deforming and the rendering are performed iteratively for at least a portion of a duration of the catheterization procedure.

In some embodiments, the presenting is updated at a frame rate of 10 frames per second or more.

In some embodiments, the indicating marker indicates a planned path.

In some embodiments, the indicating marker points in a direction of a selected target site.

In some embodiments, the method further comprises identifying the indicating marker should be presented, the identifying is based on rules pre-associated with input expected to be acquired during the catheterization procedure.

In some embodiments, the input comprises an identified onset of a catheter probe navigation process.

In some embodiments, the input comprises an identified onset of an ablation.

There is provided, in accordance with some embodiments of the present disclosure, a method of graphically presenting a 3-D model of a tissue region during a catheterization procedure, the method comprising: estimating an estimated effect of the catheterization procedure on the tissue region; calculating, based on the estimated effect, a shape, a size, and a position of a region to be marked on the 3-D model; selecting at least one material appearance property based on the estimated effect; and rendering the 3-D model to present the estimated effect using the assigned material appearance properties across the region to be marked.

In some embodiments, the estimated effect comprises at least one of an estimated change in temperature, an estimated change in shape and an estimated change in size of the tissue region.

In some embodiments, the calculating a shape comprises calculating an area of an ablation point.

In some embodiments, the calculating a shape comprises calculating a depth of an ablation point.

In some embodiments, the calculating a shape includes calculating a path of a plurality of ablation points.

In some embodiments, the material appearance properties are selected to visualize a state of the tissue.

In some embodiments, the material appearance properties comprise a change in at least one of the group consisting of reflectance, absorption, scattering, translucency, texture and any combination thereof.

In some embodiments, the estimating comprises presenting the estimated effect as a function of time.

In some embodiments, the shape is recalculated as a function of time.

In some embodiments, the shape and the material appearance properties indicate an increasing spread of a lesioning effect.

There is provided, in accordance with some embodiments of the present disclosure, a method of visually rendering a 3-D model of a tissue region to indicate a position and a facing direction of a catheter probe during a catheterization procedure, the method comprising: determining the position and facing direction of a distal end of the catheter probe with respect to the tissue region; and rendering the 3-D model to include a simulation of a first indicating mark, the first indicating mark being simulated in a position of a surface portion defined by the 3-D model, wherein the position is also located along an axis extending distally from the determined position and in the determined facing direction of the distal end of the catheter.

In some embodiments, the method further comprises rendering the 3-D model to include a simulation of a second indicating mark, the second indicating mark being simulated in a position of a second surface portion defined by the 3-D model, wherein second surface portion occupies a closest surface position of the 3-D model to a predefined portion of the distal end of the catheter.

In some embodiments, the first indicating mark and the second indicating mark are rendered together as a single indicating mark when the determined position of the distal end indicates contact with a surface defined by the 3-D model.

In some embodiments, at least one of the indicating marks is shaped and positioned to congruently match the corresponding 3-D model surface portion.

In some embodiments, the 3-D model is rendered as viewed from a viewpoint from outside an organ comprising the tissue region.

In some embodiments, the 3-D model is rendered as viewed from a viewpoint from within an organ comprising the tissue region.

In some embodiments, the tissue region comprises a body lumen.

In some embodiments, the 3-D model is rendered as viewed from a viewpoint offset to the distal end of the catheter probe.

In some embodiments, the determining and the rendering is provided iteratively during at least a portion of the catheterization procedure.

In some embodiments, the method further comprises simultaneously presenting two or more views of the 3-D model, each viewed from a different viewpoint, the different viewpoints comprising a first viewpoint being inside an organ comprising the tissue region and a second viewpoint being outside the organ.

In some embodiments, both presentations include the first indicating mark.

In some embodiments, at least one of indicating marks is simulated as an illumination of the 3-D model surface.

In some embodiments, the illumination is simulated to be uneven across a simulated illumination beam.

In some embodiments, a center of the illumination is calculated according to a position and facing direction of the catheter probe relative to the tissue region.

In some embodiments, the center of illumination is graphically presented by increased illumination intensity at a center of the beam.

In some embodiments, the method further comprises simulating a second illumination source illuminating from a position distinct from the position of the distal end of the catheter probe.

In some embodiments, the method further comprises simulating a second illumination source, illuminating in a direction distinct from the facing direction of the distal end of the catheter probe.

In some embodiments, the second illumination source is simulated as an ambient light source.

In some embodiments, the rendering comprises selecting a material appearance of a surface of the tissue region, the material appearance is simulated to be affected by the illumination.

In some embodiments, the rendering comprises rendering the tissue region as at least partially translucent to the simulated illumination.

There is provided, in accordance with some embodiments of the present disclosure, a method of automatically modifying an image presenting a 3-D model of a tissue region during a catheterization procedure, the method comprising: associating each of a plurality of conditions with a corresponding image presenting the 3-D model; identifying an onset of one condition of the plurality of conditions; automatically displaying the image associated with the one condition in response to the identifying of the onset of the one condition.

In some embodiments, the condition comprises a distance between a distal end of a catheter probe and a tissue surface shorter than a pre-set threshold.

In some embodiments, the condition comprises the tissue surface including a target site.

In some embodiments, the condition comprises changing an operation state of a catheter probe.

In some embodiments, the condition comprises detecting a contact of a distal end of a catheter probe with a surface of the tissue region.

In some embodiments, the image comprises a view of a cross-section of a tissue depth.

In some embodiments, the image comprises a zoom in of the 3-D model.

In some embodiments, during the zoom in, an indicating marker is rendered across a region of the 3-D model.

In some embodiments, the image comprises a plurality of images of the 3-D model, each viewed from a distinct viewpoint.

There is provided, in accordance with some embodiments of the present disclosure, a method of rendering a model of a tissue surface of an inside environment of an organ presented during a catheterization procedure using a catheter probe, comprising: receiving data indicative of a position and a facing direction of a distal end of the catheter probe with respect to the tissue surface; and rendering the model to an image having a viewing location within the organ, and distinct from any position along the catheter probe.

In some embodiments, the rendering further comprises generating a graphical presentation of at least a portion of the distal end of the catheter probe.

In some embodiments, the distal end is presented at the position and facing the facing direction.

In some embodiments, the location is further away from the tissue surface than the distal end of the catheter probe.

In some embodiments, the method further comprises receiving an electrical reading from an electrode mounted on the catheter probe, the electrical reading indicating that a 3-D structure of the tissue surface has changed to a second structure.

In some embodiments, the method further comprises modifying the image to present the second structure of the tissue surface.

There is provided, in accordance with some embodiments of the present disclosure, a system for graphically presenting an indicating marker during a catheterization procedure, the system comprising computer circuitry configured to: receive a 3-D model of a body tissue region; determine a plurality of positions of the indicating marker relative to the 3-D model; and present an image of at least a portion of the 3-D model partially covered by the indicating marker deformed to congruently match the 3-D model at the determined position.

In some embodiments, the circuitry is configured to deform the indicating marker using a graphical game engine.

In some embodiments, the system further is configured to sense data indicative of a position and facing direction of a distal end of a catheter probe.

In some embodiments, the circuitry is configured to determine the plurality of positions according to the position and facing direction of the distal end of the catheter probe.

In some embodiments, the system comprises a display configured to display the presented image.

In some embodiments, the computer circuitry is configured to produce the 3-D model.

In some embodiments, the 3-D model is produced using data obtained from an intra-body probe.

In some embodiments, the 3-D model is produced using image data.

In some embodiments, the computer circuitry is configured to present the image with indications of use made of the treatment element during the catheterization procedure.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING (S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-1E are flow charts illustrating exemplary processes for rendering and modifying the visual presentation of a tissue model as described herein, in accordance with some embodiments of the invention, wherein FIG. 1A exemplifies a process for rendering a simulated indicating marker over a 3-D tissue model, FIG. 1B exemplifies a process for rendering a geometric tissue model based on estimated data, FIG. 1C exemplifies a process for providing a point of reference for a catheter by rendering a 3-D tissue model, FIG. 1D exemplifies a process for automatically modifying the image used to present a 3-D tissue model and FIG. 1E exemplifies a viewpoint used to render a 3-D model;

FIG. 2 is a flow chart illustrating an exemplary medical process which may benefit from using the visual rendering and display as described herein, in accordance with some embodiments of the invention;

FIGS. 3A-3D show the 3-D model as rendered from two exemplary viewpoint, together with a simulation of an illumination, in accordance with some embodiments of the invention, wherein FIG. 3A illustrates a shooter's view of the catheter facing a vein, FIG. 3B illustrates an out-of-organ view of the catheter position in FIG. 3A, FIG. 3C illustrates a shooter's view of the catheter facing an inner wall of the heart and FIG. 3D illustrates an out-of-organ view of the catheter position in FIG. 3C;

FIGS. 4A-4B show a simulation of the flashlight feature, in accordance with some embodiments of the invention, wherein FIG. 4A illustrates a shooter's view and FIG. 4B illustrates an out-of-organ view;

FIGS. 5A-5D show a simulation of a shape-specific indicating marker feature, in accordance with some embodiments of the invention, wherein FIG. 5A illustrates a projection over a first surface, FIG. 5B illustrates a projection over a second surface, FIG. 5C illustrates a projection over a third surface, FIG. 5D illustrates a projection over a forth surface;

Figure 6A:
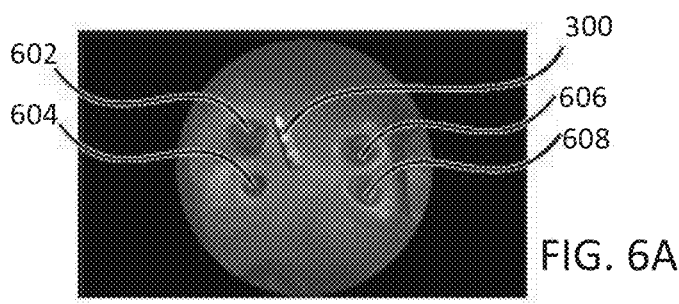
Figure 6B:
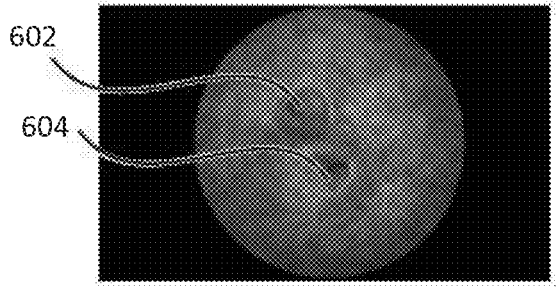
Figure 6C:
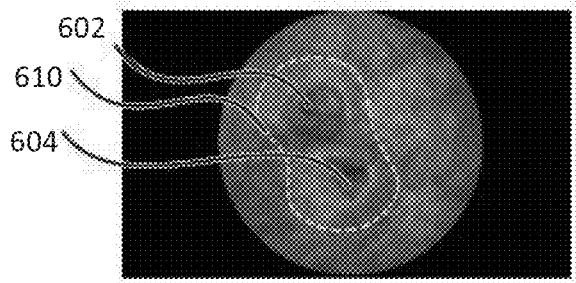
Figure 6D:
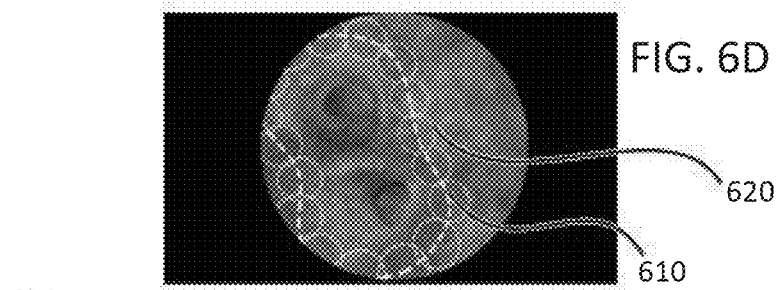
Figure 6E:
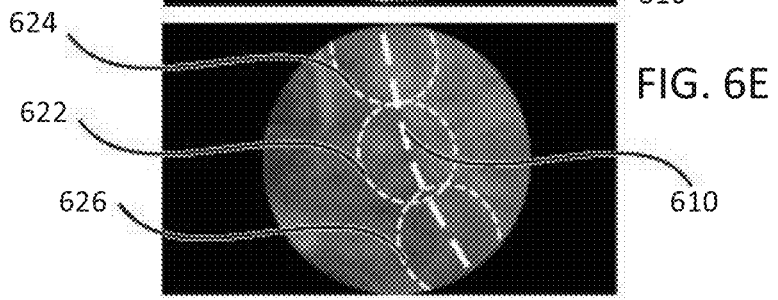
Figure 6F:
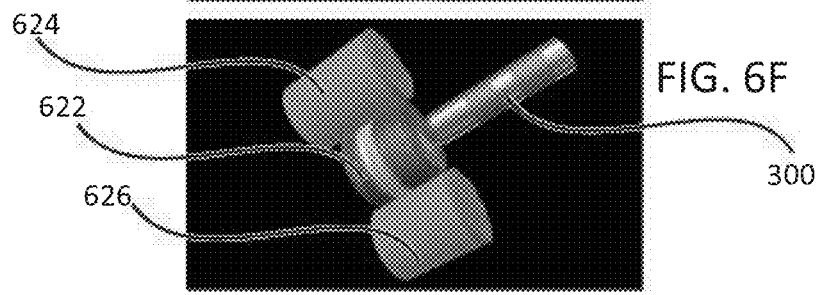
Figure 7A:
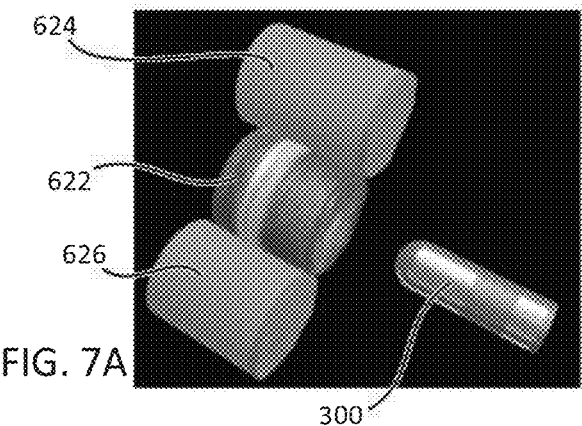
Figure 7B:
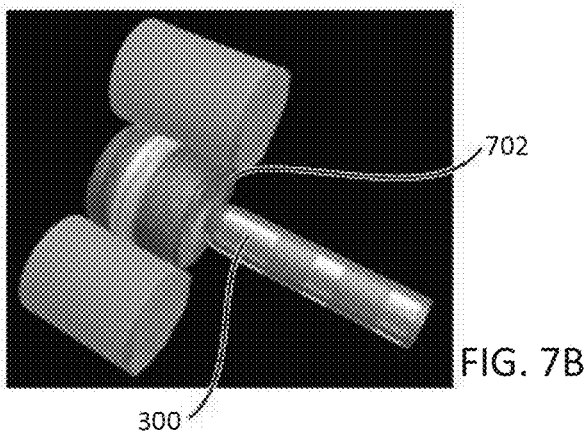
Figure 7C:
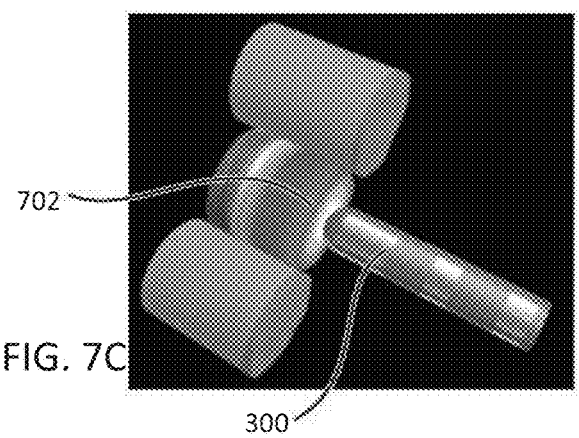
Figure 7D:
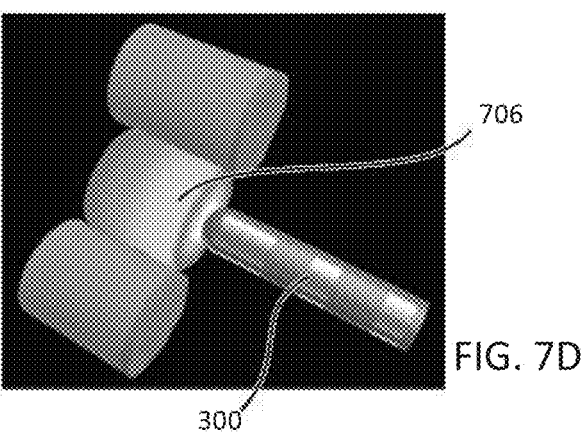
Figure 7E:
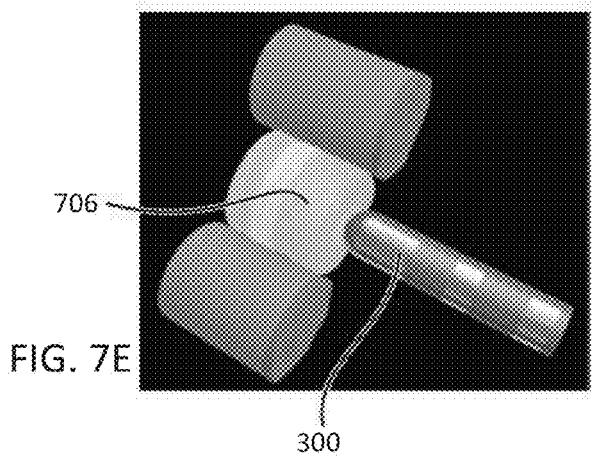
Figure 7F:
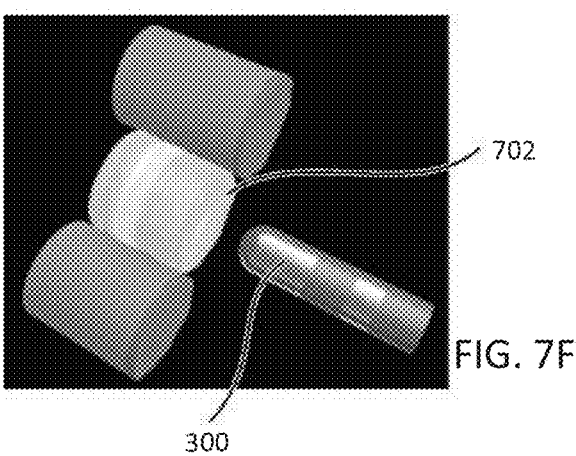
Figure 8:
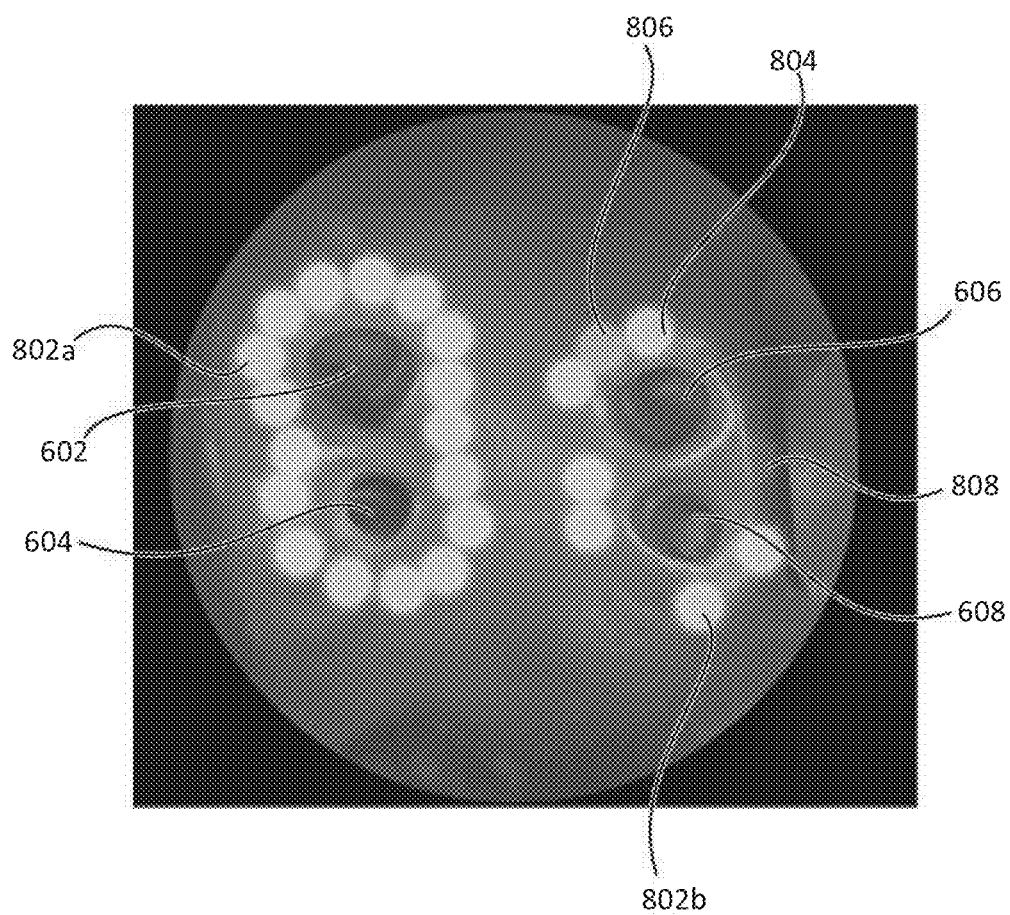
Figure 9A:
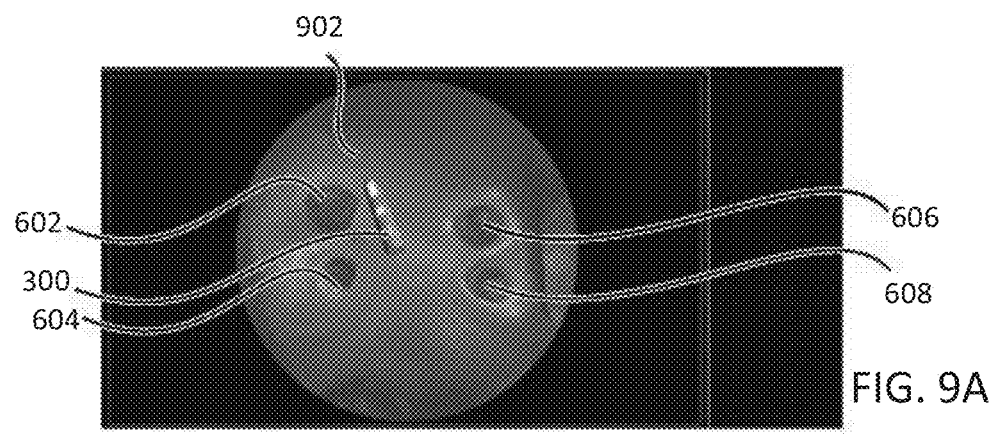
Figure 9B:
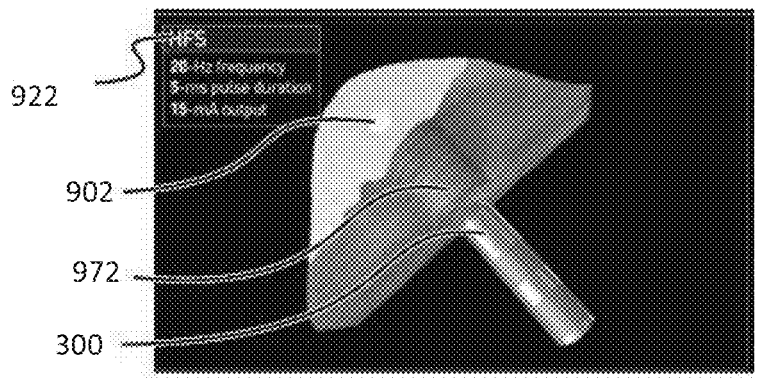
Figure 9C:
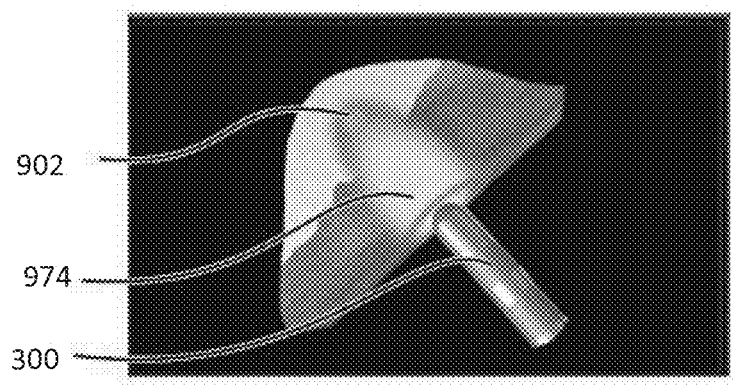
Figure 9D:
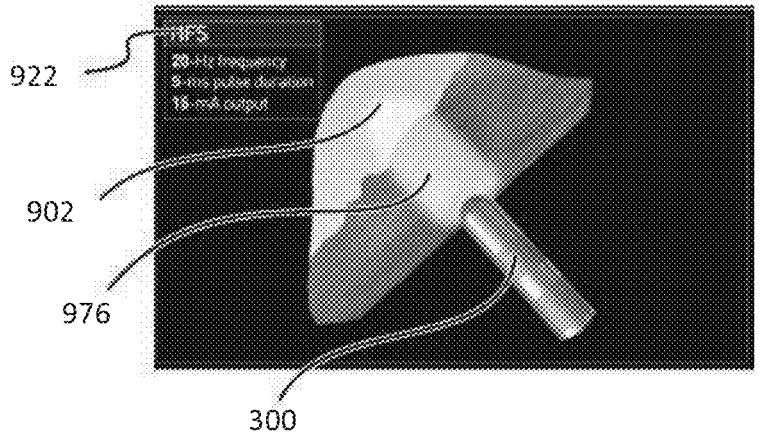
Figure 9E:
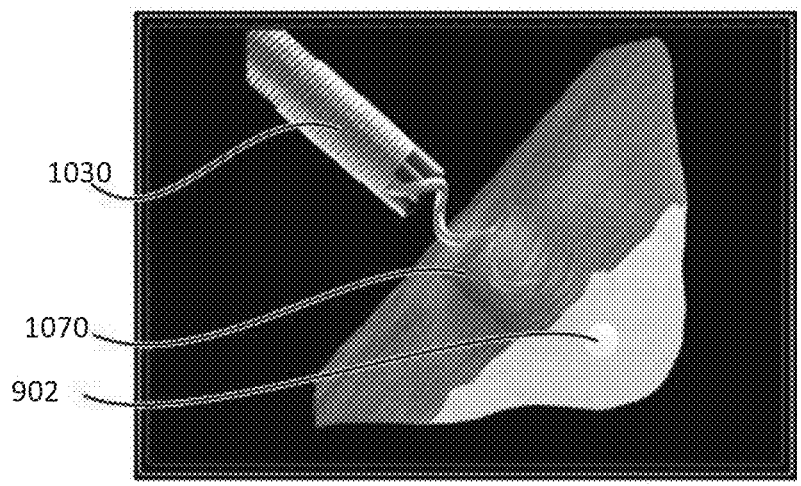
Figure 9F:
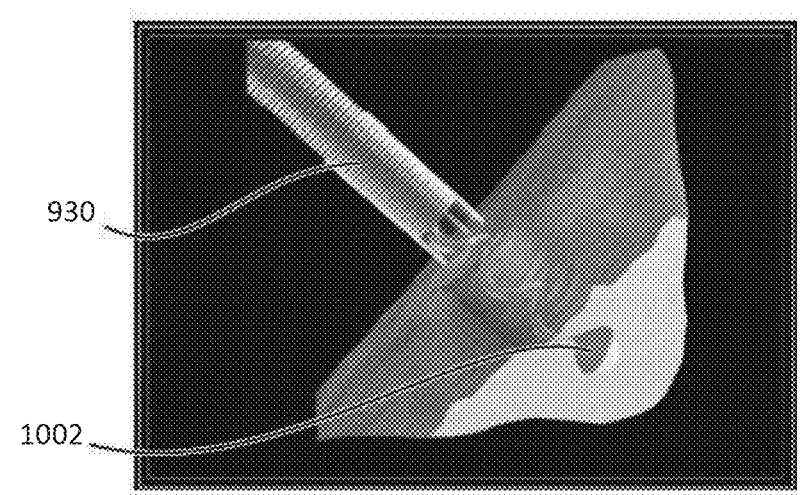
Figure 9G:
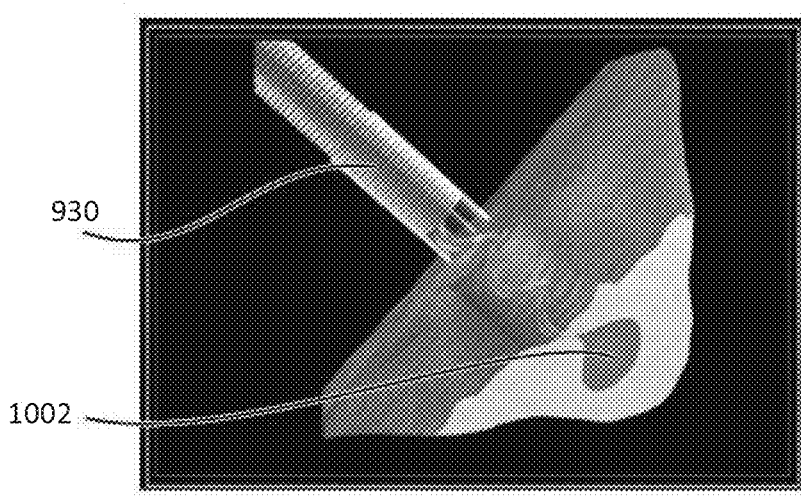
Figure 10A:
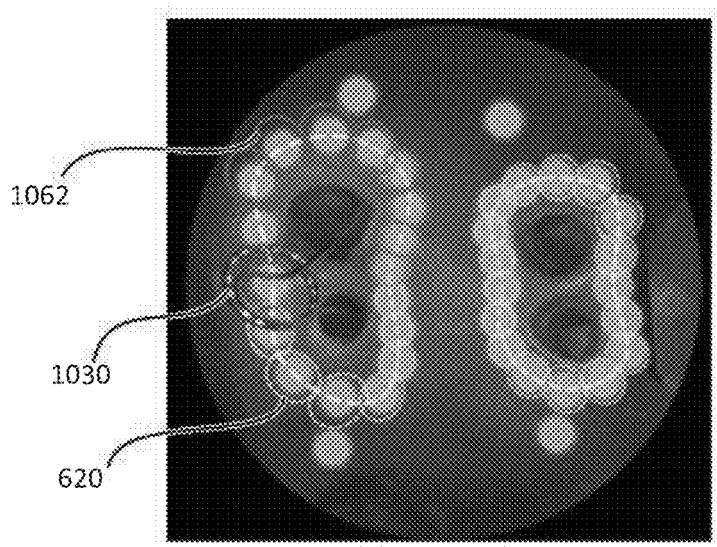
Figure 10B:
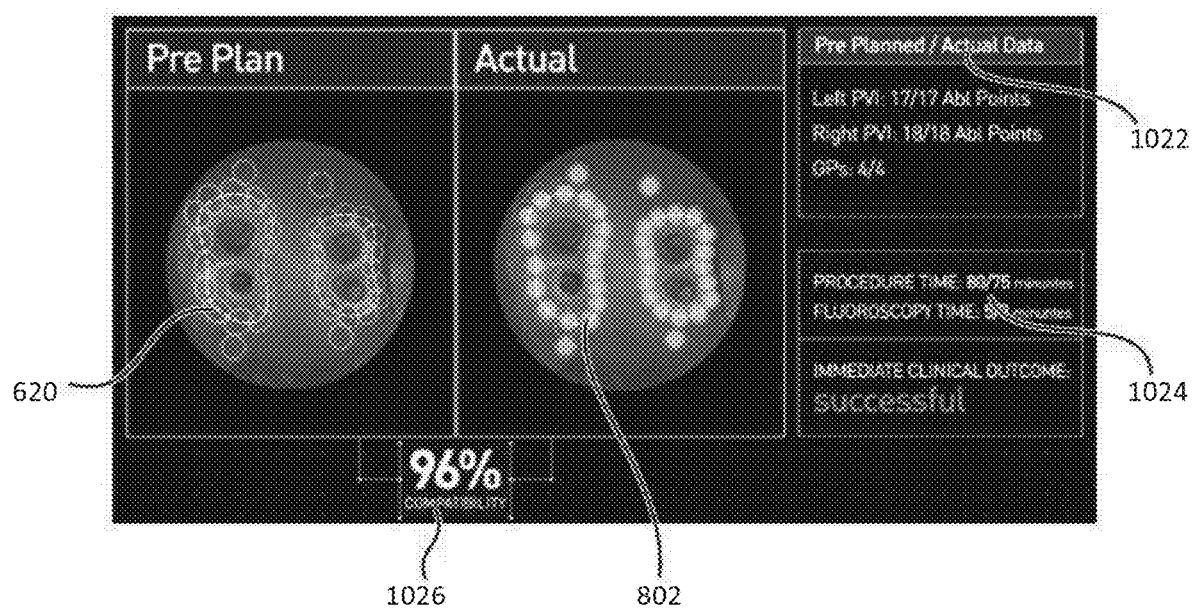
Figure 11:
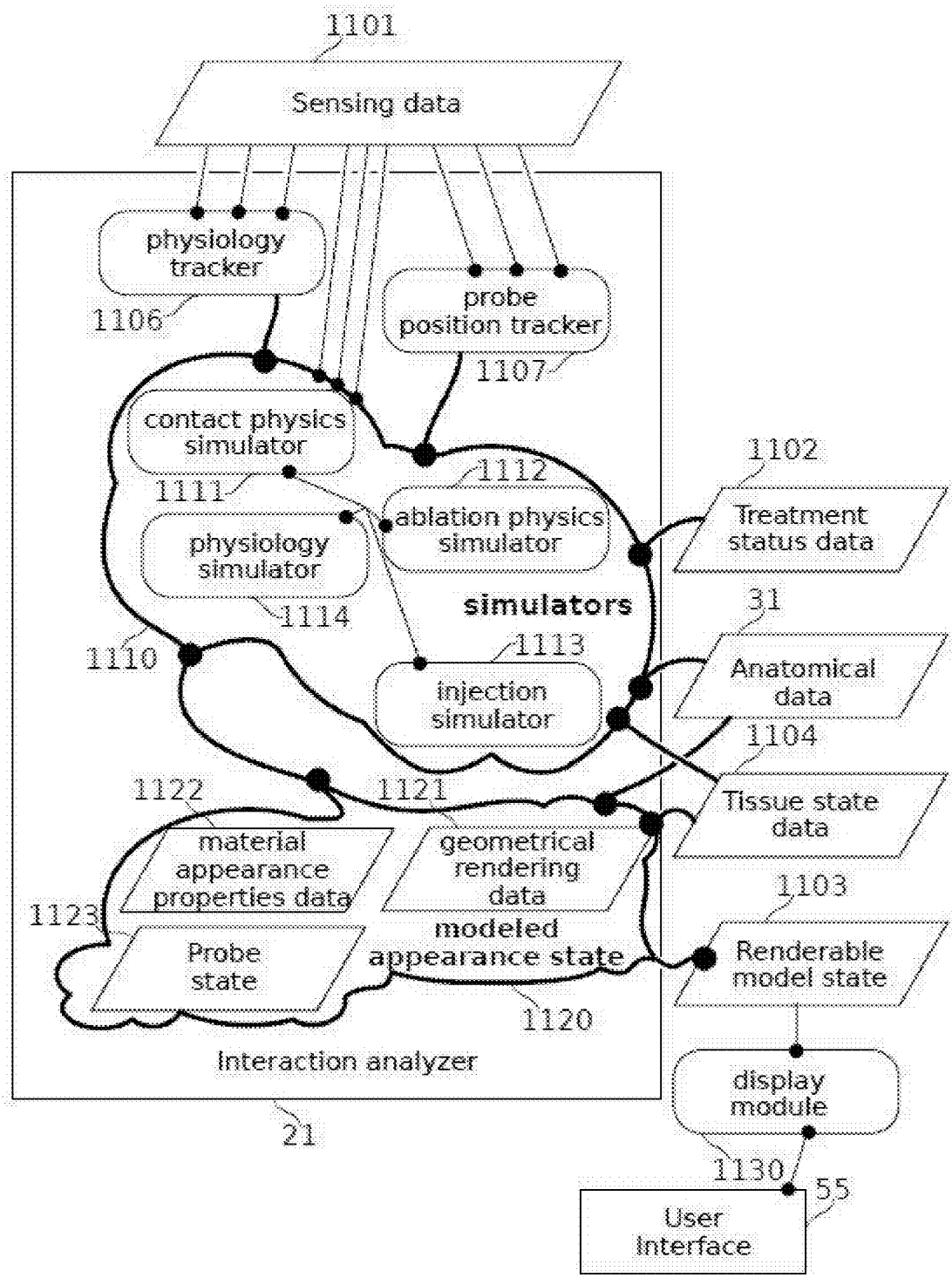
Figure 12:
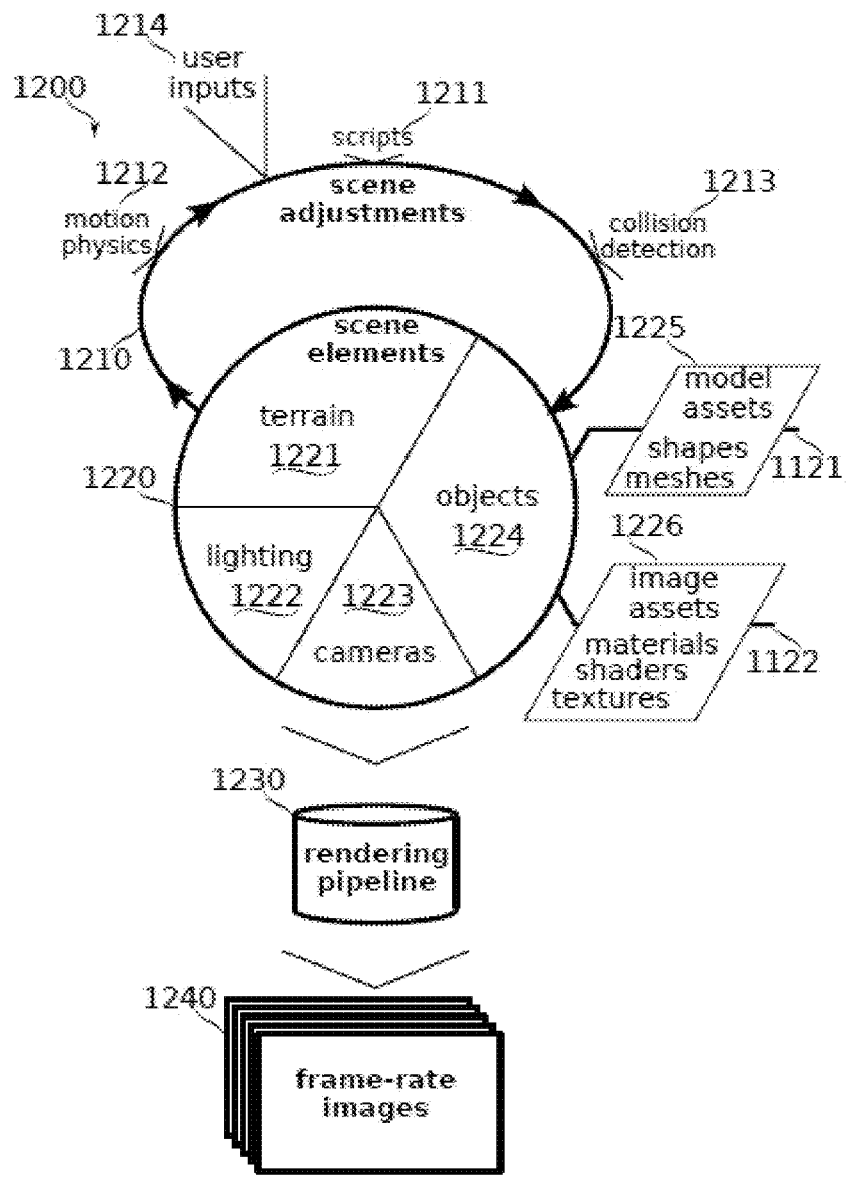
Figure 13:
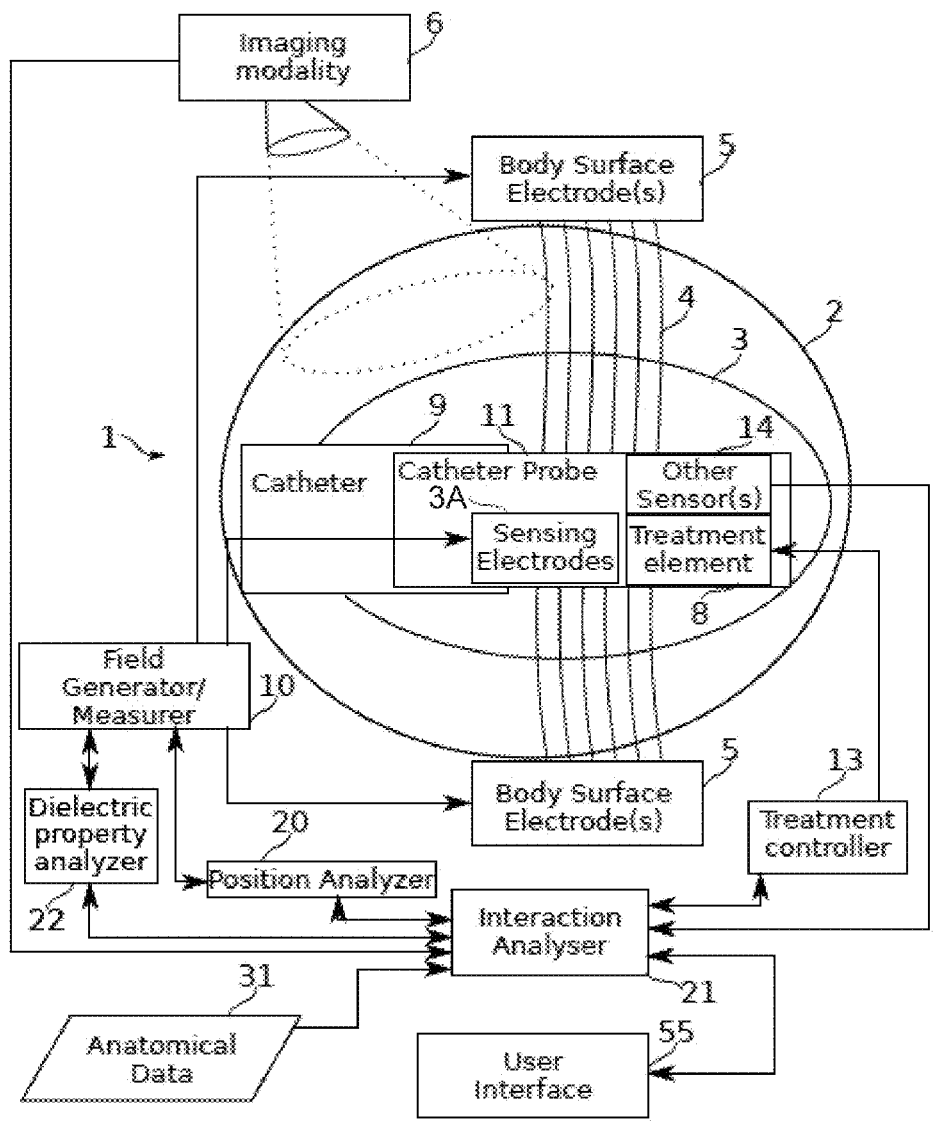
Figure 14A:
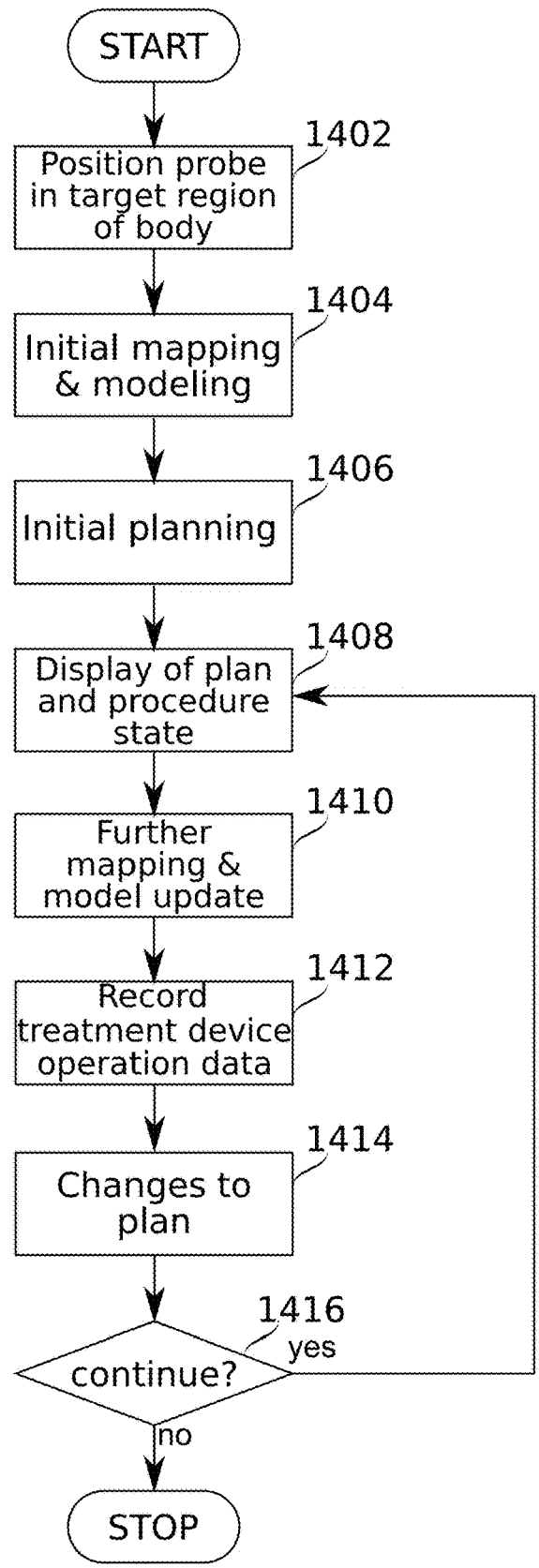
Figures 14B, 14C:
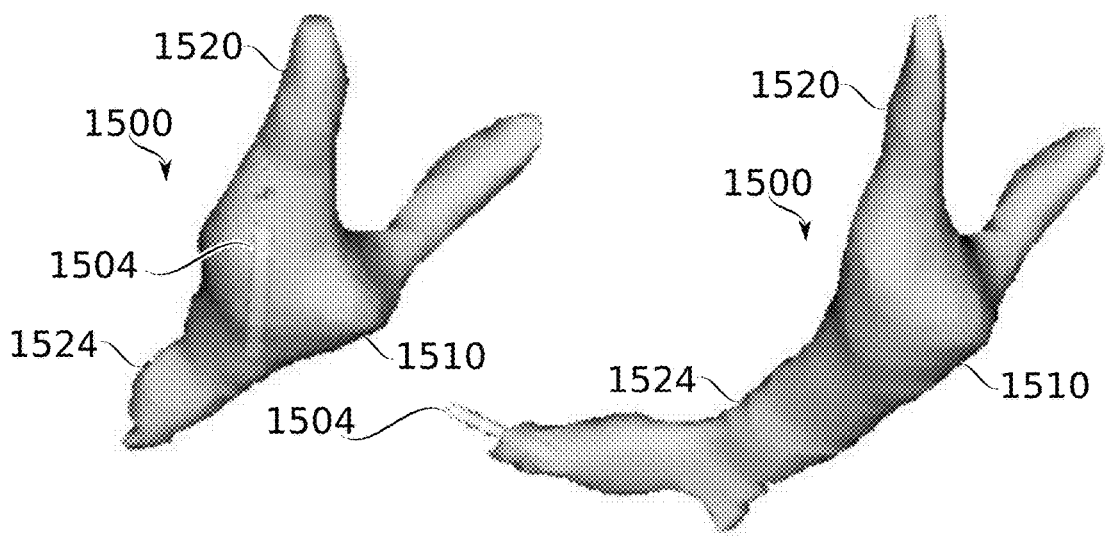
Figures 14D, 14E:
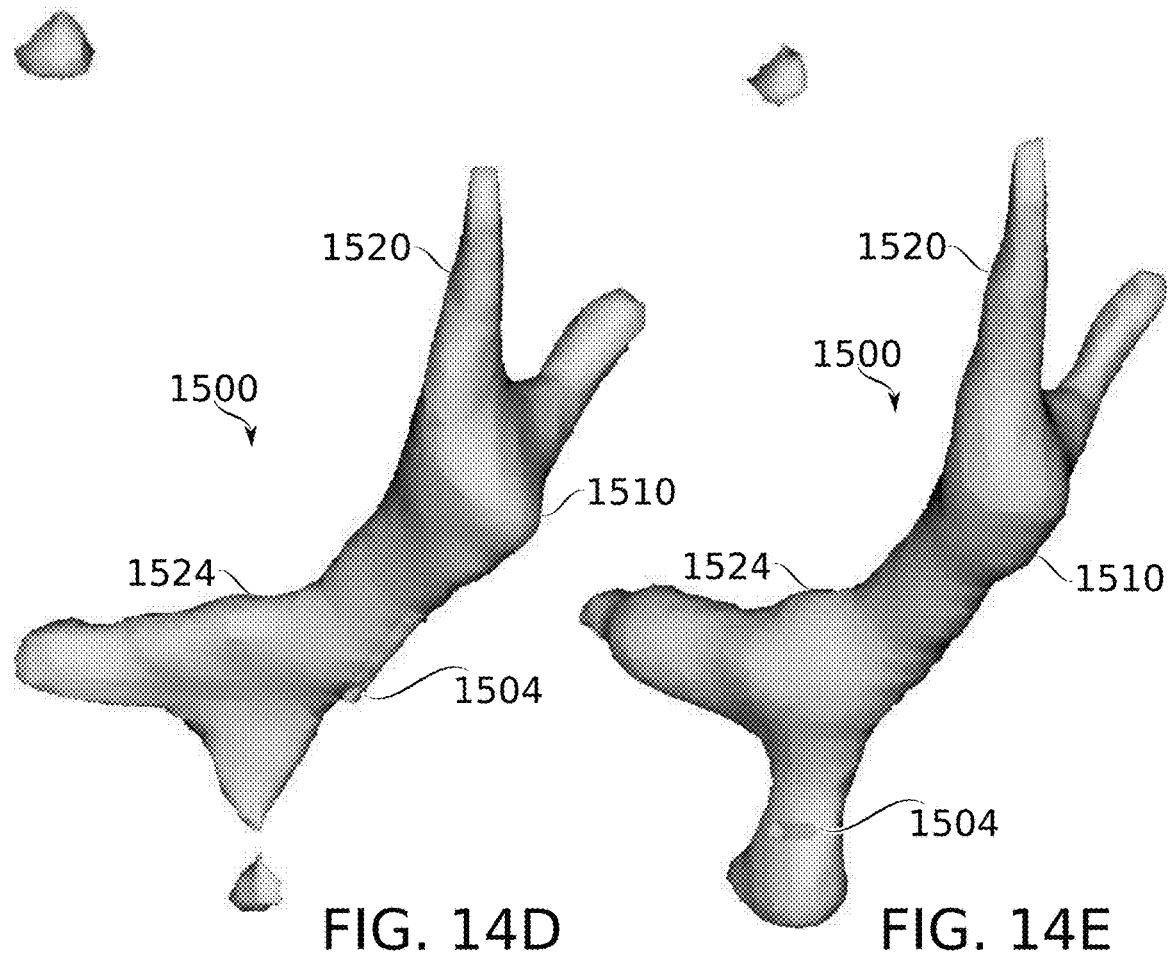

FIGS. 6A-6F show a simulation of identifying a target and starting an ablation, in accordance with some embodiments of the invention, wherein FIG. 6A shows a left atrium inner view, FIG. 6B shows left superior and inferior pulmonary veins, FIG. 6C exemplifies an identification of a planned ablation path, FIG. 6D exemplifies the appearance of details such as planned ablation sub-regions, FIG. 6E exemplifies directing a catheter towards a sub-region and FIG. 6F exemplifies shifting in points of view during an ablation process;

FIGS. 7A-7F exemplify a point of view of an ablation of a sub-region, in accordance with some embodiments of the invention, wherein FIG. 7A exemplifies a catheter approaching the targeted sub-region, FIG. 7B exemplifies the surface of the sub-region being pushed by the contact force of the catheter, FIG. 7C exemplifies tissue surface getting warm, FIG. 7D exemplifies a tissue depth getting warm, FIG. 7E exemplifies a tissue getting scarred and FIG. 7F exemplifies a catheter being withdrawn from the treated sub-region;

FIG. 8 exemplifies an ablation area overview simulation, in accordance with some embodiments of the invention; and FIGS. 9A-9G exemplify a sub-region elimination of a ganglion, wherein FIGS. 9A-9D exemplify a single sub-region ablation simulation showing ganglia ablation as an example, and FIGS. 9E-9G exemplify ganglion elimination by injecting an eliminating substance, in accordance with some embodiments of the invention, wherein FIG. 9A exemplifies identifying the target, FIG. 9B exemplifies contacting the target, FIG. 9C exemplifies tissue heating and FIG. 9D exemplifies scar formation and wherein FIG. 9E exemplifies injector penetration into the target, FIG. 9F exemplifies initial injection stage and FIG. 9G exemplifies advanced injection stage;

FIGS. 10A-10B exemplify validation processes, in accordance with some embodiments of the invention, wherein FIG. 10A exemplifies a simulation of a validation procedure, and FIG. 10B exemplifies an overview of a pre made plan when compared to the actual procedure;

FIG. 11 schematically represents software components and data structures comprised in and/or used by an interaction analyzer of a display system, according to some embodiments of the present disclosure;

FIG. 12 schematically represents components, inputs, and outputs of a graphical game engine operating to manage and render scene elements to motion frame-rate images, according to some embodiments of the present disclosure; and FIG. 13 is a schematic representation of a display system configured for display of interactions between a catheter probe and a body tissue region, and/or their effects, according to some embodiments of the present disclosure;

FIG. 14A is a flow chart schematically describing a cardiac ablation procedure, wherein indicating marks are placed on a 3-D model which is developed from data obtained during the procedure itself, according to some embodiments of the present disclosure;

FIGS. 14B-14E show a phase of iterative intra-procedure reconstruction of a model of a right atrium and connecting blood vessels including the superior vena cava and inferior vena cava, according to some embodiments of the present disclosure; and FIG. 15 illustrates use of indicating marks for showing a current position of a tip of a probe positioned within a 3-D model of a body lumen, according to some embodiments of the present disclosure.

DESCRIPTION OF SPECIFIC EMBODIMENTS OF THE INVENTION

The present invention, in some embodiments thereof, relates to systems and/or methods for assisting a surgeon in catheterization procedures, more particularly, but not exclusively, to such system and/or methods that make use of dynamic visual representations.

Overview

An aspect of some embodiments of the invention relates to a user interface for assisting in medical procedures, guiding a surgeon by updating the appearance and/or images used to render a 3-D model of a tissue, optionally based on a catheter probe's position and/or operation with respect to the modeled tissue.

In some embodiments, a user interface is configured to display an indicating marker deformed to match a 3-D model of a tissue surface, optionally during a catheterization process. In some embodiments, the indicating marker marks a portion of the field of view viewed from a location along a catheter probe. Optionally, a graphical object is assigned to the indicating marker. For example, a marker for marking an ablation site may be assigned a graphical object with defined visual appearance properties, such as shape, color, texture, etc. In some embodiments, the graphical object is rendered across a region of the 3-D model, the object being deformed to congruently match the 3-D geometric surface of the model. In some embodiments, congruent matching comprises deforming the graphical object to match the 3-D model at a plurality of positions across a determined region to be marked.

As used herein, the term indicating marker is any graphical object included in an image, for use as a visual indicator of measured and/or calculated and/or estimated data. For example, an indicating marker may be an icon indicative of a measured position and/or orientation of a catheter probe. In another example, an indicating marker may be a marking representative of calculated heat dissipation based on ablation parameters. In yet another example, an indicating marker may be an indicative visual sign (e.g., an icon) indicative of an estimated effect of an ablation procedure, such as estimated scarring.

In some embodiments, a graphical object comprises an icon, and/or a symbol, and/or a character, and/or a picture, and/or sign, and/or visual indicator, and/or a marker. Optionally, an indicating marker includes a delimitation of a region across the 3-D model. In some embodiments, the 3-D model is rendered across the delimited region to visually represent a modified appearance. Alternatively or additionally, the indicating marker is congruently matched to the 3-D shape of the model, resulting in a patient-specific marker.

The term simulation and its inflections (e.g., simulated, simulating, etc.) refers herein to imitation of the operation of a tissue or organ of a patient during a catheterization procedure. The act of simulating the tissue or organ is based on a model. The model may include a structural model (e.g., a 3-D anatomical model) and a functional model. The functional model may supply rules for the changes occurring in the 3-D anatomical model over time under conventional conditions, and under the conditions that may evolve during the procedure. The simulation may be represented by a motion frame-rate, real-time display, showing graphical images that change over time in manners indicative to the changes that the tissue or organ undergo at the time of display. The display and/or conditions that evolve during the catheterization process may be recorded to allow replaying the simulation also off-line, e.g., after the procedure is over, for example, for studying how to run similar procedures to gain similar or better results.

In some embodiments, the modeled tissue is an inner environment of an organ of a patient, possibly a lumen. In some embodiments, the organ is a heart and optionally the lumen is a vein and/or artery of the heart. Alternatively or additionally, the lumen is an atrium and/or a ventricle. Alternatively or additionally, the modeled tissue comprises an outer form of a patient's organ. In some embodiments, a 3-D model is obtained based on imaging data acquired from the patient, for example, such as imaging acquired by magnetic resonance imaging (MRI), and/or computed tomography (CT), and/or by ultrasound (US) and/or by nuclear medicine (NM). Alternatively or additionally, data is acquired by measuring thermal and/or dielectric tissue properties. Optionally, an initial 3-D model of the tissue is provided by presenting a mesh of a plurality of data inputs. In some embodiments, the catheterization procedure includes navigation of the catheter probe inside the patient's body and/or organ. Alternatively or additionally, the catheterization procedure includes an ablation process. Alternatively or additionally, the catheterization procedure includes planning (optionally, preplanning; that is, planning in advance of catheterization itself) of an ablation process.

In some embodiments, rendering the 3-D model into an image including the deformed indicating marker is provided by generating an image of the 3-D model covered by the deformed indicating marker across the region defined by the determined plurality of positions. In some embodiments, generating an image covered by the indicating marker includes blending in the indicating marker with the rendered image of the 3-D model. Alternatively or additionally, generating an image covered by the indicating marker includes rendering the indicating marker just below a surface of the modeled tissue, shown by rendering the surface at least partially transparent.

In some embodiments, the viewpoint used to render the 3-D model is offset to the viewpoint indicated by the indicating marker. For example, when the indicating marker signifies a viewpoint located along the catheter probe, the viewpoint used to render the 3-D model may be offset to the location of the catheter probe, as if viewed by a "third person". Optionally, the field of view of the "third person" can include both the indicating marker and at least a portion of the distal end of the catheter probe, i.e. the end inside a region of the patient comprising one or more target sites.

In some embodiments, the region used to render the indicating marker across the 3-D model is at least partially determined based on data inputs from one or more measurement sources active during the catheterization procedure. In some embodiments, the rendered region is based on a simulated projection of the graphical object onto the modeled tissue surface from a viewpoint location. Optionally, the viewpoint location is determined as being offset to a measured and/or estimated and/or calculated position and/or facing direction (for example, a distal direction along a longitudinal axis of a distal portion of the probe) and/or orientation of a catheter probe. Optionally, the viewpoint location is determined to be further away from a distal end of the catheter, with respect to the tissue it is facing.

Optionally, a position and/or facing direction and/or orientation of the catheter probe are determined relative to the modeled tissue. Alternatively or additionally, a stationary environment, such as a room and/or a procedure venue, is used to determine the position and/or facing direction and/or orientation of the catheter probe. Optionally, position and/or facing direction and/or orientation of the distal end of the catheter probe are determined.

In some embodiments, the appearance of the graphical object is indicative to the spatial relations between the catheter probe and the tissue surface. Optionally, the appearance includes size, and/or aspect ratio, and/or visibility, and/or color and/or transparency and/or reflectance. In some embodiments, spatial relations are expressed by distance, and/or relative tilting angle.

In some embodiments, the appearance of the graphical object may depend on the location and/or orientation of the catheter probe in respect to the tissue surface, so that a surgeon may infer the location and/or orientation from the appearance of the graphical object. For example, in some embodiments the size of the region to be marked is indicative to a measured and/or estimated distance between the catheter probe, optionally its distal end, and the tissue surface.

For example, a shorter distance may be indicated by a larger region size and/or a larger distance may be indicated by a smaller region size. A potential advantage of a region size being anti-correlated to the distance is that a shorter distance is usually intuitively perceived by objects seeming larger than when viewed from a larger distance. Alternatively or additionally, the shape of the region is indicative of the relative orientation of the probe to the tissue surface. Optionally, the relative orientation of the catheter probe to the tissue surface is defined by the angle between the facing direction of the catheter and the mean direction of the tissue surface it is facing. In some embodiments, a stretching degree of the graphical object is indicative of the relative orientation. For example, a non-stretched graphical object (e.g., of aspect ratio of about 1) may be indicative of perpendicularity between the probe and the tissue surface, while stretched graphical object may be indicative to the catheter probe being substantially parallel to the wall, for example, when the catheter extends along a lumen.

In some embodiments, the visibility of the graphical object corresponds to the position and/or facing direction of the catheter probe. In some embodiments, visibility relates to the intensity level and/or contrast and/or sharpness of the presented graphical object. For example, when the graphical object is simulated to be projected on a tissue wall, the intensity level of the visibility of the graphical object may correspond to the distance between the tissue wall and the catheter probe, optionally, determined by a distance between the mean surface of the tissue wall and the distal end of the catheter probe.

Optionally, determining the region to be marked, the deformation of the graphical object across that region and the rendering of the model in that region are provided iteratively during at least a portion of the duration of the catheterization procedure. For example, the appearance and/or size of the graphical object may change during the procedure according to changes in the spatial relationship between the catheter probe and the tissue surface.

In another example, real-time measurements of heat dissipation throughout the tissue may modify the size and/or shape of the region to be marked, and accordingly the deformation of the graphical object across the modified region. Alternatively, heat dissipation is estimated rather than measured. In some embodiments, determining the region to be marked, the deformation of the graphical object across that region and the rendering of the model in that region are presented as a function of time, according to estimated effects. For example, once an ablation has been performed, an effect of tissue heating, followed by tissue cooling and/or scaring is estimated, and this estimated effect may be presented as a function of time from the onset and/or completion of the ablation.

Alternatively or additionally, during the procedure it is identified that an indicating marker should be presented, possibly by identifying pre-set rules. For example, some indicating markers may be pre-set to appear only during navigation inside the heart, so when the catheter probe enters the heart it may be identified that such an indicating marker is to be presented, and when the catheter probe exits from the heart, such an indicating marker disappears. For example, in some embodiments, the indicating marker may be pre-associated with detecting an onset of a navigation process of the catheter probe, and may be presented to the surgeon only during detected navigation.

In some embodiments, rules that identify that a certain indicating marker is to be presented are pre-associated with input expected to be acquired during the catheterization procedure, for example, input indicative of the catheter being navigated, approaching a wall, ablating tissue, etc. In some embodiments, the input pre-associated with the presentation of an indicating marker is dynamically acquired during the catheterization procedure, so that, for example, when navigation ends, a marker that is to be presented only during navigation will disappear. In some embodiments, rules are limited to be associated with position and/or facing direction and/or operation status of a catheter probe.

In some embodiments, input pre-associated with presenting the indicating marker comprises an onset of an ablation.

Optionally, detecting an ablation onset may be associated with presenting a graphical object, and/or with removing the visual presentation of the graphical object. In some embodiments, ablation sites are marked based on planned data of target sites, optionally by visually representing a planned ablation path and/or ablation marks. In some embodiments, when detecting an ablation onset, and/or when identifying navigation in proximity to an ablation target site, at least one graphical object is rendered across a region in the 3-D model.

Optionally, a plurality of graphical objects represent ablation sites.

An aspect of several embodiments of the invention relates to rendering an appearance of a 3-D model based on an estimated effect of a catheterization procedure. In some embodiments, an estimated effect may include, for example, tissue heating, cooling, and/or swelling; and/or the degree of tissue heating and/or tissue cooling and/or tissue swelling. In some embodiments, a region to be marked on the 3-D model is determined based on the estimated effect, optionally, by estimating a shape, and/or a size and/or a position of the effect across the 3-D model.

In some embodiments, the estimated effect-adjusted appearance of the 3-D model is rendered only in a region to be marked. Optionally, rendering an appearance of the 3-D model comprises selecting at least one material appearance property (MAP), optionally from a database. In some embodiments, rendering the appearance includes rendering for visual display an image of the 3-D surface defined by the 3-D model. A potential advantage of manipulating the appearance of the surface of the 3-D model is a quicker-to-understand, more intuitive and/or more easily interpreted presentation of the presented data, as compared, for example, to tagging using icons which do not conform to the modeled shape. Close into a display used by an operator to guide an intrabody probe, and/or to improve the accuracy and/or precision with which actions by and/or through the probe (e.g., contacts and/or treatment administration) are associated to positions on the heart wall.

There is also a potential for reduction of error and/or ambiguity, and/or increase in accuracy in navigating of an intra-body probe with respect to a target indicated by a surface-conforming mark (for example, a mark which is implemented by changing the appearance of the surface of a portion of the 3-D model). Insofar as the surface mark and the surface state indications are rendered onto the same surface (e.g., rather than one floating above or otherwise ambiguously related to the other), it is potentially possible to make fine distinctions as to the need for an adjustment, and/or the adjustment to be made: e.g., to judge and/or select more precisely a degree of overlap between adjacent existing, planned, and/or selected lesion sites.

Optionally, a corrective action in a movement or a plan adjusts interactions with marked tissue surfaces, based on the appearance of the mark. For example, upon approaching a mark, the operator of the intra-body probe can adapt navigating actions to account for the orientation of the surface. More particularly, a fixed-size mark (for example, a fixed-size mark indicating an intersection of an axis extending along the probe's current orientation with a modeled 3-D surface), may look compressed along one axis if the modeled 3-D surface is not orthogonal to a viewing axis (e.g., from the point of view of the probe). Additionally or alternatively, a searchlight-like mark (e.g., rendered to simulate a fixed-angle beam emitted from a probe's distal end and along its longitudinal axis) will appear non-circular on the surface from viewpoints at angles away from the longitudinal axis, when the probe is not orthogonal to the surface. Orthogonal contact (for example) may be preferable for some procedures such as injection and/or ablation, to help control results; and a non-preferred angle of approach can be corrected during a procedure once recognized. In another example, a shape of a surface-conforming mark may indicate to a user that the mark lies across a surface region having an irregular shape, such as a ridge of tissue (which may otherwise be sufficiently low-contrast in appearance that the shape irregularity is hidden or unclear). The user optionally adjusts a procedure (for example, moves a planned ablation location) in order to avoid the surface region with the irregular shape. In some embodiments, knowledge of a shape of a region targeted for a procedure is optionally updated during the procedure itself. Knowledge of other properties such as tissue state may also be updated during a procedure based on measurements; for example, state of tissue health, state of tissue edema, and/or state of tissue capacity to propagate electrical impulses. Insofar as marks are applied to the surface of the shape itself, an operator is able to make corrections to a planned procedure as it becomes apparent that marks indicating the plan are directly associated with revised-shape and/or revised-state surface regions that are potentially problematic.

In some embodiments, an estimated effect comprises an estimated change in temperature, such as for example, estimating heating when ablating and/or estimating cooling after ablation. Alternatively or additionally, an estimated effect comprises an estimated change in shape, for example, after ablation it might be estimated that a tissue will become swollen.

Alternatively or additionally, an estimated effect comprises an estimated change in texture, for example, when estimating the formation of a scar tissue, optionally resulting in variation of surface texture. Alternatively or additionally, an estimated effect comprises an estimated change in size, such as for example, following a measured and/or estimated edema, which may be estimated to take place following an ablation.

Optionally, the shape and/or appearance of a delimited region of the 3-D model is calculated based on the estimated effect. For example, borders of a region estimated to be heated as a result of ablation may be calculated based on an electrical power fed to an ablating element in the probe, the type of the ablated tissue, the tissue properties and so forth.

In some embodiments, an extent of a region to be rendered is calculated based on the estimated effect, such as by estimating an effect of a probe contact size, for example when estimating an area and/or a depth of ablation at a given ablation location. In some embodiments, the extent of the rendered region comprises a path of a plurality of ablation locations, optionally, some of which represent locations which were already ablated and some of which represent targets for ablation.

In some embodiments, a motion frame-rate, real-time display of a changing shape of tissue model is provided, wherein material appearance properties of the 3-D model are changed based on estimations resulting from ongoing measurements of interactions between a catheter probe and the actual tissue being modeled. Potentially, visually representing estimated data by changing the material appearance of a tissue's 3-D model may provide more realistic graphical presentation. In some embodiments, the realistic graphical presentation is selected to provide a more intuitively understandable presentation than that achievable with presentations that are not realistic. Optionally, appearances of scene objects are "realistic" in one or more aspects, for example, tissues are provided with material appearances that mimic their appearance in life and/or reactive behaviors (e.g. in response to injury, treatment, contact, and/or pressure). Optionally, scene object are given behaviors which are "naturalistic" as the term is used herein, with the result that they are not convincingly realistic, but nevertheless look and/or behave consistent with the possession of a virtual "substance".

Some embodiments involve visual rendering of surfaces and/or volumes as comprising virtual material. A virtual material, in some embodiments, is a material subject to simulated optical rules approximating processes such as reflection, scattering, transparency, shading, and lighting. Not every optical rule used in virtual visual rendering is a copy of a real-world rule; the art of computer rendering includes numerous techniques (for achieving both realistic and deliberately unrealistic results) which apply optical rules that have no direct physical equivalent. For example, bump mapping simulates surface height irregularities by manipulation of reflectance.

A region can be rendered statically or dynamically. In some embodiments, the region is rendered dynamically, and the changed material appearance over time is based on real-time input data, i.e. data collected during a procedure. For example, upon detection of a catheter ablation onset, a simulation of the tissue being heated is provided, and the 3-D model of the tissue is rendered so its appearance is affected by data collected during the ablation process. As used herein, real-time refers to the motion frame-rate, real-time display of a changing simulated tissue.

For example, a region can be rendered dynamically when a catheter is identified as approaching a tissue beyond a distance threshold, and the appearance of the tissue model is set to be indicative to the state of the tissue, such as hydration level, and/or edema, and/or fibrosis. Optionally, the tissue state is indicated by selecting a material appearance corresponding to at least one property of that state. In some embodiments, the tissue state is indicated by changing the material appearance of the geometrical surface and/or depth of the tissue based on ongoing measurement of tissue properties.

In some embodiments, a software environment specialized for interactive visual simulations (for example a 3-D graphical game engine such as the Unreal® or Unity® graphical game engines) is used as a basis for implementing the tissue simulation. For visual rendering by the game engine graphics pipeline, material appearances of tissue are optionally controlled by one or more material appearance properties (preferably a plurality of such properties). In some embodiments, material appearances are rendered according to how materials interact with simulated optical and lighting conditions.

In some embodiments, rendering material appearance properties is based, wholly or partially, on pre-stored input data. The pre-stored input data may relate to a plan for the catheterization procedure, and may include, for example, a planned ablation path. The path may be characterized by position and size. Alternatively or additionally, rendering material appearance properties is at least partially based on input data received on-line during the procedure, e.g., from one or more data sources active during a procedure in real-time. In some embodiments of the present invention, the data inputs optionally include inputs related to the performance of a catheter procedure—for example, catheter probe position data, data tracking the operation state of the catheter, and/or measurement data, for example measurement data obtained from an intrabody probe.

Optionally, material appearance properties are based directly on measured data, for example, material appearance of a modeled tissue may change as the tissue is being heated. The change in material appearance properties may be in accordance with real-time thermal measurements of the tissue. Alternatively or additionally, material appearance properties are based on estimated data derived from the measured data. For example, once an ablation is conducted, it is estimated that the tissue is being heated, and the extent of the heating can be derived from measured data of the probe or the tissue.

In some embodiments, material appearance properties are presented to illustrate a realistic representation of the tissue, as provided by input collected in real-time. Alternatively or additionally, material appearance properties are based on what is referred to herein as "naturalistic" representation, optionally based on exaggeration of measured and/or calculated data, for example, by exaggerated stretching and/or swelling of the appearance of a tissue based on a water retention status of the tissue. Herein, "naturalistic" appearance means that the displayed result gives an operator the impression of substantial (volume-occupying, as opposed to merely shell defining) and/or reactive materials existing in a fluidly navigable environment. The reactions of the materials in turn become a significant part of the information which an operator relies on to act within the actual environment that the scene simulates. A material moreover may be simulated as occupying volume per se (for example, as a wall having thickness), rather than merely as a boundary extending in space (for example, as a structure defining a surface, but having no well-defined thickness).

In some embodiments, in addition or as an alternative to immediate effects of probe-tissue interaction, longer-term effects are optionally simulated and displayed. The longer-term effects are optionally estimated; for example, a simulation that converts estimated lesion damage into parameters for a script describing the gradual onset of tissue edema.

An aspect of some embodiments of the invention relates to automatically modifying, during a catheterization procedure, an image presenting a modeled tissue.

Optionally, modifying an image comprises modifying the viewpoint used to render the modeled tissue, for example, a viewpoint from within the organ comprising the tissue region being modeled and/or a viewpoint from outside the organ. Alternatively or additionally, modifying an image comprises switching between a single representation of the model to a plurality of representations of the model, or vice versa. An example of a plurality of representations of a model includes simultaneously presenting more than one image, for example different images presenting different viewpoints. Alternatively or additionally, modifying an image comprises zooming in or zooming out from the rendered field of view. Alternatively or additionally, modifying an image comprises switching between a front view of the modeled tissue to a cross-sectional view of the modeled tissue, and vice versa. In some embodiments, an image is automatically generated during the catheterization process in accordance with an identified condition In some embodiments, each of a plurality of conditions is associated with an image presenting the 3-D model. Optionally, the conditions are related to the catheterization process, including for example, the relative position and/or orientation of the catheter probe relative to the presented tissue region, or for example an onset of an ablation process.

In some embodiments, the condition is related to a catheter's position and/or action with respect to the modeled tissue. Optionally, an associated condition comprises a distance between a distal end of a catheter probe and a tissue surface shorter than a pre-set threshold. In some embodiments, a different pre-set threshold value is set for different tissues, for example, when a distal end of the catheter approaches a tissue surface, the view may be zoomed in. The threshold for zooming in may differ based on the existence of planned sites on the tissue surface. For example, if the tissue surface includes a planned site (e.g., a planned ablation site), zooming-in may take place at a larger distance than if the tissue does not include planned sites.

In some embodiments, when approaching a tissue, optionally beyond a pre-set threshold, an indicating marker is rendered over the 3-D model. For example, when approaching a tissue having a planned ablation site, marking of the planned ablation site may appear when the catheter probe is detected to cross over a pre-set distance threshold.

An aspect of some embodiments relates to a simulated illumination rendered across a 3-D model during a catheterization procedure, shown by updating a presentation of the 3-D model to appear as if light is being projected over it. In some embodiments, the illumination is simulated to be originating from a determined position and/or illuminating in a direction of a determined facing direction of a distal end of a catheter probe. Optionally, projected light properties, such as intensity and/or dispersion, correspond to the determined probe position and/or orientation with respect to the tissue.

In some embodiments, the model is rendered from a viewpoint defined by a location over the catheter probe and by the facing direction of the probe. Alternatively or additionally, the model is rendered from a viewpoint location being distinct from the catheter probe, optionally including the distal end location of the catheter. Alternatively or additionally, the model is rendered from a viewpoint location being outside the organ comprising the catheter probe, optionally visually presenting only the illumination simulated to originate from the probe.

In some embodiments, the simulated illumination is rendered as if originating from a flashlight positioned in proximity to the distal portion of the probe and facing the modeled tissue. In some embodiments, a point-of-view of looking from the outside of the organ and seeing the flashlight as if illuminating from within the organ is provided. In this embodiment, the tissue of the organ is rendered to be transparent enough to let light pass through it.

An aspect of some embodiments of the invention relates to a presenting a model of a tissue surface as viewed from a location over a catheter probe, optionally during a catheterization procedure. In some embodiments, the model is rendered to be viewed from a viewpoint location being further away from the tissue surface than the distal end of the catheter probe. Optionally, the relative distance and/or facing direction between the tissue surface and the catheter probe is determined by receiving data indicative of a position and a facing direction of the distal end of the catheter probe with respect to the tissue surface.

In some embodiments, a graphical representation of at least a portion of the distal end of the catheter probe is rendered over the image, optionally correlating to the real edge distance of the catheter probe's distal end from the viewpoint location used for the rendering the 3-D model. In some embodiments, the presented catheter's distal end is dynamically presented, optionally rendered to be oriented with the detected position and/or facing direction. In some embodiments, rendering of the tissue model is provided in real-time, i.e. during acquiring of input, such as for example, electrical reading optionally from an electrode mounted on the catheter probe. In some embodiments, the input detects that the 3-D structure of the tissue model has changed to a second structure. Optionally, the model is rendered to present the second structure of the tissue surface.

Aspects of some embodiments of the invention are described in the following exemplary embodiments, depicting an exemplary cardiac ablation procedure. It should be noted, however, that various aspects and implications of the invention which are described in the context of ablation and/or cardiac embodiments, are probably applicable to many other medical procedures, and/or other patient anatomies, and the embodiments of the invention as described herein are not limited in any way to the illustrative example of cardiac ablation.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Exemplary Ablation Procedure

Aspects of some embodiments of the invention relates to a user interface for assisting in medical procedures, guiding a surgeon by updating the appearance and/or images used to render a 3-D model of a tissue, optionally based on a catheter's position and/or operation with respect to the modeled tissue. In some embodiments, catheterization procedures are directed for treating cardiac arrhythmia conditions, such as for example atrial fibrillation (AF) and/or atrial flutter (Afl) and/or supraventricular tachycardia (SVT) and/or atrial tachycardia and/or Multifocal Atrial Tachycardia (MAT). Alternatively or additionally, a procedure is directed to cancer treatments, and/or pain management, and/or for cosmetics purposes.

Figure 2:
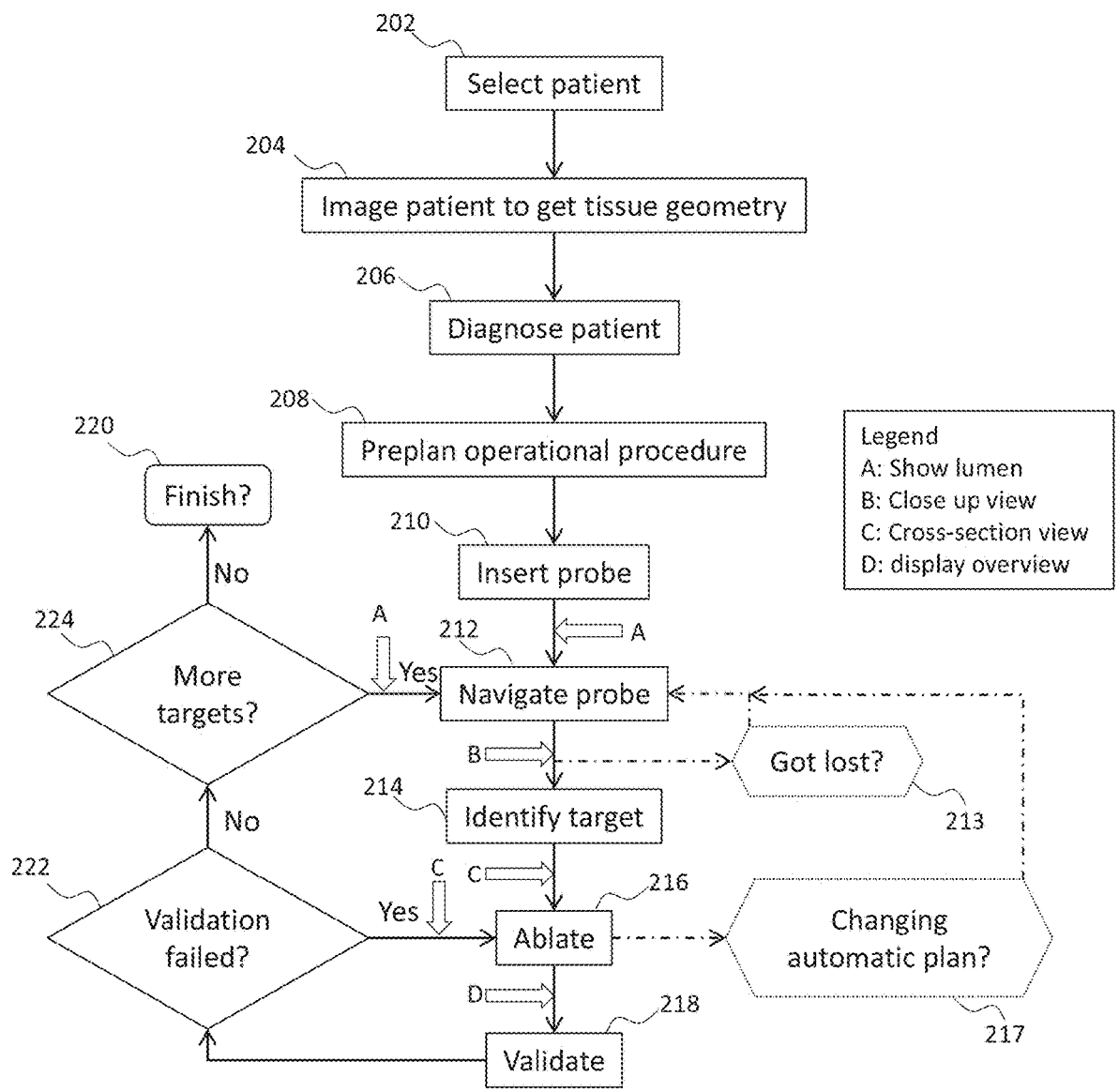

Referring now to the drawings, FIG. 2 shows a flowchart depicting an exemplary high level outline of a cardiac ablation procedure, such as for example for treating AF, while executing embodiments provided by the current invention.

Optionally, a patient, such as for example, a patient suffering from a cardiac arrhythmia condition, is selected for treatment 202, such as for example, ablation and/or neuro-modulation. In some embodiments, a patient is imaged 204 to obtain a shape of an organ or part thereof; for example to obtain a cardiac tissue 3-D shape. As used herein, a tissue includes at least a portion of a patient's organ. In some embodiments, imaging is done by magnetic resonance imaging (MRI), and/or computed tomography (CT), and/or by ultrasound (US) and/or by nuclear medicine (NM). Alternatively or additionally, data is acquired by measuring thermal and/or dielectric tissue properties. In some embodiments, data acquired by sensing dielectric properties is used in obtaining the shape of the organ, in addition to or instead of data from the imaging of block 204. Optionally, an initial 3-D geometric tissue model is provided by combining a mesh of a plurality of data inputs, e.g., from different imaging modalities. Optionally, such data is used in a diagnosis process of the patient 206.

Preplanning and Plan Adjustment

Based on the pre-acquired data, in some embodiments, a surgeon and/or a simulation program preplans an operation procedure 208. The operation procedure may include, for example, generating a lesion. In some embodiments, a preliminary target to be lesioned is visually presented to a surgeon, e.g., as a path (for example a continuous path, and/or a path described as a series of locations to be lesioned). In the visual representation, the path may be presented as matched to a 3-D model of the patient's tissue.

For example, during a preplanning phase a surgeon may draw a path creating a 2D structure over a presented 3-D model. In some embodiments, the path is then deformed to match across a region of the 3-D model of the patient-specific anatomy, thereby leading to a planned graphical structure which is specific to the patient at hand.

Optionally, the preplanning comprises planning a line of ablation points, along which lesions are to be formed. The line may include a plurality of locations at which ablation is to be performed to create sub-lesions. Optionally, planned ablation locations are shown as area markings. In some embodiments, planned lesion area markings size takes into consideration the ablation tool being used.

In some embodiments, the size of the lesion area marking corresponds to the contact area of the ablation tool; indicating, for example, that a probe with a specific surface contact area will be used. Optionally, an indicating marker is also used in illustrating the order of ablations, and in some embodiments the order of ablations is represented visually, for example by using a gradient of a visual parameter, such as when color intensity of area markings goes down or up in accordance with their planned ablation order.

In some embodiments, an ablation plan includes specification of where ablation is to occur; optionally defined as a line or path, an area, and/or a volume (herein, ablation plans for a path are provided as examples, without limiting away from embodiments using areal or volumetric specifications). A visual presentation of an ablation plan which may be displayed to a surgeon during the procedure, optionally further comprises a presentation of ablation parameters (for example, total energy to be delivered, power and/or timing).

In some embodiments, graphical presentation of the planned procedure, being matched with a patient-specific shape, is provided to a surgeon during the procedure in real-time. In some embodiments, the graphical presentation is dynamic. For example, If the procedure in real-time deviates from the planned procedure (e.g., due to changes in following the plan, differences in plan effects from those anticipated, differences in actuality of the state of the patient and/or procedure site from the state anticipated in the original plan, and/or realization of a benefit for following an alternative plan), the graphical presentation dynamically changes accordingly. For example, an indicating marker can change according to real-time measurements, such as real-time dielectric measurements and/or real-time thermal input.

Navigating and Dynamic Image Modification

In some embodiments, a procedure starts when a catheter probe is inserted into the patient 210, and optionally used for navigating 212 and/or for identifying a target 214.

Optionally, the user interface graphically represents aspects related to maneuvering within the confines of an anatomical space, the graphics being presented as material appearance of the 3-D model. For example, there may be mechanical limitations on the maneuvering of an ablation catheter which in some embodiments are graphically represented in the geometrical model by shading the surface area and/or modifying the geometrical surface of the area to seem dim and/or dull and/or otherwise make it appear to be unreachable.

In another example, an anatomical region which is mechanically accessible could be inappropriate for lesioning. Such anatomical regions may be graphically presented as unreachable, or in any other way designed to deter the surgeon from lesioning them. Anatomical regions that are not to be ablated may include, for example, a region of the esophagus and/or arteries and/or venous roots and/or autonomic ganglia and/or phrenic nerve.

In some embodiments, at least one measured and/or estimated tissue property is updated during navigation 212. The update may be by changing material appearance properties of the presented 3-D model. For example, an aspect of several embodiments of the invention relates to updating a tissue model according to a hydration state of a patient, in real-time. In some embodiments, graphical simulation is used to graphically represent a hydration state of a patient. In some embodiments, a simulation of exposure to an optical light environment is used to graphically present a wet appearance to a tissue model, optionally correlated with a hydration measurement state.

In some embodiments, a color used to render a 3-D model of a tissue surface is determined by the presence of at least one biological marker. For example, red color can in some embodiments represent levels of hemoglobin protein. Alternatively or additionally, color is determined according to a surface characteristic, for example, color change according to a roughness level of a surface tissue. For example, roughness may represent rough texture features of a tissue such as fibrosis.

In some embodiments, presentation is refreshed at a rate of tens of times per second. A potential advantage of a relatively fast refresh rate is showing real-time state of the tissue even when the catheter interacts with the tissue. Optionally, tissue properties are updated only when a catheter's position is detected near the modeled tissue, e.g., the distance of a distal end of the catheter distance from the tissue surface is smaller than a predetermined threshold.

In some embodiments, once a probe is inserted 210, dynamic image modification (referred to in FIG. 2 as arrow A) is provided, optionally automatically. In some embodiments, automatic image modification is provided based on detection of the catheter's position and/or orientation relative to the modeled tissue. Optionally, once the catheter is identified to cross over a predetermined distance towards and/or away from the tissue, the presented image is modified. In some embodiments, image modification comprises modifying the viewpoint location used to generate the model, for example, modifying the location from within an organ comprising the modeled tissue to a location outside the organ. In some embodiments, modifying includes switching between images. Alternatively, modifying includes adding or removing an image.

In some embodiments, a viewpoint location is automatically modified when detecting a catheter getting close to a selected tissue target. The selection of the tissue target may be, for example by planning, by operation of a user interface that deviates from a plane, or otherwise. In some embodiments, getting close is determined when sensing a position of the catheter relative to the defined target, optionally combined with an evaluation of the catheter's orientation with respect to the defined target. In some embodiments, a threshold distance for modifying the viewpoint location is also affected by the orientation of the catheter when approaching the target. For example, if the orientation of the catheter is facing away from the direction of the target site, the threshold distance to shift points-of-views would be a smaller distance between the catheter and the target site than if the orientation of the catheter is facing towards the target site. In some embodiments, an inset and/or a preview of the modified image flicker temporarily. In some embodiments, only after the surgeon persists in the detected direction, the modified image remains stable. In some embodiments, once an image is stable, it would not be modified again for a predetermined period of time, such as in the range of 1-2 sec, 2-5 sec, or 5-10 sec.

In some embodiments, an image is provided as viewing a cross-section of a tissue depth. Optionally, dynamic image modification includes automatic dynamic zooming in into regions of interest. In some embodiments, a plurality of images is shown simultaneously on the same user interface. Optionally, a single image can automatically replace the plurality of images, such as for example, when detecting an onset of a probe's operation, a single image depicting its operation is provided.

Optionally, vice versa automatic image modification from a single image to multiple images is provided.

Identify Target

In some embodiments, the catheter is detected as approaching a selected (e.g., plan-selected) target 214, optionally by dielectric measurements. In some embodiments, a catheter is detected as approaching a target by determining the position of a distal end portion of the catheter probe (e.g., determining the position of one or more electrodes and/or sensors located on catheter, e.g., the distal end thereof). Alternatively or additionally, approaching a target may be detected by calculating a position of the distal end portion of the catheter probe based on one or more electrical and/or dielectric and/or thermal parameters (e.g., field, current, voltage, and/or impedance). Alternatively or additionally, approaching a target may be detected by correlation of measured parameters with values of the same parameters obtained by a simulation. The simulation may include simulated positions of a simulated catheter probe within a 3-D model, the model associated with estimated dielectric parameter values and/or with estimated thermal parameter values.

Optionally, the simulation is iteratively updated according to one or more parameters measured in real-time, for example, electrical parameters and/or thermal parameters of tissues, measured by intra-body sensors. The electrical parameters may include dielectric parameters, such as impedance of the myocardium of the heart (or other target-related tissue), and/or conductivity of the blood, and/or thermal parameters such as thermal conductivity and/or heat capacity. The measured values may be fed back into the simulation, to update the estimated electrical values and/or thermal values with the measured parameters values. The simulation may be re-generated to generate an updated set of simulated positions for correcting the measured physical location of the distal end of the catheter. Optionally, the measuring and updating of the simulation are iterated, to improve the accuracy of the corrected distal end position. The iteration may be performed to reach a target accuracy, such as an accuracy fine enough for performing the treatment procedure.

In some embodiments, once a target is approached, dynamic image modification B is provided. Exemplary dynamic image modification can be seen in FIGS. 6A-F and 9A-G. Optionally, when the catheter is detected to be near a target site, a close up view is provided. In some embodiments, a planned target is visually presented as a graphical object, such as a path, matched to the 3-D surface of the 3-D model of the tissue presented, such as seen for example in FIGS. 6A-F and 9A-G. Optionally, a planned target only appears after zooming in over the modeled tissue. In some embodiments, the resolution of the graphical object is higher when viewing the tissue more closely, such as illustrated in FIGS. 6C and 6D.

In some embodiments, if no target is identified after a pre-set time period, it is possible a catheter is lost 213 with respect to its target site. Optionally, at this point, the view is modified automatically to show an outer view of the target area and/or organ.

Ablation

In some embodiments, when contact is detected between the probe and the tissue surface, and/or when ablation onset is provided 216, the view is shifted C, for example to a cross-sectional view of the treated tissue. In some embodiments, only the planned tissue region is visually rendered. Alternatively, a simulated section is provided with at least one neighboring planned region, as illustrated in FIGS. 7A-F.

Alternatively, a simulated region is shown surrounded by its immediate surrounding tissue, as illustrated in FIGS. 9A-G and FIG. 11. Optionally, once a planned ablation procedure is complete, the image is modified automatically to present an overview of the procedure, such as illustrated for example in FIG. 8 and FIGS. 10A-B.

In some embodiments, an operational procedure plan is automatically or manually changed in real-time during a procedure 217. Optionally, updating of the plan is according to deviations due to differences between planned and intended actions during the operational procedure; for example, movement of a lesion site to a new position, by accident or on purpose. Optionally, updating is according to new data describing features of the operational procedure site overall, for example, previously unknown details of anatomy (such as may occur, for example, as a consequence of normal inter-subject anatomical variability, normal intra-subject changes in anatomy, and/or disease). Optionally, updating of the plan is according to tests carried out which indicate that an intended effect of the treatment (e.g., blockage of electrical impulse activity) is incomplete or otherwise not as anticipated by the existing plan. Automatic updating may comprise accepting data indicating, for example, any of the just mentioned conditions, identifying that a plan deviation has occurred, and formulating a new plan which compensates for the deviation.

Validation

In some embodiments, after completing an ablation process and/or after displaying an ablation overview, validation 218 takes place, optionally to validate an effective block of pulse propagation. In some embodiments, dynamic image modification D is provided when detecting onset of validation, optionally automatically modifying to an image showing an overview of the ablation process, optionally graphically presenting actual ablation simulation and/or planned ablation paths. Validation views and visual representations are exemplified in FIG. 12.

In some embodiments, if validation fails 222, i.e. no sufficient blocking of pulse propagation is accomplished, a repeated ablation is optionally provided. In some embodiments, when validation is detected as failed, a detected proximity of a catheter to the failed ablation site results in automatic view shifting B to an ablation view.

In some embodiments, after validating, even if validation is successful, more ablation targets are pursued 224, and optionally the presented image is automatically modified, for example to navigation view A. If not more validation is needed, the procedure is optionally finished 220.

Exemplary Model Renderings

Reference is now made to FIGS. 1A-1E, showing flow charts of processes for rendering a 3-D model, optionally in real-time, in accordance with some embodiments of the invention.

Some of the processes of FIGS. 1A-E, in some embodiments, include the use of a 3-D model of a tissue, optionally a tissue surface. In some embodiments, the 3-D model comprises mesh data; for example as is commonly used in defining structures for computerized visual rendering of 3-D structures. In some embodiments, the 3-D model specifies positions (and usually also connections among positions, and/or positions joined by the extent of a common surface and/or material volume), corresponding to positions of surfaces of a target body tissue region to be visually rendered for presentation. Optionally, the geometry of positions defining an interior shape of the surface is also represented (for example, where presentation includes the use of transparency and/or cross-sectional views). Surfaces represented are optionally external (e.g., organ surfaces; not necessarily surfaces visible externally to the body) and/or internal (e.g., lumenal) surfaces of the target body tissue region. In some embodiments, a 3-D model is derived from anatomical data; for example, appropriately segmented 3-D image data of a patient.

In some embodiments, at least a portion of the surface presented by the 3-D model rendered with at least one material appearance property (MAP). As the term is used herein, MAPs comprise any properties associated to positions in a virtual environment for visual rendering according to simulated optical laws, and which affect how a surface and/or its enclosed volume are visualized within a 3-D rendered space. MAPs are usually, but not only, assigned to surface positions of the 3-D model. MAPs are optionally assigned to volumes defined by surfaces of the 3-D model. MAPs can also be assigned to the virtual environment (e.g., as lighting parameters) in such a way that they affect material appearance.

Creating the visual rendering in some embodiments treats surfaces and/or volumes as comprising virtual material. A virtual material, in some embodiments, is subject to simulated optical rules approximating processes such as reflection, scattering, transparency, shading, and lighting. Not every optical rule used in visual rendering is a copy of a real-world rule; the art of computer rendering includes numerous techniques (for achieving both realistic and deliberately unrealistic results) which apply simulated optical rules that have no direct physical equivalent. For example, bump mapping simulates surface height irregularities by manipulation of reflectance. Ambient occlusion is an efficiently calculable lighting effect defined in association with surface maps, wherein light sources are treated as approximations.

Additionally, it should be understood that not everything discussed herein as a material appearance property is necessarily a property of a virtual material as such. For example, in some embodiments, certain effects of lighting are implemented using sources which are virtually placed remote from a surface they illuminate (and so, not defined as properties of the surface's virtual material). Nevertheless, insofar as the properties of these lights affect the appearance of the material, they are classed within the meaning of MAP. Also herein, where needed to make a distinction, the phrase "material properties of appearance" is used to indicate MAPs defined for a virtual material as such (rather than as part of the lighting environment).

Optionally, baseline MAPs data are initially assigned to surfaces (optionally, volumes) defined by the 3-D model so that these surfaces resemble, when suitably rendered for visual presentation by user interface, simulated versions of the tissue they represent. For example, a muscular organ such as the heart is optionally rendered as a mottled reddish-pink, optionally with additional surface properties such as scattering, roughness, specular reflection properties, and/or overall reflectivity defined to give it irregular gloss evocative of a wet surface. Highly vascular structures such as liver and kidney tissue are optionally represented with a more uniform and ruddier hue.

Optionally, baseline MAPs data takes into account tissue state data which characterizes tissue beyond its geometrical shape. In some embodiments, for example, 3-D nuclear imaging data is optionally used to distinguish between healthy and scarred cardiac muscle tissue. Scarred tissue is optionally distinguished in presentation by differences in one or more virtual optical properties from healthy tissue (e.g., rougher, duller, and/or grayer in appearance).

In some embodiments, procedure effects, whether measured, estimated and/or calculated, are rendered onto the baseline MAPS, and/or rendered as providing other visual texture characteristics; for example, alterations to MAPs governing visual roughness and/or specular reflection are made (e.g., ablated tissue becomes "dull" and/or edematous tissue becomes "smooth").

In some embodiments, changes in MAP from baseline are optionally chosen to reflect conventions or expectations of how a procedure affects tissue. Alternatively or additionally, changes in MAP from baseline are optionally exaggerated for clarity. For example, even if an already well-perfused tissue does not actually become "redder" when inflamed, it is still an option, in some embodiments, to apply MAP reddening comprising, e.g., color shift, brightening, and/or increase in saturation to indicate an inflamed state. Similarly, heating and cooling are optionally indicated by assigning "redder" or "bluer" MAPs; adding an icy gloss to cooled-off tissue; adding smoke, glow, and/or flame to heated tissue; etc. In another example, the surface of a region injected with a substance such as Botox® (Allergan, Inc., Irvine Calif.) is optionally represented as having MAPs which give it a "smoother" appearance (e.g., bump map texturing is suppressed), whether or not smoothness relates to a realistic appearance change.

In some embodiments, MAPs are defined using light source positioning, for example, to selectively illuminate (e.g., in simulation of a laser or flashlight light beam) a tissue region. As for the examples of lighting, this optionally comprises a MAP having an underlying definition in data and/or software which is positioned outside the virtual material of a surface whose display appearance is affected.

Figure 1A:
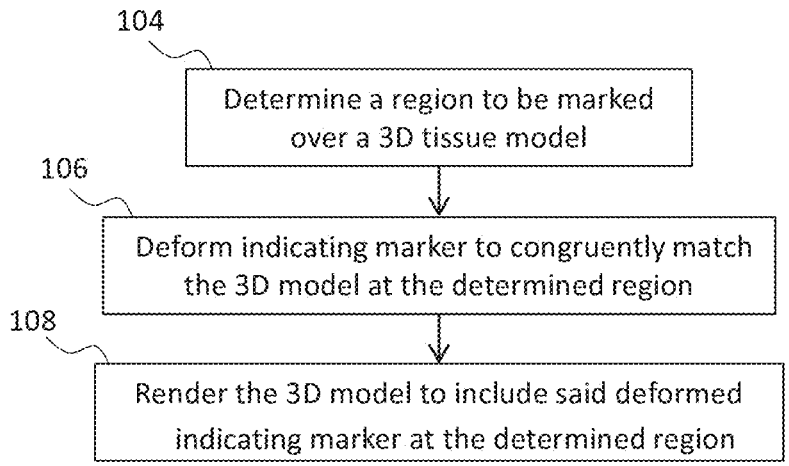

Reference is now made to FIG. 1A, showing a flowchart exemplifying a process for rendering a simulated indicating marker over a 3-D tissue model, in accordance with some embodiments of the invention. The indicating marker may be used, for example, as a point of reference and/or as an indicator to results of one or more measurements. For example, an indicating marker may be used as a point of reference of the position and/or facing direction of the catheter probe relative to the presented tissue. Alternatively or additionally, the indicating marker may be used to point in the direction of a selected (e.g., planned) target site, which may comprise tissue targeted for approach, measurement, and/or treatment. Alternatively or additionally, the indicating marker may be used for marking one or more regions. The regions to be marked may be, in some embodiments, planned, calculated, selected by user input, and/or estimated.

Optionally, the process includes assigning a graphical object to the indicating marker, optionally having a visual presentation related to its meaning. For example, an indicating marker representing a point of reference may be assigned a target sign and/or an arrow pointing in the direction of the point of reference. In another example, an indicating marker representing a region may be assigned a delimiting line across and/or surrounding the region to be marked.

In some embodiments, the assignment of graphical objects to the indicating markers is pre-set, for example, before the catheterization procedure begins. In some embodiments, at least some visual appearance properties of the graphical objects assigned to an indicating marker is set in real-time, for example, a color of a graphical object may be set based on the color of the tissue it covers, the shape of the graphical object may be set based on the target pointed by the indicating marker, etc.

In some embodiments, a region to be marked with the indicating marker over the 3-D model is determined 104. Optionally, the region to be marked is determined by determining a location in the 3-D model together with a size and/or a shape of the region. In some embodiments, the position of the region to be marked is determined by measurements provided in a specific position in relation to the real tissue. Alternatively or additionally, the position of the region to be marked is determined based on a decision made in advance, such as in the case of preplanning. Alternatively or additionally, the position of the region to be marked is determined based on spatial relationship between an object and the tissue, such as for example, the location of the catheter probe in relation to the tissue.

Optionally, the size of the region to be marked corresponds to data being represented by the indicating marker. For example, when referencing the location of a catheter probe relative to the modeled tissue, a larger or smaller region may signify a closer or farther location of the probe.

In some embodiments, the shape of the region to be marked corresponds to data collected in real-time. The data may include, for example, measurements, and/or calculations based on real-time measurements, and/or estimations based on real-time measurements and/or calculations. For example, the shape of the region to be marked may correspond to a measured spread of heat and/or electrical current through the tissue.

In some embodiments, the indicating marker is deformed to congruently match the 3-D model at the determined region to be marked as in step 106. As used herein, congruently matching comprises deforming a graphical element to fit with a shape defined by a 3-D model in a plurality of positions, to generate an image of the 3-D model covered by the graphical element, not necessarily on the surface of the model. In some embodiments, fitting over a plurality of positions comprises deforming the graphical element to spread over a plurality of planes defined by the geometric surface of the 3-D model.

In some embodiments, the process includes a step 108 of rendering the 3-D model to include the deformed indicating marker at the determined region to be marked. In some embodiments, the indicating marker indicates a direction of a selected target site. Alternatively, the indicating marker indicates a planned path. Alternatively, the indicating marker indicates a field of view viewed from a location along the catheter probe, the location being determined by a measured position and facing direction of a distal end of the catheter probe.

In some embodiments, an appearance of the indicating marker indicates a relative location of the catheter probe with respect to the tissue surface, the relative location being determined by a measured position and facing direction of a distal end of the catheter probe relative to the tissue surface. Optionally, a size of the region indicates a distance between the catheter probe and the tissue surface. Alternatively or additionally, a visibility of the indicating marker indicates a distance between the catheter probe and the tissue surface. Alternatively or additionally, an aspect ratio of the region indicates an orientation between the catheter probe and the tissue surface.

In some embodiments, it is identified that an indicating marker should be presented, optionally based on rules pre-associated with input which is expected to be acquired during the catheterization procedure. In some embodiments, input includes the identified onset of a navigation process, such as for example, when identifying navigation tools being powered on. Alternatively or additionally, input includes identifying the onset of ablation, for example, by detecting operation of the catheter probe, and/or contact with the tissue, and/or heat.

Figure 1B:
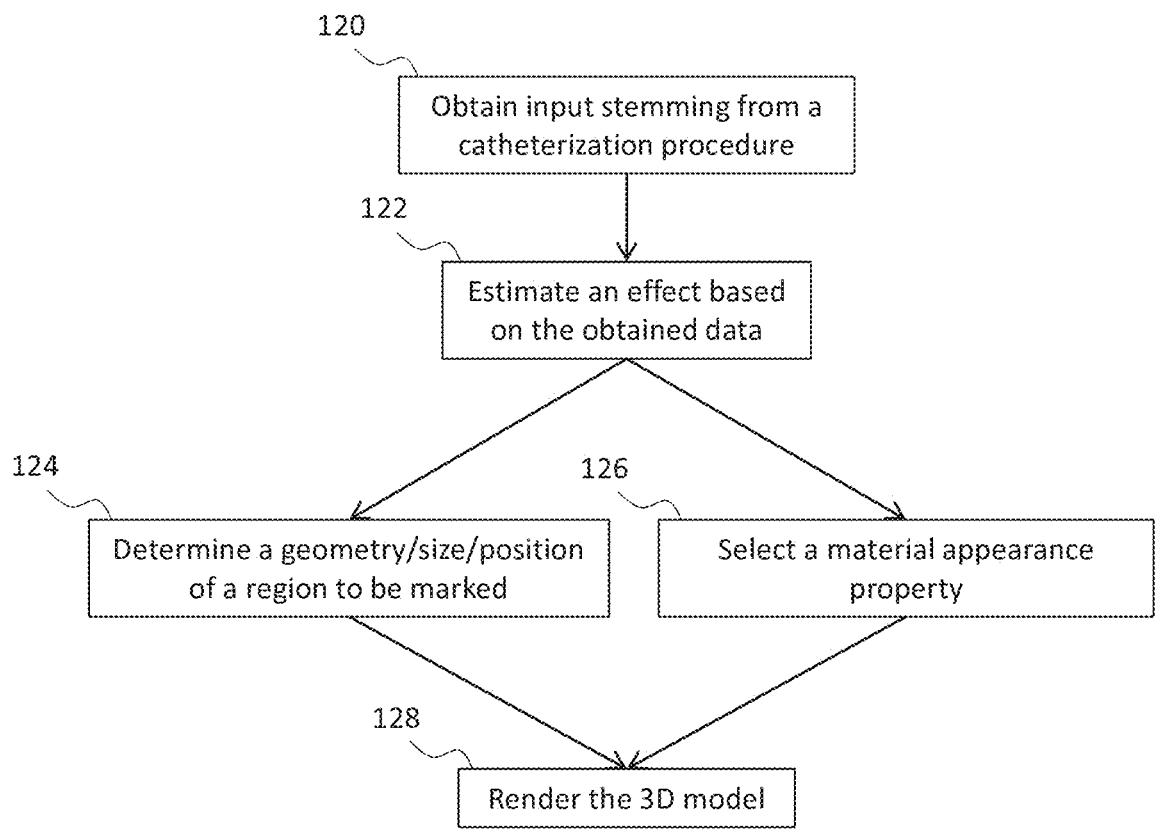

Reference is now made to FIG. 1B, showing a flowchart exemplifying a process for rendering a geometric tissue model based on estimated data, in accordance with some embodiments of the invention.

At 120, input is collected during a catheterization procedure. Optionally, input is measured in real-time, and/or calculated from such measurements. At 122, an effect is estimated based on the input. For example, when the collected input is a start of an operation of an ablation probe, an effect of the operation of the ablation probe may be estimated. For example, it may be estimated that heating takes place. Optionally, a plurality of inputs is combined to characterize the estimated effect. For example, the properties of the tissue are taken in consideration when estimating the effect of starting operation of an ablation probe.

At 124, parameters characterizing a region of the 3-D model to be marked are determined based on the estimated effects, optionally taking into account the measured input. The parameters may include, for example, shape, size, and/or position of the region to be marked. For example, a region to be marked may be determined to have a symmetric shape if the tissue is uniform and the effect of the probe is estimated to be uniform. Alternatively, a region to be marked may have an irregular shape when an effect is estimated to affect in a non-uniform manner and/or when non-uniform tissue characteristics are detected, such as a scar, and/or edema and the like.

In some embodiments, calculating a shape comprises calculating an area of an ablation point. Alternatively or additionally, calculating a shape includes calculating a depth of an ablation point. Alternatively or additionally, it includes calculating a path of a plurality of ablation points.

Optionally, an estimated effect is presented as a function of time. For example, when starting an ablation, it is estimated that heat will be dissipated, after which the tissue would be cooled again. In some embodiments, at the onset of an ablation, a sequence of events as a function of time is presented. In some embodiments, the shape of the tissue surface is recalculated at different times during the procedure, and the presentation thereof is modified accordingly. Optionally, the shape and the material appearance properties indicate an increasing spread of a lesioning effect.

At 126, at least one material appearance property (MAP) is selected for the region to be marked. Optionally, the MAP is selected from a database comprising a plurality of MAPs. Optionally, each MAP in the database is associated with at least one estimated effect. Optionally, the database includes associations between MAPs and effects.

At 128, the 3-D model is rendered with the determined region being marked using the selected at least one MAP. In some embodiments, the estimated effect is dynamic, for example, in the sense that it evolves over time, and accordingly the rendering is dynamic. In some embodiments, the modeled shape of the region to be marked changes over time, and/or the size of the region changes over time, and/or the position of the region changes over time, and/or the selection of MAPs change over time.

Figure 1C:
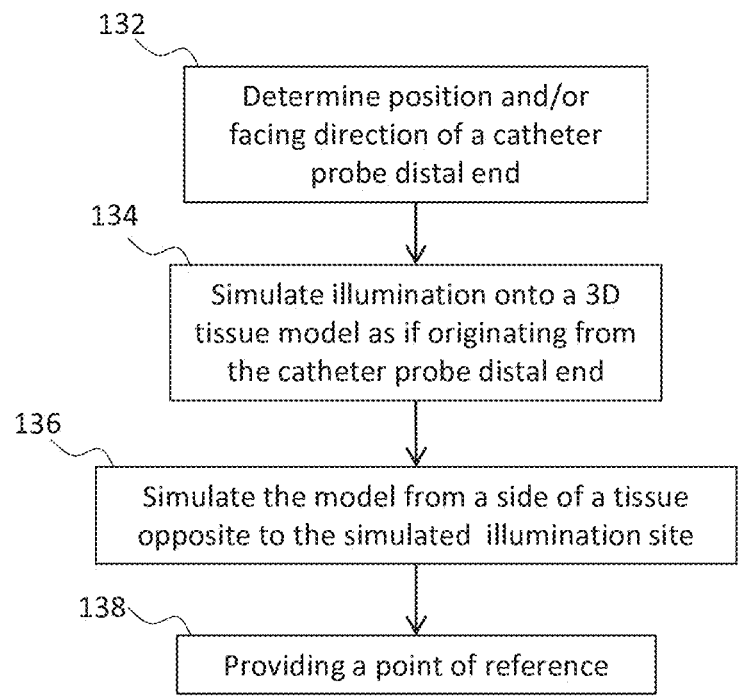

Reference is now made to FIG. 1C, showing a flowchart exemplifying a process for providing a point of reference for rendering a 3-D tissue model by simulation of illumination, in accordance with some embodiments of the invention.

In some embodiments, a catheter probe, and optionally specifically the distal end of the catheter probe, is detected to determine 132 its position and/or facing direction relative to a tissue. Optionally, the tissue region comprises a body lumen.

In some embodiments, a 3-D model of the tissue is rendered to simulate illumination 136 as if originating from the determined position of the catheter probe and illuminating in the direction of the determined facing direction of the catheter probe. In some embodiments, the 3-D model is rendered from a viewpoint located along the catheter probe, causing the illumination to simulate a flashlight. Optionally, the tissue modeled is visible beyond the simulated beam of the flashlight due to simulation of at least one second illumination source, such as for example, simulation of ambient light. In some embodiments, the 3-D model is rendered as viewed from a viewpoint offset to said distal end of said catheter probe.

Figure 3A:
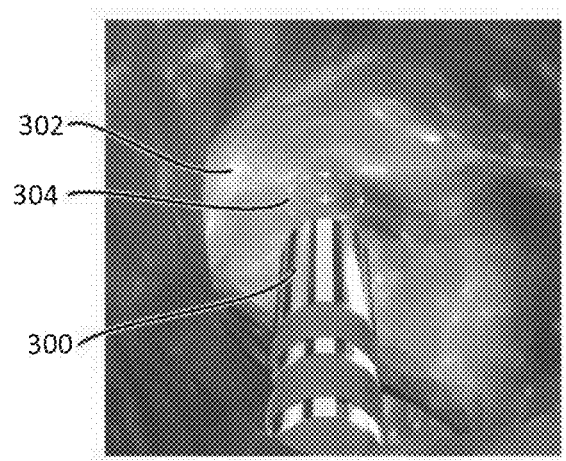
Figure 3B:
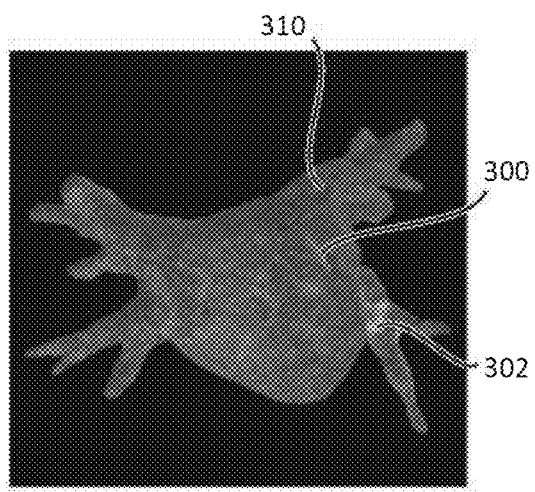

Optionally, the illumination simulated to be originated from the catheter probe is viewable at 136 from a side of the model opposite to the illumination site, i.e. opposite to the location of the catheter probe, optionally from a viewpoint located outside of the organ comprising the catheter, such as shown, for example, in FIGS. 3B and 3-D. In some embodiments, illumination is viewable from the other side by rendering the tissue at least partially transparent. In some embodiments, two images are provided, one rendered from a viewpoint inside of the organ and the other rendered from a viewpoint outside the organ, both having a respective illumination. A potential advantage of showing the same illumination from two different viewpoints is to provide both a reference of the position and a reference of a facing direction of the probe in a single glance.

In addition, it provides an easy and intuitive interpretation of the orientation of the probe within the organ, in the context of its proximal environment when viewing from within, and in the context of the entire organ when viewing from outside and thus provides 138 a point of reference to the surgeon. In some embodiments, the determining and the rendering is provided iteratively during at least a portion of the catheterization procedure.

Optionally, the method comprises presenting the 3-D model as viewed from at least two viewpoints simultaneously, a first viewpoint being inside an organ comprising the tissue region and a second viewpoint being outside the organ, and wherein both presentations include the simulated illumination as if originating from the determined position and in a direction of the determined facing direction of the catheter probe.

In some embodiments, the illumination is simulated to be uneven across a simulated illumination beam. Alternatively or additionally, a center of the illumination is calculated according to a position and facing direction of the catheter probe relative to the tissue region. Optionally, the center of illumination is graphically presented by increased illumination intensity at a center of said beam. In some embodiments, a second illumination sourced from a position distinct from the position of the distal end of the catheter probe is provided. Optionally, the second illumination is simulated to face a direction distinct from the facing direction of the distal end of the catheter probe. Alternatively or additionally, the second illumination is simulated as an ambient light source.

In some embodiments, a material appearance of a surface of the tissue region is selected and the material appearance is optionally simulated to be affected by the illumination. Optionally, the tissue model is rendered to appear at least partially translucent to the simulated illumination.

Figure 1D:
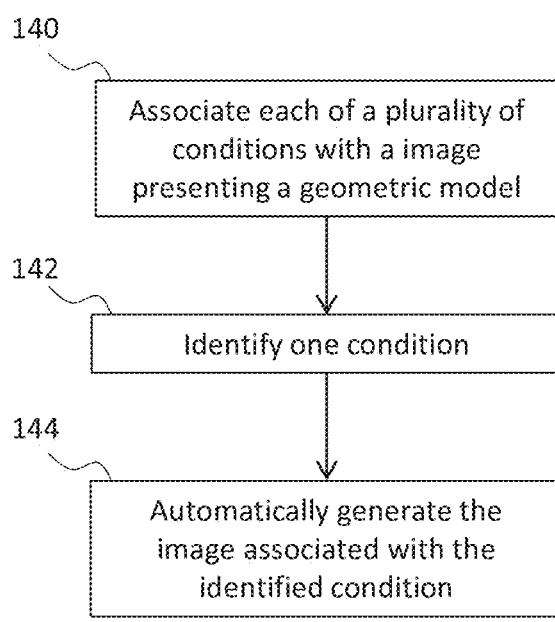

Reference is now made to FIG. 1D, showing a flowchart exemplifying a process for automatically modifying the image presenting a 3-D tissue model, in accordance with some embodiments of the invention.

In some embodiments, during a procedure, a surgeon uses at least one screen, having a user interface provided to guide the surgeon throughout the procedure, for example, by presenting tissue models, indicating markers, numerical data and so forth. In some embodiments, the image presenting the modeled tissue is modified automatically during the catheterization procedure, optionally in response to input collected during the procedure. In some embodiments, an image which is estimated to be the most helpful to the surgeon at an identified condition of the procedure is generated.

In some embodiments, at 140, each of a plurality of conditions is associated with an image for presenting the 3-D model. In some embodiments, an image is defined by a plurality of parameters. Optionally, the parameters may include a region to be marked (including position, shape, and size of the region), and/or MAPs selected for the region. Alternatively or additionally, the parameters comprise a viewpoint from which the model is to be presented to the surgeon, a zooming in or zooming out, a single image or a plurality of images, and so forth.

In some embodiments, at 142, a condition is identified and at 144, the image associated with the identified condition is automatically generated. In some embodiments, the plurality of conditions relate to a catheter probe's position and/or operation with respect to the modeled tissue. For example, a condition may comprise a distance between a distal end of a catheter probe and a tissue surface shorter than a pre-set threshold. Alternatively or additionally, a condition may comprise the tissue surface including a selected (e.g., planned for an action of the procedure, or otherwise indicated) site. Alternatively or additionally, a condition may comprise changing an operation state of a catheter probe, such as turning the power on or off. Alternatively or additionally, a condition may comprise detecting a contact of a distal end of a catheter probe with a surface of the modeled tissue.

In some embodiments, once a condition is identified, its associated image is automatically generated. Optionally, an image is generated by modifying the viewpoint used to render the model. Alternatively or additionally, an image is generated by zooming in or zooming out of the field of view of the model. Alternatively or additionally, an image is generated by changing the viewing angle of the image, such as for example, presenting a top surface of the modeled tissue surface area or presenting a cross-section of the depth of the modeled tissue. Alternatively or additionally, an image is generated by adding or removing an image, for example when switching between a single image to a plurality of images, and vice versa. Alternatively or additionally, an image is generated by rendering the model to include a graphical object across a region of the model.

Figure 1E:
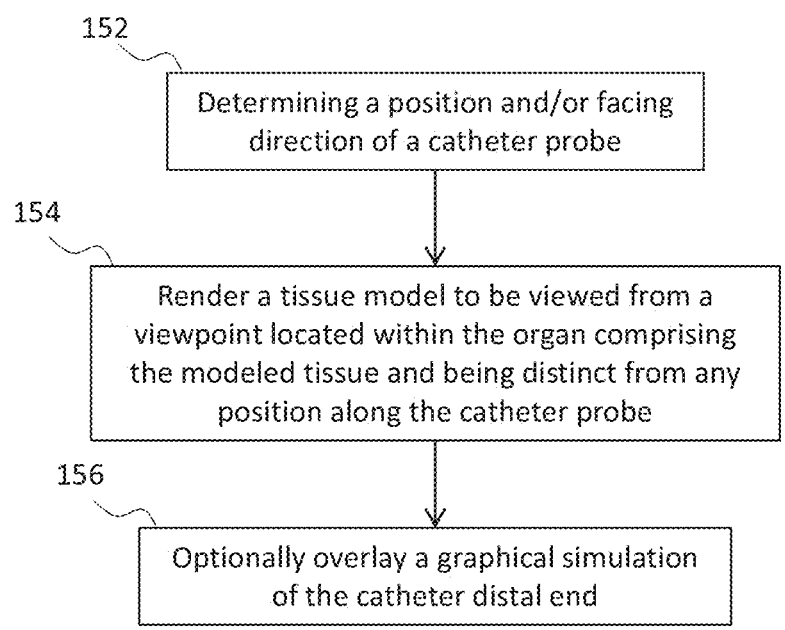

Reference is now made to FIG. 1E, showing a flowchart exemplifying rendering of a 3-D model of an inside environment of an organ, as if viewed from a location distinct from any position along the catheter probe, in accordance with some embodiments of the invention.

In some embodiments, a position and/or facing direction of a catheter probe are determined 152. Optionally, the position and/or facing direction determined are of the catheter probe's distal end. Optionally, the catheter probe position and/or facing direction are continuously measured during a catheterization procedure. In some embodiments, a 3-D tissue model is rendered at 154 to be viewed from a viewpoint location distinct from any position along the catheter probe, optionally such that the tissue targeted by the catheter probe and the distal end of the catheter probe could be modeled in a single field of view. Optionally, the field of view further includes a region to be marked across the modeled tissue. In some embodiments, the location is found further away from the catheter distal end than the modeled tissue surface. Optionally, the rendering is dynamic and is updated with the on-line measurement of the catheter probe position and/or facing direction.

In some embodiments, a graphical presentation of the catheter distal end is overlaid over the rendered model in step 156. Optionally, the overlaid distal end is dynamically presented by modifying the graphics to represent the detected facing direction of the catheter distal end. It is a potential advantage to present the tissue as viewed from a point further away from the distal end of the catheter probe, and potentially advantageous to overlay its graphics, by providing to the surgeon a rendered model having an easily detected rendering viewpoint.

Exemplary Navigation

Reference is now made to FIGS. 3A to 3-D, exemplifying tissue model rendering as viewed from various viewpoint locations with respect to the catheter, in accordance with some embodiments of the invention.

Figure 3C:
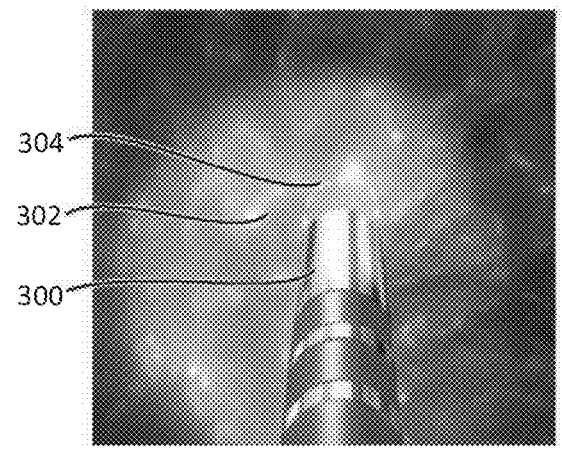
Figure 3D:
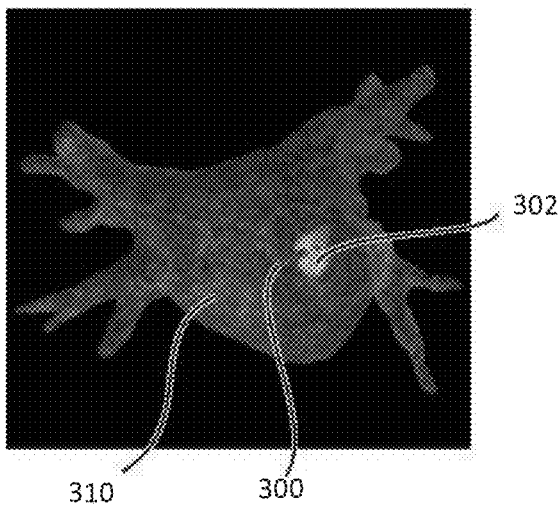

In some embodiments, a plurality of viewing perspectives is presented simultaneously, for example, viewing inside the patient-specific organ, such as shown in FIGS. 3A and 3C, together with viewing at least a portion of the patient's organ from outside, such as shown in FIGS. 3B and 3-D.

In some embodiments, a 3-D model is presented using a viewpoint being offset to the catheter probe and/or further away from the rendered tissue surface than the distal end of the catheter probe, defining a "first person" view, as shown in FIGS. 3A and 3C. In some embodiments, presenting the 3-D model also includes graphically presenting overlaying at least a portion of the distal end of the catheter probe. A potential advantage of overlaying the catheter distal tip over the 3-D model is in reducing the cognitive load which may be on a surgeon, as opposed to when he is provided with model viewpoints being along the catheter without actually seeing the catheter and having to interpret the catheter's position and/or orientation from deriving the viewpoint used to render the tissue.

In some embodiments, a plurality of viewpoints is provided, optionally presenting the same probe position and/or orientation. In some embodiments, using automatic dynamic image modification, tissue appearance and tissue shape changes can be viewed from the inside of the organ and/or can be viewed from outside the organ, optionally depending on the catheter's position and/or orientation and/or operation state. At least in some cases, having the same graphical marking shown in an inside view and seen from an outside view, helps a surgeon to orient himself.

In some embodiments, a catheter 300 is simulated to illuminate the tissue surface at 302 like a flashlight, e.g. simulated to produce a light beam as if originating from the catheter distal end. Optionally, the catheter is simulated to illuminate in the direction it is facing. In some embodiments, the catheter is simulated to project a flashlight producing a wide floodlight, having the potential advantage of simulating light over a relatively wide surface area, which likely due to its areal coverage, is also optionally detectable from a viewpoint location being outside the organ 310, as shown in FIGS. 3B and 3-D. Alternatively, the catheter is simulated to project a narrow beam, which potentially serves as an indicating marker, optionally indicative of the catheter's facing direction.

In some embodiments, light simulated to be projected from the direction of the catheter is shown by simulating diffuse lighting and/or specular lighting, in accordance with a 3-D shape defined by the tissue model.

In some embodiments, additionally to the flashlight illumination or alternatively to it, an indicating marker 304 illustrating the position and orientation of the catheter is graphically presented. Optionally, indicating marker 304 congruently matches the surface shape of the modeled tissue.

Figure 4A:
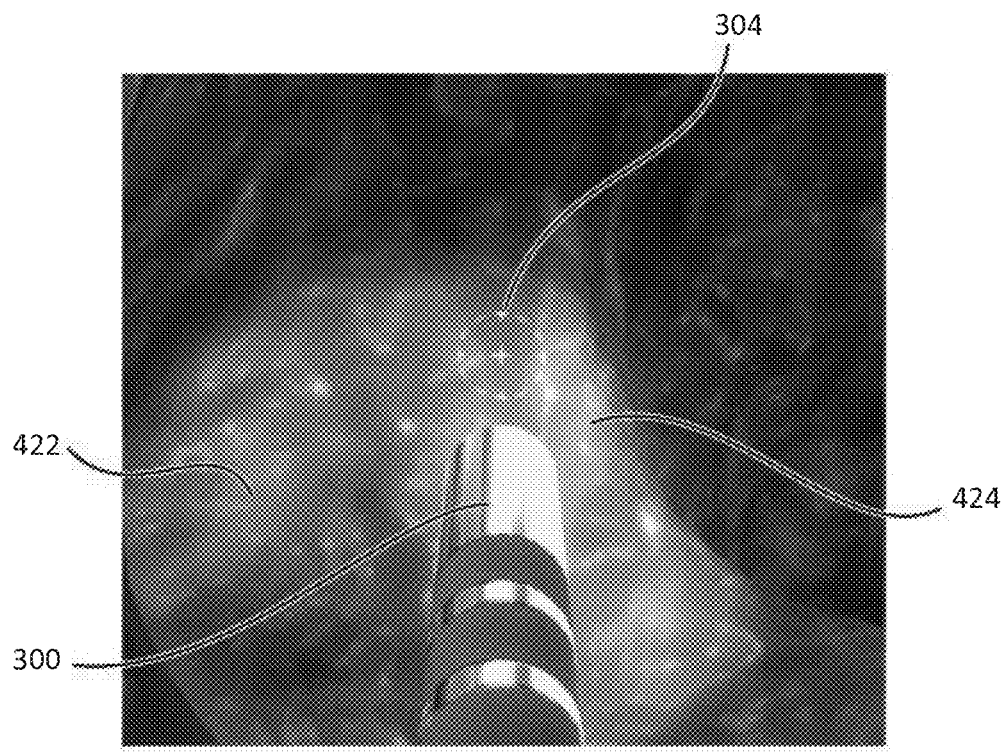
Figure 4B:
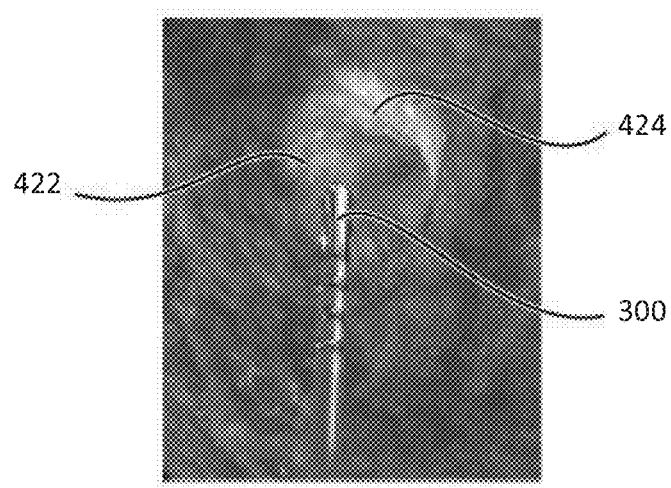

Reference is now made to FIGS. 4A-B, showing a simulation of the flashlight feature, in accordance with some embodiments of the invention. An aspect of several embodiments of the invention relates to simulating illumination projecting from a probe from the direction the probe is facing. In some embodiments, the illumination is simulated to be projected onto the surface of a 3-D model. Optionally, illumination is provided as a diverging, wide floodlight beam. Alternatively or additionally, illumination is provided as a coherent, narrow light beam. In some embodiments, illumination is projected from the inside of a tissue model and seen from the outside of the tissue model.

FIGS. 4A and 4B illustrate that an image generated according to some embodiments of the present invention may include different portions of the tissue surface lighted to differing degrees, for example, in dependency on the distance between the lighted surface and the distal end of the catheter. In the figures, tissue surface region 424 is closer to the distal end of catheter 300 than surface region 422; and is illuminated with stronger light.

FIG. 4A illustrates a viewpoint used to render the model of a "third person" view, optionally overlaying a representation of the catheter's distal end. As used herein, a "third person" view includes presenting the 3-D model having a field of view which includes the distal end of the catheter probe, the tissue region being viewed by the distal end of the catheter probe 300, and optionally the indicating marker 304 signifying the viewpoint of the distal end of the catheter probe. For example, FIG. 4A exemplifies a viewpoint being above the catheter probe and being further away from the tissue than the distal end of the catheter probe. In this exemplary embodiment, an overlay of the distal end of the catheter probe is provided.

FIG. 4B exemplifies a zoom out of an out-of-organ view, of the same configuration shown in FIG. 4A, but shown from outside the organ. In some embodiments, closer tissue surface portions such as 424 are rendered using MAPs providing the appearance as if the tissue surface reflects light more intensely and in a more focused manner than tissue surface portion 422.

In some embodiments, the viewpoint used to render the tissue model is shifted automatically, for example, from the view of FIG. 4A to that of FIG. 4B or vice versa. Optionally, a modification in presented images is based on probe position and/or probe orientation and/or probe trajectory and/or probe activity. For example, once an ablation process is detected, the image may be modified to a graphical animation illustrating the ablation procedure, optionally graphically visualized based on real-time physiologic input.

Reference is now made to FIGS. 5A to 5D, illustrating a geometric-specific indicating marker 304, in accordance with some embodiments of the invention. In some embodiments, an indicating marker is rendered across a region of the surface of a 3-D tissue model. Optionally, the projection is from a viewpoint defined along the catheter probe and/or facing the facing direction of the catheter probe. Alternatively or additionally, the viewpoint is in the direction of a selected (e.g., selected by a plan and/or by an indication made by operation of a user interface) target site. FIGS. 5A-D illustrate four congruent matchings of indicating marker 304 over the 3-D modeled tissue surface provided in a region to be marked, which is optionally determined by the relative position and/or facing direction of the catheter probe relative to the modeled tissue.

A potential advantage of rendering a congruently matched indicating marker and/or flashlight illumination, both deformed to the geometric 3-D surface of the tissue model, is the dynamic nature of the marker when moving over the surface of the modeled tissue, retaining the reactiveness of the graphical object to its virtual environment. This is distinguished from a simple icon overlay which does not match to the specific tissue surface region it is rendered on.

Figures 5E, 5F, 5G:
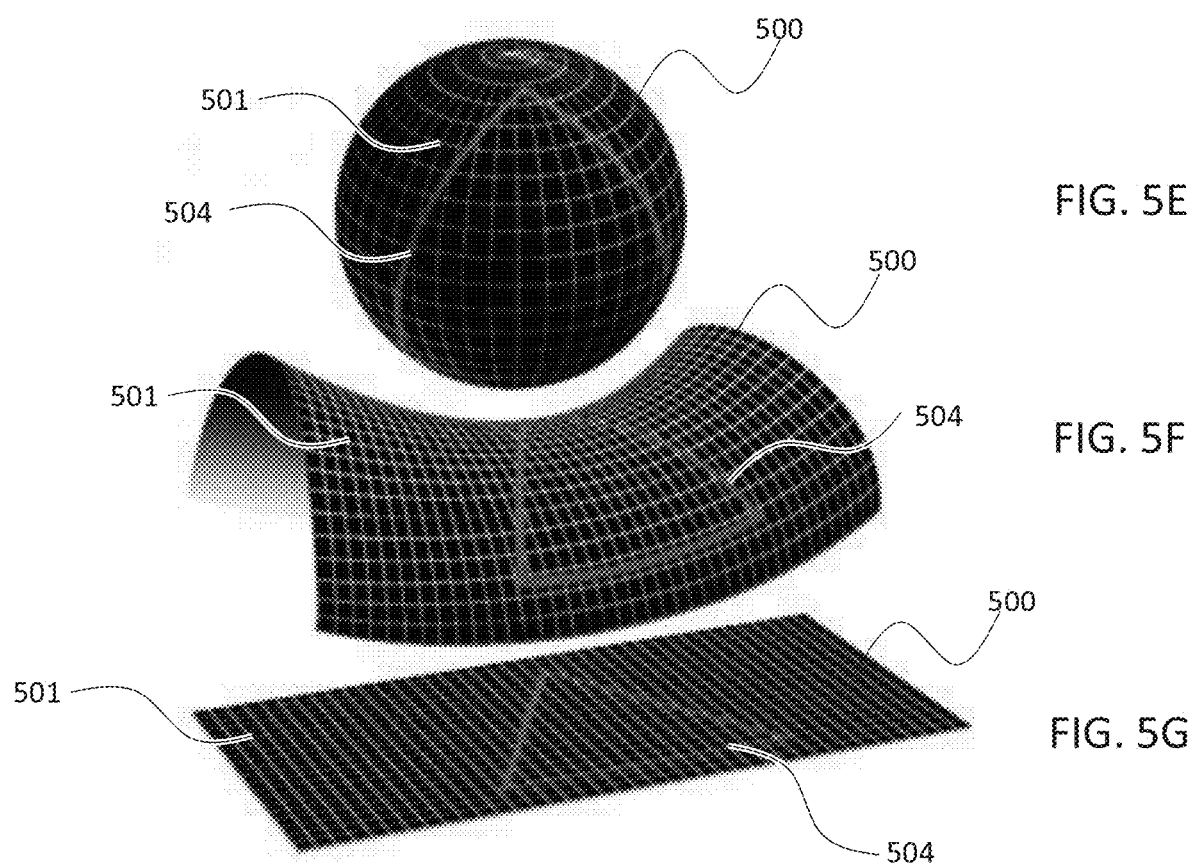
FIGS. 5E-5G illustrate various schematic deformations and congruent matching of an indicating marker to a surface.

Reference is now made to FIGS. 5E to 5G, illustrating a schematic, surface shape-specific indicating marker 504 fitted onto a surface of a schematic 3-D model 500, in accordance with some embodiments of the invention. An indicating marker is shown as a schematic example as the graphical object of triangle 504. Marker 504 may include the sides of the triangle and/or the interior of the triangle. FIGS. 5E-5G illustrate how marker 504 is deformed to match the 3-D model 500, at a plurality of positions, illustrated for example in these schematic illustrations as the meeting points of marker 504 with lines making up grid 501. Also exemplified herein, is that marker 504 is rendered across a region of the 3-D model, the region is shown by the delimitation of marker 504 in the form of a grey line.

FIG. 5E illustrates marker 504 in the form of a triangle being deformed to match 3-D model 500 in the form of a sphere. In this example, marker 504 is deformed to have a concave shape, fitted to the 3-D geometric surface of model 500.

FIG. 5F illustrates marker 504 in the form of a triangle being deformed to match 3-D model 500 in the form of a convex surface. In this example, marker 504 is deformed to have a convex shape, fitted to the 3-D convex geometric surface of model 500.

FIG. 5G illustrates marker 504 in the form of a triangle being deformed to match 3-D model 500 in the form of a plane. In this example, marker 504 is deformed to have a perspective shape, fitted to the 3-D plane of model 500.

Exemplary Target Identification

Reference is now made to FIGS. 6A to 6F, showing a simulation of identifying a target and starting an ablation, in accordance with some embodiments of the invention. FIG. 6A illustrates a visual representation of catheter probe 300 being oriented toward the left pulmonary veins, illustrated by left superior pulmonary vein 602 and left inferior pulmonary vein 604. Also shown are right superior pulmonary vein 606 and right inferior pulmonary vein 608.

In some embodiments, when a target is identified, either through planned settings and/or identification of user input indicative as identifying a target, the visual representation of the 3-D model is modified, optionally automatically. In some embodiments, modification of the 3-D model is provided by modifying the viewpoint used to render the model, such as for example, zooming in on the target site (as shown in FIG. 6B), or for example, switching into a cross-section view (as shown in FIG. 6F). Alternatively or additionally, modification of the presentation of the 3-D model is provided by presenting an indicating marker, such as for example, a planned path and/or marking (as shown in FIGS. 6C-6E).

Exemplary Ablation Visualization

In some embodiments, ablation treatment of a tissue region (for example, cardiac tissue of the atria) comprises the formation of a substantially continuous lesion of tissue which serves as a block to conduction. In some embodiments, the targeted region to block is along a lesion path 610 formed from a plurality of sub-lesions 620 arranged along it in a substantially contiguous fashion. Shown in FIGS. 6A-F and 7A-F, for example, is a lesion path 610 which encircles two pulmonary veins 602 and 604 of a left atrium (a view from inside the atrium is shown).

In appearance, FIGS. 6A-6F comprise visually rendered images (by a 3-D graphics engine) of an RF ablation probe 300 and its position relative to tissue targeted for ablation. Optionally, the rendering is in color, and/or otherwise using applied material appearance properties conveying the vital appearance (e.g., properties of roughness, specular reflection, etc.) of the tissue (black and white is shown herein for purposes of illustration).

In some embodiments, once catheter 300 is detected to be oriented towards a target site, the viewpoint used to render the model is modified, optionally, by zooming in, as exemplified in FIG. 6B illustrating a close up on the left pulmonary veins. Alternatively, this view is triggered when contact is sensed by a sensor on the probe, such as a pressure sensor and/or dielectric sensing of contact. The triggering is optionally visually implemented as a jump from a wider angle view with the probe out of contact to a close-up of the probe contacting tissue. Optionally, transition from no-contact to contact (or vice versa) is visually shown by a short bridging animation. In some embodiments, continuous sensing of probe position and/or probe distance to the tissue wall, allows any jump in a sensed transition between contact and non-contact to be smoothed out using actual position data.

In some embodiments, zooming in or zooming out is dynamic. Optionally, zooming in leads to increased resolution of guide markers. Exemplary guide markers 610 and 620 are illustrated in FIGS. 6C-6E, where each figure illustrates a closer view of the target site, and each closer view shows more details, for example, the ablation path 610 is first shown in FIG. 6C and the ablation area markers 620 are then shown in FIG. 6D. The ablation area markers may correspond to planned ablation sub-lesions. In some embodiments, a single ablation area marker 622 is detected to be the target, and is optionally maintained at the center of the modeled region.

Optionally, adjacent ablation markers to the left 624 and/or the right 626 are also presented, potentially maintaining the larger view context.

In some embodiments, once catheter 300 is detected to contact ablation marker 622, the view is automatically switched, optionally to illustrate a cross-sectional view of the depth of the tissue marked by marker area 622. In some embodiments, markers 624 and/or 626 are also shown in this view, optionally having a dull and/or transparent appearance, to further focus the surgeon on the active marker being in contact with the probe. Optionally, the marker in contact is differentiated from other markers by simulating material appearance relating to at least one tissue property, such as for example simulating tissue layers, as shown in marker 622 in FIG. 6F. A potential advantage of showing details of tissue properties only in a marker area which is in contact with the catheter is reducing the cognitive load of a surgeon by focusing his attention, and also potentially reducing the load of a controller having to render these tissue properties to only a delimited area and/or depth.

Reference is now made to FIGS. 7A-7F, which schematically illustrate visual rendering of various stages of lesioning to block tissue conduction, for example for the treatment of atrial fibrillation, according to some exemplary embodiments of the present disclosure. It should be noted that FIGS. 7A-7F show the tissue in cross-section, which is a potential benefit for conveying to a surgeon information about achieved lesion parameters such as lesion depth and/or lesion transmurality.

In FIG. 7A, catheter probe 300 is shown approaching ablation site 622.

Optionally, adjacent ablation sites 624 and 626 are shown in a "non-active" representation, such as for example, looking dull, and/or represented in non-informative block coloring, and/or being transparent. Such a presentation may assist a surgeon in focusing on the targeted site only. In some embodiments, the different representations may indicate ablated and non-ablated sites.

For example, ablation site 622 may be the last site to be ablated along a path starting at 624, going through 626 and ending at 622. In some embodiments, FIG. 7A may be presented simultaneously with presenting FIG. 6D. Catheter probe 300 may comprise at least one electrode, acting as an ablation electrode, is moved sequentially along path 610 (FIG. 6D), ablating at a plurality of locations to create a chain sub-lesions 620 at each location. Lesioning is performed according to clinically relevant parameters for generating transmural atrial wall lesions.

Illustrated in FIG. 7B is an optional representation of catheter 300 being in contact with ablation site 622 through surface 702. Surface 702 is shown as being pushed by catheter 300 into the depth of the tissue, resulting in ablation site 622 being at a distinct level than its adjacent sub-lesions 624 and 626 (see also FIG. 6F).

In some embodiments, once ablation onset takes place, simulated material appearance changes are provided. For example, FIG. 7C illustrates surface 702 by graphically presenting warm, bright coloring, optionally originating at the simulated catheter 300 tip engaging with the tissue surface. This presentation may be the result of data indicative of actual warming of ablation site 622. The data may be collected in real-time, interpreted to estimate a temperature rise. Based on the estimated temperature rise, material appearance properties shown in FIG. 7C may be selected, as discussed, for example, in the context of FIG. 1B. As heating continues, real-time data may be collected, and the temperature may be estimated to rise further, causing a new selection of the MAPs, for example, as shown in FIG. 7D. In some embodiments, when transmural ablation is achieved, heat is shown to propagate into the entire depth of tissue 706, as shown in FIG. 7E.

In some embodiments, once ablation is detected to be done and/or calculated to be done, tissue 706 may be estimated to be scarred and/or cooler, and rendered using dull, cold colors. When catheter probe 300 is pulled away (FIG. 7F) Surface 702 is released from the pressure exerted by the catheter probe, optionally leading to the return of the surface to its original height.

In some embodiments, visual rendering of the geometric surface of the 3-D anatomical model of the patient's tissue or organ includes modifying the appearance based on intermediate results which can be monitored while the procedure is carried out. For example, properties of a lesion may be estimated during an ablation in progress (for example, based on measurement results of dielectric property and/or temperature) and visualized by having the appearance of the geometric surface change according to the measurements, such as by increasing the warmth and/or intensity of a color of a lesioned area as a function of estimated temperature distribution across a portion of the simulated tissue.

Alternatively or additionally, intermediate results may be extrapolated and the geometric surface then may change according to conditions estimated by extrapolation. For example, after heating by the catheter probe is stopped, the cooling may be measured for a short while, and the simulation may show the cooling to continue even after no further measurements are taken, based on extrapolation of the temperature measurements taken. Similarly, late stages of scarring may be presented based on extrapolations of measurements indicative of early stages of scarring.

In some embodiments, simulation comprises simulating a thermal effect of lesioning on the tissue, optionally based on patient specific thermal characteristics. Optionally, thermal stimulation effects comprise coloring according to a probe heat level and/or a heat propagation characteristic of a tissue.

Alternatively or additionally, the simulation comprises simulating tissue properties. Simulated tissue properties may include, for example, texture profile, e.g. a presence of connective tissue and/or muscle tissue and/or arteries and/or veins. Alternatively or additionally, simulated tissue properties may include tissue composition, e.g. protein profile and/or fiber direction and/or scar presence and/or concentration of a specific protein, such as for example hemoglobin.

Optionally, patient-specific tissue properties as identified by pre-acquired data, data acquired during the procedure, are graphically represented using tissue properties. In some embodiments, patient-specific tissue properties include for example fibrosis and/or patchy fibrosis and/or scars and/or previous ablation lines Optionally, the ablation is by catheter ablation; for example: RF ablation, cryoablation, ultrasound ablation, laser ablation, electroporating ablation, or another form of ablation. Optionally, the tissue to be ablated is a region of atrial wall, for example, regions of the left atrial wall around the pulmonary veins for treatment of atrial fibrillation. Optionally, other tissue is ablated, for example, heart muscle to remove outflow blockage occurring in hypertrophic obstructive cardiomyopathy, neural tissue for treatment by neuromodulation, cancerous tissue for oncological treatment, another tissue, or one of these tissues for a different treatment purpose.

In some embodiments, lesion representation, all through its generation and immediately following ablation, conveys animation of intra-tissue properties. Optionally, temperature progression in 3-D is graphically presented based on thermodynamic simulation. In some embodiments, thermodynamic simulation is based on data input such as probe attack angle and/or a quality of an electrode-tissue interface contact area. In some embodiments, graphical representation of gradually ablated tissue is changed over time, for example, changing color and/or texture appearance, optionally following a predetermined algorithm. In some embodiments, tissue thickening is graphically presented to indicate edema accumulation.

In some embodiments, the method comprises estimating results of lesioning, based on real-time measurements. Optionally, estimated results include short-term effects such as heating and/or collateral effects on nearby tissue and/or reversible block and/or edema. Alternatively or additionally, estimated results include predictions of long-term effects such as the irreversibility of block.

Reference is now made to FIG. 8, illustrating an ablation overview presentation, in accordance with some embodiments of the invention. In some embodiments, when a catheter is pulled away from an ablation sub-lesion, and/or when a planned ablation is done, and/or when the catheter is lost, the view shifts automatically to present an overview of the ablation process being done so far.

Illustrated in FIG. 8 is an inner view of the left and right pulmonary veins, 602, 604, 606, 608. In some embodiments, an ablation overview simulates actual ablation sub-lesions in accordance with their extrapolated state of advancement since the ablation took place. Optionally, tissue which is estimated to be fully scared is simulated to present high color intensity, and optionally, a tissue which is simulated to be in an ongoing process, is presented in lower color intensity, which is correlated with the ablation extrapolated progress.

For example, 802*a* and 802*b* represent ablation sites where ablation has completed Ablation mark 804 represents an ablation site where ablation is in an advanced stage. Ablation mark 806 represents an ablation where ablation is in mid stage. Ablation mark 808 represents simulation of ablation in an initial stage.

Exemplary Neuromodulation

Reference is now made to FIGS. 9A-G, illustrating cardiac neuromodulation simulation, in accordance with some embodiments of the invention. Optionally, tissue is shown in cross-section, as for example in FIGS. 9B-9G. Cross-sectional view has a potential advantage for allowing the penetration size to be clearly seen. Additionally or alternatively, in some embodiments of the invention, transparency effects are applied to allow seeing into a targeted volume of tissue.

For example, before ablation begins, a local region of tissue selected by the position of the probe is shown with increased transparency. Optionally, as portions of the tissue become lesioned, they are represented in simulated display as more opaque; creating an ablation "island" that directly shows the progress of lesioning. A potential advantage of this approach is to allow representation of lesioning progress from any arbitrary 3-D point of view including the targeted tissue region.

FIGS. 9B-9D represent visually rendered cross-sectional view of a tissue region as viewed when it is being approached and/or contacted by ablation catheter 300, as shown in FIG. 9A. In some embodiments, ablation is directed towards ganglia 902. The ablation markings 972-976 shown in a tissue depth are similar to the guide markers shown in FIGS. 7A-F, wherein the rendered simulated tissue depth region is 972, heating is simulated by applying material appearance properties relating to heat 974 and scarring and/or cooling is simulated by applying material appearance properties relating to cooling 976. In some embodiments, the user interface includes a data inset 922 presenting to the surgeon data pertaining to the ongoing procedure.

FIGS. 9E-9G represent a visually rendered cross-sectional view of a tissue region as it is penetrated by needle 1070 of an injection probe 930 positioned to modulate and/or ablate activity of a ganglion 902 using an injected substance 1002. In the respect of allowing visualization of the effects of a treatment through a volume of tissue, this cross-section is similar to cross-sections of FIGS. 9A-9D showing the effects of RF ablation. In some embodiments, the distribution of injected material 1002 and/or displacement of nearby tissue by injected material 1002 is determined by one or more parameters including diffusion constants, injection volume, viscosity, projected pharmaceutical effects, etc., reflected in changes to the material appearance of the surface defined by the 3-D model representing the tissue region. The material appearance properties are optionally selected to visually trace the modeled distribution of the injected material 1002, and/or to visually indicate actual and/or intuitively "metaphorical" effects on tissue (e.g., a smoothing of the tissue evocative of relaxation).

Exemplary Validation

In some embodiments, measured dielectric properties of tissue are used to determine if an ablation lesion meets one or more targeted criteria. For example, in the case of treatment for atrial fibrillation, it is optionally determined if a lesioned region of tissue is of sufficient size, continuity, and/or degree of tissue transformation (such as by scarring and/or cellular disruption) to produce an irreversible block of impulse conduction. Effective blockage treatment of an irregular impulse conduction disease such as atrial fibrillation potentially fails when the blockage is broken or incomplete. Where it encounters a completed lesion, conduction is stopped. However, a gap potentially allows the impulse to escape into surrounding tissue, where it may contribute to an irregular heartbeat.

Reference is now made to FIGS. 10A-B, exemplifying a simulation of a validation procedure, FIG. 10A, and a simulated overview of a pre made plan when compared to the actual procedure, FIG. 10B.

Optionally, dielectric property measurements are made post-ablation to verify that changes associated with irreversible lesioning have occurred. Optionally, the measurements comprise comparison of post-ablation measurements with pre-ablation measurements. In some embodiments, once a validation tool 1030 identifies a gap in conduction blockage, material appearance of the validation overview is modified at the gap site, optionally by modifying the appearance of marking 620, for example by changing its color 1062.

In some embodiments, the sequence of preplanned position targets 620 is compared to the positions of actual targets 802 (e.g., tracked by a catheter tracking system) of an ablation catheter where it performs ablation. Optionally, the comparison occurs during an ablation procedure. In some embodiments, a graphical presentation of the planned 620 and actual ablation targets 802 is presented by being projected onto the patient-specific surface defined by the 3-D model representing the tissue region.

In some embodiments, a user interface also provides summary of the procedure, having data compared between planned and actual ablation 1022, and/or data describing the procedure itself 1024, and/or calculated compatibility between planned and actual 1026.

Exemplary System

An aspect of several embodiments of the invention relates to a system for matching guide markers with a 3-D model of tissue of a patient by updating the material appearance of the shape defined by the 3-D model, in accordance with some embodiments of the invention.

Reference is now made to FIG. 13, showing a block diagram of a system for sensing catheter-tissue relations and simulating such by rendering a tissue 3-D model. Illustrated below are potential catheter-tissue relations, which are useful in some embodiments of the invention.

Position data: In some embodiments (optionally), position data is sensed by use of an electromagnetic field navigation subsystem, comprising body surface electrodes 5, field generator/measurer 10, position analyzer 20, and catheter probe sensing electrodes 3. The electromagnetic field navigation subsystem operates by inducing at least one time-varying electromagnetic (EM) field 4 (for example, three crossed EM fields) across a region of body 2 including a body tissue region 3 which is targeted to be navigated by catheter 9 and catheter probe 11. Typically, the time varying EM field is induced with a total inter-electrode voltage of one volt or less, at a frequency of between about 10 kHz and about 1 MHz. Voltages sensed at different positions by sensing electrodes 3A are characteristic of corresponding intrabody positions, allowing conversion by position analyzer 20 of voltage measurements to position information (for example, after exploration of an intrabody region 3 using the probe 11, and/or initially based on EM fields simulated with respect to a particular configuration of electrodes and anatomical data 31).

Imaging data: Additionally or alternatively, in some embodiments, there is provided an imaging modality 6 that is configured during use to monitor at least one characteristic of the body tissue region 3 that optionally comprises position information of the probe and/or of tissue affected by operation of the probe. In some embodiments, the imaging modality is in continuous, real-time (e.g., 5, 10, 15, 20, 30, 60 or more images per second) use during at least some phase of a procedure. For example, the imaging modality 6 comprises ultrasound or fluoroscopy. Optionally, system 1 continuously processes changes in images for immediate display at user interface 55.

Additionally or alternatively, in some embodiments, an imaging modality 6 operates more infrequently (for example, once every minute to every five minutes, or at another interval). Though not immediately updating, slower imaging modalities 6 are optionally used for providing periodic "key frames" that are useful to synchronize and/or verify display of simulated and/or extrapolated states of tissue region 3 and/or catheter 9.

Dielectric property sensing: In some embodiments, dielectric property measurements providing indications of tissue state are made by dielectric property analyzer 22 using sensing electrodes 3A (or a subset thereof) to sense impedance behavior of electrical fields generated in conjunction with field generator/measurer 10, and optionally body surface electrodes 5. In some embodiments, dielectric property sensing is used to distinguish, for example, the state of tissue as healthy or fibrotic. Dielectric property sensing for this and other properties is described, for example, in International Patent Application No. IB2016/052690, the contents of which are incorporated by reference herein in their entirety.

General sensing: In some embodiments, other sensor information (sensed by optional other sensor(s) 14 on catheter probe 11) is used as interaction data. For example, a force sensor provides information on contact between a catheter probe 11 and its environment—that it has happened, and optionally with what degree of force. Additionally or alternatively, contact and/or contact force information is provided from sensing electrodes 3A in conjunction with other elements of the EM field navigation subsystem, based on impedance measurements. In some embodiments, other sensor(s) 14 comprise a temperature sensor, flow sensor, and/or another sensor configured to provide information about the environment of the catheter probe 11.

Treatment interactions: In some embodiments, a treatment element 8 is provided on catheter probe 11. The interaction data optionally comprises information about the operation of the treatment element and/or components controlling its effect.

The treatment element 8 is optionally a probe for ablation treatment; for example by radio frequency ablation, cryoablation, microwave ablation, laser ablation, irreversible electroporation, substance injection ablation, and/or high-intensity focused ultrasound ablation. In some embodiments, treatment element 8 is also used as a sensing electrode 3A (for example, in RF ablation, a treatment delivery electrode may also be used to sense the effect of local dielectric properties on measured electrical field impedance). Optionally, treatment element 8 is operated in conjunction with a treatment controller 13, configured to provide treatment element 8 with functions such as power, control and/or monitoring.

In some embodiments, the treatment element 8 is configured to deliver another treatment (for example, temporary activation or inactivation) using heat, cold, electrical current, sound radiation and/or light radiation. Optionally, the treatment element 8 comprises an injection apparatus, used to inject a treatment substance, and/or a substance used in diagnosis such an imaging tracer. In some embodiments, the injected substance comprises ethyl alcohol, Botox, living cells, and/or growth factor. Optionally, the injected substance comprises a radiolabeled substance, an immunosubstance, and/or a radiopaque trace substance.

Interaction data relating to the interactions of a treatment element 8 with a tissue region 3 comprising target sites for a procedure include, for example, duration of operation, time of operation, power and/or frequencies of energy delivered, nature and/or concentration of substances delivered, and/or quantities of substances delivered. Optionally, operational settings are combined with information about treatment element position and/or environment in order to derive interaction data.

It should be understood that not every source of interaction data described in relation to FIG. 13 is necessarily implemented in every embodiment of the invention. Preferably, there is provided in embodiments of the invention at least a position sensing modality and a monitored treatment modality.

Assignment of MAPs to Shapes Defined by a 3-D Model

In some embodiments of the invention, material appearance properties are assigned based on the output of one or more simulators 1110 (FIG. 11).

In some embodiments, sensing data 1101 and/or treatment status data 1102 are used directly or indirectly as input to one or more simulation modules 1110 (e.g., modules 1111, 1112, 1113, and/or 1114) which make adjustments to a modeled appearance state 1120 of the tissue based on inputs received, and one or more simulated aspects of tissue physiology, shape, and/or mechanics. Simulators 1110 also optionally receive as starting input anatomical data 31 and/or tissue state data 1104. In addition to adjusting the modeled appearance state 1120, simulators 1110 optionally maintain their own internal or mutually shared simulation states.

Reference is now made to FIG. 11, wherein different methods of providing probe interaction input to simulators 1110 are described.

Direct Sensing Input:

In some embodiments, basic simulation is implemented based directly on sensing data 1101. For example, a temperature reading from a temperature sensor 14 is optionally mapped directly to a color change selected according to the measured temperature. Additionally or alternatively, in some embodiments, a more involved simulation is performed: wherein probe interaction with a virtual material representing tissue is, in at least one aspect, physically and/or physiologically simulated in order to produce a new modeled appearance state.

Physiologically Interpreted Sensing Input:

In some embodiments, the use of sensing data 1101 by a simulator is indirect after interpretation by one or more physiology trackers 1106. Physiology tracker 1106, in some embodiments, is a module which accepts sensing data 1101 and converts it to an assessment of current physiological state. For example, in some embodiments, sensing data 1101 comprises dielectric measurements that physiology tracker 1106 is configured to convert into assessment of tissue state, for example as described in International Patent Application No. IB2016/052688, the contents of which are included by reference herein in their entirety. Additionally or alternatively, electrical activity indicating a functional state of the tissue itself is measured.

The output of the physiology tracker 1106 from one or more of these inputs is optionally in terms of one or more states such as lesion depth, lesion volume, degree of lesion transmurality, characterization of tissue edema, characterization of functional activity and/or inactivation, a classification as to a potential for tissue charring, and/or a classification as to a potential for steam pop. These outputs are optionally provided to a physiology simulator 1114 or an ablation physics simulator 1112, configured to convert such states into MAPs that indicate the state calculated from the measurements. Optionally, the interpreted tissue state also affects mechanical properties assumed, for example, by a contact physics simulator 1111 and/or an injection simulator 1113. It is a potential advantage to implement a physiological tracker 1106 as a distinct module which can be treated as a computational "service" to any appropriate simulator 1110. However, it should be understood that physiological tracker 1106 is optionally implemented as part of one or more simulators 1110 producing changes to a modeled appearance state 1120. In this case, the module configuration is more like that of direct sensing input, with the simulation of appearance integrated with physiological interpretation of the sensing data.

Positionally Interpreted Sensing Input:

In some embodiments, the use of sensing data 1101 by a simulator is indirect after interpretation by a probe position tracker 1107. Probe position tracker 1107, in some embodiments, is a module which accepts appropriate sensing data 1101 (e.g., electromagnetic field tracking data, acoustic tracking data, and/or imaging data) and converts it to a determination of the position (e.g., location and/or orientation) of a probe such as catheter probe 11.

Optionally position determination includes determination of tissue contact force and/or quality, using a force sensor on the probe, and/or for example as described in International Patent Application No. IB2016/052686, the contents of which are included by reference herein in their entirety. Additionally or alternatively, on-line imaging data (e.g., ultrasound and/or angiographic images) are used, intermittently and/or continuously, to determine and/or verify probe position.

Probe position determinations are optionally used as inputs to any of the simulators 1110; for example in order to assign particular positions to measurements of other tissue states/properties, and/or to help characterize changes induced by probe interactions with tissue (e.g. distortions of tissue shape, and/or simulated effects of treatment procedures). It is a potential advantage to implement probe position tracker 1107 as a distinct module which can be treated as a computational "service" to any appropriate simulator 1110. However, it should be understood that probe position tracker 1107 is optionally implemented as part of one or more simulators 1110 producing changes to a modeled appearance state 1120.

Treatment Status Input:

In some embodiments, simulation is implemented based on treatment status data 1102. Optionally, treatment status data is applied directly to modeled appearance state; for example, as a mark at each position of activation treatment modality activation. Additionally or alternatively, in some embodiments, at least one aspect of the tissue and/or tissue/ probe interaction is physically and/or physiologically simulated in order to produce a new modeled appearance state, based on the treatment status data. For example, in some embodiments, a physiology simulator 1114 receives input indicating that a probe-delivered treatment operation has occurred at some particular position (optionally along with parameters of the treatment operation). Physiology simulator 1114 is optionally configured to model the reaction of tissue to the treatment, instantaneously (for example, due directly to energy delivered by an ablation treatment), and/or over time (for example, as an edematous reaction develops in the minutes following an ablation treatment). In another example, an injection simulator 1113 receives treatment status input indicating that a material injection is occurring. Injection simulator 1113 is optionally configured to model an appropriate reaction of tissue to the injected substance (e.g., ablation and/or inactivation). The reaction is optionally immediate, and/or includes a slow-developing component as the material diffuses from the injection site. Optionally, changes in shape due to the addition of material volume to the tissue are also modeled.

Use of a Graphical Game Engine in Real-Time Anatomical Navigation

Reference is now made to FIG. 12, which schematically represents components, inputs, and outputs of a graphical game engine 1200 operating to manage and render scene elements 1220 to motion frame-rate images 1240, according to some embodiments of the present disclosure.

In some embodiments of the invention, a graphical game engine 1200 is used not only to render images, but also to provide more generally the data structure and code framework of the "scene" and how it changes in response to time and input.

In broad outline, a graphical game engine 1200 comprises a collection of computer software components exposing one or more application programming interfaces (APIs) for use in describing, instantiating (initializing and maintaining), continuously updating, rendering, and/or displaying of scene elements 1220. The scene elements 1220 provided for the operations of graphical game engine 1200 optionally include, for example, descriptions of terrain 1221, objects, 1222, cameras 1223, and/or lighting elements 1222. Definitions are optionally expressed in terms of geometrical-type scene data 1225 (e.g. model assets, shapes, and/or meshes), and/or appearance-type scene data 1226 (e.g., image assets, materials, shaders, and/or textures). In some embodiments, 3-D model 1221 and material appearance properties (MAPs) data are initially produced already in a format which is directly used by graphical game engine 1200.

In some embodiments, scene elements 1220 are provided with simulated dynamic behaviors by an iterated series of calculated scene adjustments 1210. The scene adjustments 1210 are optionally implemented by a variety of software components for e.g., motion physics 1212, collision detection 1213, and/or scripts 1211. These are examples; graphical game engines 1200 optionally implement additional services, e.g., "destructibility". Scripts 1211 can be provided to simulate, for example, autonomous behaviors and/or the effects of triggered events. Scripts 1211 are optionally written in a general-purpose computer language taking advantage of APIs of the graphical gaming engine 1200, and/or in a scripting language particular to an environment provided by the core graphical gaming engine 1200. Graphical gaming engines optionally also accept integration with plugin software modules (plugins, not shown) which allow extending the functionality of the core graphical game engine 1200 in any of its functional aspects. For purposes of the descriptions provided herein, plugins which perform functions related to updating the scene state are also encompassed within the term "script" 1211.

For purposes of descriptions herein, the scripts (optionally including plugins) 1211 and scene elements 1220 are considered part of the graphical game engine 1211 as a functional unit. Optionally, for example, where reference is made particularly to the off-the-shelf graphical game engine apart from specialized adaptations for uses described herein, the term "core graphical game engine" is used.

For interactivity, graphical game engines 1200 accept user input 1214 (optionally including, but not limited to, inputs from devices such as mouse, keyboard, touch screen, game controller, hand motion detector; and for some embodiments of the current invention, optionally including inputs describing probe positions, treatment activation, etc.).

A typical graphical game engine also includes a rendering pipeline 1230 that may include one or more stages of 3-D rendering, effects application, and/or post-processing, yielding at least one stream of frame-rate images 1240. In some embodiments, the stages of the rendering pipeline 1230 include modules which implement simulated optical algorithms—not necessarily directly based on real-world physical laws—generally selected to produce a rendered result which visually gives to elements in the rendered scene the appearance of material substances.

Table 1 includes some examples of how graphical game engine features and concepts are optionally used in some embodiments of the current invention.

TABLE 1

Examples of Graphical Engine Feature/Concept Usage

| Feature/Concept | Examples of Use |
|---|---|
| Scene 1220 | Overall visually renderable model of environment and objects within it. |
| Terrain 1221 | Optionally used to represent geometry (i.e., shape) of the anatomical environment. |
| Objects 1224 | Probe 11 is optionally represented as a "game" object, and may optionally serve as a viewpoint anchor like avatars and/or tools in certain 3-D games. Significant features of the anatomical environment such as scars, lesions, and/or regions of edema, are optionally implemented as appropriately positioned objects, e.g., embedded in an environment of surrounding tissue. Guides and markers are optionally implemented as game objects. |
| Assets 1225, 1226 | Tissue, probe, guide, and/or other objects and/or their appearances are optionally instantiated from assets which represent available types of objects, their behaviors and/or their appearances. |
| Cameras 1223 | Cameras optionally define flythrough viewpoint(s) of the anatomy traversed by the catheter probe 11, and/or overview viewpoint(s) (showing probe and tissue from a remote viewpoint). Optionally, the position of catheter probe 11 defines one or more camera viewpoints by its position/or orientation. |
| Lighting 1222 | In addition to providing general lighting of the tissue being navigated, lighting 1222 is optionally defined to provide highlighting, e.g., of regions pointed at by the probe 11, indications of environmental state by choice of light color, light flashing, etc. Lighting is optionally used to implement MAPs non-locally (that is, a defined light source optionally is defined to illuminate simulated tissue to selectively change its material appearance, while not being part of the material properties of appearance of the simulated tissue as such). |
| Image Assets; Materials, Shaders, and Textures 1126 | MAPs which are also material properties of appearance, for example, defining the appearance of tissue as healthy muscle, edematous, fibrotic, heated, cooled, etc. |
| Particle Systems | Type of object optionally used for providing effects such as smoke/steam-like indications of ablation heating, spray, transfer of energy, etc. |
| Collision Detection 1213 and Motion Physics 1212 | Optionally used for interactions between probe and the geometry (shape) of the anatomical environment; optionally including deformation of the probe and/or the anatomy. As implemented by core graphical game engines, the term "physics" generally is limited to physics affecting movement/deformation of game objects such as collision, gravity, or destruction. |
| Scripts 1211 | Optionally used for animating and/or showing changes in dynamic features of the environment (lighting, terrain), view (camera position) and/or game objects: for example, development of lesions, development of edema, heating/cooling effects, and/or injection effects. Optionally, scripts are used to implement dynamic appearance, even though the underlying state representation is constant (e.g., coruscating and/or pulsing effects). |
| User Game Input 1214 | Optionally comprise inputs reflecting changes in probe position for guiding navigation through the scene, and/or determining camera position. |
| Multiplayer | During a procedure, there is optionally a plurality of different surgeons working simultaneously with a system according to some embodiments of the current invention. For example, while a primary physician manipulates the probe, one or more additional workers are optionally reviewing the simulated environment to locate next target sites for the probe, evaluate effects of previous ablations, etc. Optionally, there is more than one probe in use at a time, each of which is optionally treated as a different "player" with its own associated camera views and/or interaction capabilities. |

Procedure-Simultaneous Mapping

Reference is now made to FIG. 14A, which is a flow chart schematically describing a cardiac ablation procedure, wherein indicating marks are placed on a 3-D model which is developed from data obtained during the procedure itself, according to some embodiments of the present disclosure. Reference is also made to FIGS. 14B-14E, which show a phase of iterative intra-procedure reconstruction of a model 1500 of a right atrium 1510 and connecting blood vessels including the superior vena cava 1520 and inferior vena cava 1524, according to some embodiments of the present disclosure. Additional blood vessels represented by 3-D model 1500 are identified in FIG. 15. A catheter probe 1504 is also indicated at various positions within model 1500; this is a display rendering corresponding to an actual catheter probe moving within the right atrium 1510 being mapped, put in register with model 1500 according to the position of the distal end of the actual catheter probe. The actual catheter probe corresponding to catheter probe 1504 is also the probe used in mapping right atrium 1510.

For purposes of description, the general plan of the procedure is presumed known in advance (e.g., to ablate in the left atrium using an ablation catheter), and it is also presumed that details of target anatomy such as shape remain unknown until the performance of intracardiac mapping using an intrabody probe. In some embodiments, the 3-D model is completely generated from the current procedure's intracardiac mapping data. However, methods encompassing variations from these presumptions are also envisioned as belonging to some embodiments of the present invention; and may be implemented by one of ordinary skill in the art, changed from the descriptions herein as necessary. In particular, it is to be understood that in some embodiments, imaging data, atlas data, and/or previously acquired intracardiac mapping data are used to provide a starting point for a 3-D model, which is then detailed based on further intracardiac mapping data acquired. In some embodiments, another type of cardiac mapping and/or imaging is performed during the procedure.

It is also presumed, for purposes of description, that the mapping probe is an electrode probe, that the ablation probe is an RF ablation probe; and moreover that the two probes are optionally (and as described) the same probe. However, methods encompassing variations from these presumptions are also envisioned as belonging to some embodiments of the present invention; and may be implemented by one of ordinary skill in the art, changed from the descriptions herein as necessary. It is to be understood, for example, that the method is optionally carried out using one or more different probes, wherein the probe or probes in aggregate provide an anatomical mapping function and a treatment function. Adjustments of the method as necessary to apply to other organs and procedures are also considered embodiments of the present invention.

The flowchart begins, and at block 1402, in some embodiments, an intrabody probe is positioned in a region of the body (e.g., a cardiac chamber) containing tissue targeted for treatment; for example, within a left atrium comprising tissue target for ablation. In some embodiments, the probe is a catheter probe, and combines one or more electrodes useful for electrical field-based intrabody mapping with an electrode for ablation (optionally also used as one of the mapping electrodes), e.g., RF ablation.

At block 1404, in some embodiments, the probe is moved within the cardiac chamber, recording mapping data indicating interior surface details of the chamber wall while doing so. During the movements, a 3-D model of the cardiac chamber is gradually built from this data (e.g., using a suitably configured computer which receives the data), to a level of detail suitable to make at least an initial determination of one or more target regions for ablation. The 3-D model is displayed using a display of user interface 55, optionally being updated as it develops based on mapping data obtained over the course of the procedure.

At block 1406, in some embodiments, an initial treatment plan (e.g., an initial ablation plan) is generated. The plan may comprise elements, for example as described in relation to any of the preplanning, planning, and plan adjustment methods herein. For example, the plan may comprise a line along which ablation is planned to be performed, and/or a plurality of targeted sites (e.g., along the line) at which ablation is particularly planned to be carried out (e.g., by delivery of RF energy during contact between the ablation probe and the targeted tissue). Optionally, the plan is formed automatically by computer based on the general goal of the procedure and the details of known anatomy. For example, once the positions of pulmonary veins which are to be electrically isolated from tissue of the left atrium are known, the computer calculates the course of an ablation line surrounding them, optionally also particular sites along the ablation line at which ablation is to be performed, and optionally parameters of ablation like power and duration of ablation at those sites. In some embodiments, the automatic plan is adjustable by manual intervention (e.g., using user interface 55). In some embodiments, a user provides at least part of plan (e.g., a general course of an ablation line) manually. In some embodiments, planning comprises selection of one or more treatment sites using an orientation (pointing selection) and/or a contact of the probe (touching selection) with tissue to be treated. Optionally there is automatic adjustment and/or detailing of the manual plan as necessary.

At block 1408, in some embodiments, marks indicating aspects of the plan and/or status of the procedure (e.g., progress made, current probe position and/or orientation) are rendered. Examples of status of the procedure may include: progress made so far, current probe position and/or orientation, etc. The aspects of the plan and/or status of the procedure are optionally rendered upon the displayed surface of the 3-D model, and/or in conjunction with a volume of tissue represented by the 3-D model; for example, as described in relation to any one or more of FIGS. 1A-1E, and/or as shown in figures herein, for example, as ablation lines and targeted ablation sites (e.g., as in FIGS. 6A-6E), state of ablation in progress (e.g., as in FIGS. 7A-7F), tissue state indications (e.g., indications of edema), and/or indications of probe position and/or orientation (e.g., as in FIGS. 3A-5D).

At block 1410, in some embodiments, further mapping data is recorded, and the heart chamber 3-D model updated in its shape (geometry) accordingly, for example as described in relation to block 1404.

FIG. 14B-14E show interim results of 3-D model updating from probe-based mapping data obtained within a right atrium 1510. It should be noted that features may be identified with a first shape during an earlier phase of the mapping, then refined, later on, to a more accurate and/or detailed shape on the basis of further information. This illustrates one reason why it is a potential advantage to have an accurate reference for monitoring and evaluating a procedure plan concurrently with the updated collection of 3-D model data representing the body region within which the procedure plan is actually carried out.

At block 1412, in some embodiments, data indicating operation of the ablation probe or another treatment device is optionally recorded.

At block 1414, in some embodiments, the plan generated at block 1406 is optionally adjusted, refined, and/or replaced, according to the data recorded in blocks 1410 and/or 1412. The adjustment can be, for example, as described to achieve any of the plan adjustment purposes described herein, for example, in relation to FIG. 2, and/or as described in the Overview.

From block 1416, in some embodiments, as long as the procedure continues and/or the probe remains within the heart chamber targeted for mapping and/or treatment, flow next returns to block 1408 for redisplay of the current plan and/or procedure state. Otherwise, the flowchart ends.

Probe Position Indicating Marks

Reference is now made to FIG. 15, which illustrates use of indicating marks 1501, 1502 for showing a current position of a tip 1505 of a probe 1504 positioned within a 3-D model 1500 of a body lumen, according to some embodiments of the present disclosure. The body lumen modeled comprises a region of a right atrium 1510 interconnecting between a superior vena cava 1520 and an inferior vena cava 1524. Also shown are a hepatic vein 1526, region of renal vein buds 1528, and coronary sinus 1522. The position, including orientation, and movements of probe 1504 within 3-D model 1500 are synchronized to actual movement of the probe within a body lumen corresponding to 3-D model 1500.

Two indicating marks 1501, 1502 are shown, each mapped to a surface of 3-D model 1500. The center point of mark 1501 shows the position at which a longitudinal axis extending distally from probe 1504 (that is, an axis extending distally along a facing direction of a distal portion of probe 1504) intersects the surface of model 1500. The center point of mark 1502 is centered on a surface point of 3-D model 1500 which is closest to a point at the tip 1505 of probe 1504.

During a procedure, the marks 1501, 1502 are moved around, each according to their respective placement rule, as data indicating the new position, including orientation, of probe 1504 are received. The marks 1501, 1502 are placed on the surface of model 1500 so that they conform to the surface shape as described, for example, in relation to FIGS. 3A-5D. Mark 1502 appears foreshortened, for example, because of the orientation of the surface portion which it occupies. Optionally, marks 1501, 1502 are distinguished by one or more of color, shape, and size. For example, mark 1501 is optionally a red mark, while mark 1502, is optionally a blue mark. Optionally, size of marks 1501, 1502 varies with distance from the probe 1504; for example, size is optionally chosen to maintain a fixed angular size (or fixed angular size with offset, similar to a flashlight beam emanating from an extended source) with respect to an origin located at some reference location defined by the position of probe 1504. Optionally, when the placement rules of mark 1501 and 1502 result in positions that substantially coincide, and/or when probe 1504 is determined to be positioned touching a surface of model 1500, a combined mark (not shown) is used, optionally with a distinction in size, shape, and/or or color; for example, a green color.

Any one or both of indicating marks 1501, 1502 are optionally simulated as a surface feature of a 3-D model (e.g., modeled by changing a material property of appearance of the surface such as absorption, scattering, glowing, and/or reflectance), and/or as an illuminated surface portion of a 3-D model (e.g., a "flashlight" type beam and/or a shape of a beam projected as if from a shaped light source; for example, similar to the effect of light projected from a focused image plane or a pattern-scanning point source).

Potential advantages relating to effects on how a procedure is performed for, e.g., an indicating mark such as indicating mark 1501 in discerning orientation of a probe relative to a pointed-at surface are discussed in the Overview, herein. A potential advantage of the combined use of marks 1501 and 1502 is to assist in coordinating contact with orientation during manipulation of a catheter probe to reach, e.g., a treatment site. As the probe approaches the surface, the rules governing rendering of the two marks 1501, 1502 are such that the closer together the two marks 1501, 1502 are at a certain distance, the closer (in many but not all cases) the probe will be to an orthogonal approach to the surface being approached. Also, during probe manipulation, "what surface is nearest" and "what surface is pointed at" may be simultaneously and/or alternatively of interest. For example, when a probe is oriented toward a distant surface location, it may be relatively safe to advance the probe quickly along a vessel or other nearby surface in order to obtain mapping points along a larger extent more quickly. The surface can be selected by moving the probe while observing the position of indicating mark 1502, and the selection of a clear path for advancing the probe can be performed by at the same time controlling the position of indicating mark 1501 to target a distant surface position.

General

As used herein the term "about" refers to ±25%. The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of graphically presenting a 3-D model of a tissue region during a catheterization procedure, the method comprising:
   estimating an estimated effect of said catheterization procedure on said tissue region;
   calculating, based on said estimated effect, a shape, a size, and a position of a region to be marked on the 3-D model;
   dynamically selecting and changing one or more material appearance property based on said estimated effect, wherein the changing of the at least one or more material appearance properties is in accordance with real time temperature estimation of the tissue region; and
   dynamically rendering said 3-D model to present the estimated effect comprises using the selected material appearance properties across the region to be marked, wherein said rendering comprises:
   rendering a surface of said tissue region; and
   dynamically rendering a marking on said surface, said dynamically rendering a marking on said surface including deforming said marking to match a surface contour of said surface.

2. The method according to claim 1, wherein said estimated effect comprises at least one of an estimated change in temperature, an estimated change in shape and an estimated change in size of said tissue region.

3. The method according to claim 1, wherein said calculating a shape comprises calculating an area of an ablation point.

4. The method according to claim 1, wherein said calculating a shape comprises calculating a depth of an ablation point.

5. The method according to claim 1, wherein said calculating a shape includes calculating a path of a plurality of ablation points.

6. The method according to claim 1, wherein said material appearance properties are selected to visualize a state of said tissue region.

7. The method according to claim 1, wherein said shape is recalculated as a function of time.

8. The method according to claim 1, wherein said shape and said material appearance properties indicate an increasing spread of a lesioning effect.

9. A method according to claim 1 and wherein said dynamically rendering said 3-D model comprises rendering to indicate a position and a facing direction of a catheter probe during said catheterization procedure, the method comprising:
   determining said position and facing direction of a distal end of said catheter probe with respect to said tissue region; and
   wherein said dynamically rendering said 3-D model comprises dynamically rendering said 3-D model to include a simulation of said marking, said marking being simulated in a position of said surface portion defined by said 3-D model, wherein the position is also located along an axis extending distally from said determined position and in said determined facing direction of said distal end of said catheter.

10. The method of claim 9, further comprising rendering said 3-D model to include a simulation of a second indicating mark, said second indicating mark being simulated in a position of a second surface portion defined by said 3-D model, wherein second surface portion occupies a closest surface position of said 3-D model to a predefined portion of said distal end of said catheter.

11. The method of claim 10, wherein said marking and said second indicating mark are rendered together as a single indicating mark when the determined position of the distal end indicates contact with a surface defined by the 3-D model.

12. The method according to claim 10, wherein both said marking and said second indicating mark are shaped and positioned to congruently match the corresponding 3-D model surface portion.

13. The method according to claim 9, wherein said 3-D model is rendered as viewed from a viewpoint from outside an organ comprising said tissue region.

14. The method according to claim 9, wherein said 3-D model is rendered as viewed from a viewpoint from within an organ comprising said tissue region.

15. The method according to claim 9, wherein said tissue region comprises an inner surface of a body lumen.

16. The method according to claim 9, wherein said 3-D model is rendered as viewed from a viewpoint offset to said distal end of said catheter probe.

17. The method according to claim 9, wherein said marking is simulated as an illumination of said 3-D model surface.

18. The method according to claim 17, wherein a center of said illumination is calculated according to a position and facing direction of said catheter probe relative to said tissue region.

19. The method according to claim 17, wherein said selected material appearance properties is simulated to be affected by said illumination.

20. The method according to claim 17, wherein said rendering comprises rendering said tissue region as at least partially translucent to said simulated illumination.

21. The method according to claim 9, further comprising simultaneously presenting two or more views of said 3-D model, each viewed from a different viewpoint, the different viewpoints comprising a first viewpoint being inside an organ comprising said tissue region and a second viewpoint being outside said organ.

22. The method according to claim 18, wherein the center of said illumination is graphically presented by increased illumination intensity at a center of a beam of said illumination.

23. The method according to claim 9, further comprising also presenting a view of a cross-section of a tissue depth.

24. A method according to claim 1, wherein said marking comprises an indicating marker to be graphically presented over said 3-D model of said tissue surface during said catheterization procedure using a catheter probe, the method comprising:
   determining said region over said 3-D model; and
   wherein said deforming comprises deforming said indicating marker to obtain a deformed indicating marker that congruently matches a shape defined by said 3-D model across said region at a plurality of positions; and
   wherein said dynamically rendering said 3-D model comprises dynamically rendering said 3-D model into an image including said deformed indicating marker by generating an image of said 3-D model covered by said deformed indicating marker across said region defined by said plurality of positions.

25. The method according to claim 24, wherein said indicating marker indicates a field of view viewed from a location along said catheter probe, said location being determined by a measured position and facing direction of a distal end of said catheter probe.

26. The method according to claim 24, wherein an appearance of said indicating marker indicates a relative location of said catheter probe with respect to said tissue surface, said relative location being determined based on a measured position and facing direction of a distal end of said catheter probe relative to said tissue surface.

27. The method according to claim 24, wherein a size of said region indicates a distance between said catheter probe and said tissue surface.

28. The method according to claim 24, wherein a visibility of said indicating marker indicates a distance between said catheter probe and said tissue surface.

29. The method according to claim 24, wherein an aspect ratio of said region indicates an orientation between said catheter probe and said tissue surface.

30. The method according to claim 24, wherein said indicating marker indicates a planned path.

31. The method according to claim 24, further comprising identifying said indicating marker should be presented, said identifying is based on rules pre-associated with input expected to be acquired during said catheterization procedure.

32. The method according to claim 31, wherein said input comprises an identified onset of an ablation.

* * * * *